US008937161B2

(12) United States Patent
Mao et al.

(10) Patent No.: US 8,937,161 B2
(45) Date of Patent: *Jan. 20, 2015

(54) CYSTEINE ENGINEERED ANTI-TENB2 ANTIBODIES AND ANTIBODY DRUG CONJUGATES

(75) Inventors: Weiguang Mao, San Mateo, CA (US); Jagath Reddy Junutula, Fremont, CA (US); Paul Polakis, Mill Valley, CA (US)

(73) Assignee: Genentech, Inc., South San Francisco, CA (US)

( * ) Notice: Subject to any disclaimer, the term of this patent is extended or adjusted under 35 U.S.C. 154(b) by 815 days.

This patent is subject to a terminal disclaimer.

(21) Appl. No.: 12/288,181

(22) Filed: Oct. 16, 2008

(65) Prior Publication Data
US 2009/0117100 A1 May 7, 2009

Related U.S. Application Data

(60) Provisional application No. 60/981,411, filed on Oct. 19, 2007.

(51) Int. Cl.
*C12P 21/08* (2006.01)
*A61K 47/48* (2006.01)

(52) U.S. Cl.
CPC ..... *A61K 47/48569* (2013.01); *A61K 47/48715* (2013.01)
USPC ........................................................ 530/387.3

(58) Field of Classification Search
USPC .......................................... 530/387.3, 391.1
See application file for complete search history.

(56) References Cited

U.S. PATENT DOCUMENTS

| 4,975,278 | A | 12/1990 | Senter |
| 5,182,261 | A | 1/1993 | Tam |
| 5,219,996 | A | 6/1993 | Bodmer et al. |
| 5,240,912 | A | 8/1993 | Todaro |
| 5,333,033 | A | 7/1994 | Blackman |
| 5,633,147 | A | 5/1997 | Meissner et al. |
| 5,635,483 | A | 6/1997 | Pettit |
| 5,767,237 | A | 6/1998 | Sakakibara |
| 5,831,058 | A | 11/1998 | Fujiwara et al. |
| 6,124,431 | A | 9/2000 | Sakakibara |
| 6,214,345 | B1 | 4/2001 | Firestone |
| 6,248,564 | B1 | 6/2001 | Walter et al. |
| 6,333,033 | B1 | 12/2001 | Genain et al. |
| 6,410,506 | B1 | 6/2002 | Wei |
| 6,642,006 | B2 | 11/2003 | Wei |
| 6,753,165 | B1 | 6/2004 | Cox et al. |
| 6,884,869 | B2 | 4/2005 | Senter |
| 7,097,840 | B2 | 8/2006 | Erickson et al. |
| 7,521,541 | B2 * | 4/2009 | Eigenbrot et al. ......... 530/387.1 |
| 7,785,816 | B2 | 8/2010 | Bhaskar |
| 7,824,678 | B2 | 11/2010 | Bhaskar |
| 7,855,275 | B2 * | 12/2010 | Eigenbrot et al. ......... 530/387.1 |
| 2002/0025551 | A1 | 2/2002 | Holtzman |

| 2003/0083263 | A1 | 5/2003 | Doronina |
| 2004/0005324 | A1 | 1/2004 | Pilkington et al. |
| 2004/0018194 | A1 | 1/2004 | Francisco |
| 2004/0096392 | A1 | 5/2004 | Bhaskar |
| 2004/0229310 | A1 | 11/2004 | Simmons |
| 2004/0235068 | A1 | 11/2004 | Levinson |
| 2005/0048572 | A1 | 3/2005 | Reilly et al. |
| 2005/0238649 | A1 | 10/2005 | Doronina |
| 2006/0121467 | A1 | 6/2006 | Foekens |
| 2006/0246433 | A1 | 11/2006 | Adorjan |
| 2007/0092940 | A1 | 4/2007 | Eigenbrot |
| 2007/0128592 | A1 | 6/2007 | Burger |
| 2007/0237770 | A1 | 10/2007 | Lai |
| 2008/0044840 | A1 | 2/2008 | Bhaskar |
| 2008/0050310 | A1 | 2/2008 | Ebens et al. |
| 2008/0160012 | A1 | 7/2008 | Bhaskar |
| 2008/0247951 | A1 | 10/2008 | Koch et al. |
| 2008/0254447 | A1 | 10/2008 | Foekens |
| 2008/0311134 | A1 * | 12/2008 | Junutula et al. ............ 424/178.1 |
| 2009/0028856 | A1 | 1/2009 | Chen et al. |
| 2009/0068202 | A1 | 3/2009 | Chen et al. |

(Continued)

FOREIGN PATENT DOCUMENTS

| CA | 2153480 | 6/1995 |
| EP | 0 154 434 | 1/1993 |

(Continued)

OTHER PUBLICATIONS

Junutula, et al., "Thiomabs: improving safety abd retaining efficacy of antibody drug conjugates", AACR, vol. 48, pp. 220-221, (2007).
Lambert, et al., "Drug-conjugates monoclonal antibodies for the treatment of cancer", Current opinion in pharmacology, vol. 5, No. 5, pp. 543-549, (2005).
Mao, et al., "TenB2 as a therapeutic antibody drug target for the treatment of prostate cancer", MCT, vol. 6, No. 12, p. 3356S, (2007).
Adams et al., "Rapid CDNA Sequencing (Expressed Sequence Tags) from a Directionally Cloned Human Infant Brain CDNA Library", Nature Genetics, New York, NY, US, 4:373-380 (1993), XP000574910, ISSN: 1061-4036.
Adams et al., "Sequence Identification of 2,375 Human Brain Genes", Nature, Nature Publishing Group, London, GB., 335(6361):632-634 (1992), XP000914512, ISSN: 0028-0836.

(Continued)

*Primary Examiner* — Brad Duffy
(74) *Attorney, Agent, or Firm* — Janet Martineau; Yuko Soneoka; Arnold & Porter LLP

(57) ABSTRACT

Cysteine engineered anti-TENB2 antibodies are engineered by replacing one or more amino acids of a parent anti-TENB2 antibody with non cross-linked, reactive cysteine amino acids. Methods of design, preparation, screening, and selection of the cysteine engineered anti-TENB2 antibodies are provided. Cysteine engineered anti-TENB2 antibodies (Ab) are conjugated with one or more drug moieties (D) through a linker (L) to form cysteine engineered anti-TENB2 antibody-drug conjugates having Formula I:

$$Ab\text{-}(L\text{-}D)_p \quad\quad\quad I$$

where p is 1 to 4. Diagnostic and therapeutic uses for cysteine engineered antibody drug compounds and compositions are disclosed.

37 Claims, 22 Drawing Sheets

(56) References Cited

U.S. PATENT DOCUMENTS

| | | | |
|---|---|---|---|
| 2009/0117100 A1 | 5/2009 | Mao et al. |
| 2009/0155776 A1 | 6/2009 | Lo |
| 2010/0069463 A1 | 3/2010 | Paez-Pereda |
| 2010/0092951 A1 | 4/2010 | Tetzner |
| 2010/0130417 A1 | 5/2010 | Wei |
| 2010/0130904 A1 | 5/2010 | Kirber |
| 2011/0038864 A1 | 2/2011 | Bhaskar |

FOREIGN PATENT DOCUMENTS

| | | | |
|---|---|---|---|
| EP | 1020522 | 7/2000 | |
| EP | 1 391 213 A1 | 2/2004 | |
| WO | WO 89/01974 | 3/1989 | |
| WO | WO 94/06474 | 3/1994 | |
| WO | WO 95/14772 | 1/1995 | |
| WO | WO 97/25349 | 7/1997 | |
| WO | WO 02/16429 | 2/2002 | |
| WO | WO 02/088172 A2 | 11/2002 | |
| WO | WO 03/043583 A2 | 5/2003 | |
| WO | WO 03/049704 | 6/2003 | |
| WO | WO 03/060080 | 7/2003 | |
| WO | WO 03/075855 A2 | 9/2003 | |
| WO | WO 2004/032828 A2 | 4/2004 | |
| WO | WO 2004/050849 | 6/2004 | |
| WO | WO 2005/117986 A2 | 12/2005 | ............ A61K 47/48 |
| WO | WO 2006/034488 A2 | 3/2006 | |
| WO | WO 2007/140371 A2 | 12/2007 | ............ C07K 16/28 |
| WO | WO 2008/141044 A2 | 11/2008 | ............ A61K 39/395 |

OTHER PUBLICATIONS

Afar, et al., "Preclinical validation of anti-TMEFF2-auristatin E-conjugated antibodies in the treatment of prostate cancer", Molecular Cancer Therapeutics, 3(8): 921-932, (2004).
Antal-Szalmas, P.,"Evaluation of CD 14 in Host Defence", European Journal of Clinical Investigation, 30(2):167-179 (2000).
Bennett, Barbara A., et al., "111V-1 gp 120-induced neurotoxicity to midhrain dopamine cultures", Brain Research, vol. 705, pp. 168-176, 1995.
Bernhard, et al., "Cysteine analogs of recombinant barley ribosome inactivating protein form antibody conjugates with enhanced stability and potency in vitro", Bioconjugate Chem., 5: 126-132, (1994).
Better, et al., "Gelonin analogs with engineered cysteine residues form antibody immunoconjugates with unique properties", The Journal of Biological Chemistry, vol. 269, Issue of Apr. 1, pp. 9644-9650, (1994).
Bhaskar, et al., "E-selectin up-regulation allows for targeted drug delivery in prostate cancer", Cancer Research, 63: 6387-6394, (2003).
Boring, et al., "Cancer Statistics, 1993", Ca Cancer J. Clin., vol. 43, No. 1, pp. 7-26, (1993).
Burgess, "Epidermal Growth Factor and Transforming Growth Factor Alpha", British Medical Bulletin 45(2): 401-424 (1989).
Chmura, et al., "Antibodies with infinite affinity", P.N.A.S., vol. 98, No. 15, pp. 8480-8484, (2001).
Davis, C. Geoffrey, et al., "The Many Faces of Epidermal Growth Factor Repeats", The New Biologist 2(5): 410-419, May 1990.
Davis, et al., "Identification of a family of Fc receptor homologs with preferential B cell expression", P.N.A.S., vol. 98, No. 17, pp. 9772-9777, (2001).
Derynck et al., "Human Transforming Growth Factor-Alpha: Precursor Structure and Expression in *E. coli*", Cell 38:287-297, Aug. 1984.
Doronina, et al., "Development of potent monoclonal antibody auristatin conjugates for cancer therapy", Nature Biotechnology, vol. 21, No. 7, pp. 778-941, (2003).
Francisco, et al., "cAC10-vcMMAE, an anti-CD30-monomethy 1 auristatin E conjugate with potent and selective antitumor activity", Blood, vol. 102, No. 4, pp. 1458-1465, (2003).
Glynne-Jones, et al., "TENR2, a proteoglycan identified in prostate cancer that is associated with disease progression and androgen independence", Int. J. Cancer 94: 178-184 (2001).

Greenwood, et al., "Engineering multiple-domain forms of the therapeutic antibody CAMPATH-LH: effects on complement lysis", Therapeutic Immunology, 1: 247-255, (1994).
Hinman, et al., "Preparation and characterization of monoclonal antibody conjugates of the calichcamicins: A novel and potent family of antitumor antibiotics", Cancer Research, 53: 3336-3342, (1993).
Hoogenboom, Hennie R., et al., "By-passing Immunisation Human Antibodies from Synthetic Repertoires of Germline V11 Gene Segments Rearranged in Vitro", J. Mot. Biol., vol. 227, pp. 381-388, 1992.
Horie, Masato, et al., "Identification and Characterization of TMEFF2, a Novel Survival Factor for Hippocampal and Mesencephalic Neurons", Genomics, vol. 67, pp. 146-152, 2000.
Ise, et al., "Elevation of soluble CD307 (IRTA2/FcRH5) protein in the blood and expression on malignant cells of patients with multiple myeloma, chronic lymphocytic leukemia, and mantle cell lymphoma", Leukemia, 21: 169-174, (2007).
Ise, et al., "Immunoglobulin superfamily receptor translocation associated 2 protein on lymphoma cell lines and hairy cell leukemia cells detected by novel monoclonal antibodies", Clinical Cancer Research, vol. 11, pp. 87-96, (2005).
Itoh, Kyoko, et al., "Neuronal damage of the substantia nigra in HIV-1 infected brains", Acta Neuropathol, vol. 99, pp. 376-384, 2000.
Jones, Peter T., et al., "Replacing the complementarity-determining regions in a human antibody with those from a mouse", Nature, vol. 321, pp. 522-525, May 29, 1986.
Junutula, et al., "Rapid identification of reactive cysteine residues for site-specific labeling of antibody-Fabs", Journal of Immunological Methods, 332: 41-52, (2008).
Kanno, et al., "Assembling of engineered IgG-binding protein on gold surface for highly oriented antibody immobilization", Journal of Biotechnology, 76: 207-214, (2000).
Kaser, et al., "Comparison between apidermal growth factor, transforming growth factor-$\alpha$ and EGF receptor levels in regions of adult rat brain", Molecular Brain Research, 16: 316-322, (1992).
Kawatani, et al., "Deletion of the BH1 Domain of Bc1-2 Accelerates Apoptosis by Acting in a Dominant Negative Fashion", The Journal of Biological Chemistry, vol. 278, pp. 19732-19742 (May 30, 2003).
Kuby, Janis, "Antigen-Antibody Interactions", Immunology, Second Edition, pp. 135-140, 1994.
Kumar, et al., "Transforming growth factor alpha", Cell Biology International, vol. 19, No. 5, (1995).
Lewin, B. (Editor), Genes IV, 1990 p. 812.
Liu, et al., "Eradication of large colon tumor xenografts by targeted delivery of maytansinoids", P.N.A.S., vol. 93, pp. 8618-8623, (1996).
Lode, et al., "Targeted therapy with a novel enediyene antibiotic calichaemicin $0^I_1$ effectively suppresses growth and dissemination of liver metastases in a syngeneic model of murine neuroblastoma$^1$", Cancer Research, 58: 2925-2928, (1998).
Lumadue, J.A. et al., "Cloning Sequence Analysis and Expression of the Large Subunit of the Human Lymphocyte Activation Antigen 4F2", Proc. Natl. Acad. Sci. USA, vol. 84, pp. 9204-9208 (1987).
Mandler, et al., "Immunoconjugates of geldanamycin and anti-HER2 monoclonal antibodies: Antiproliferation activity on human breast carcinoma cell lines", Journal of the National Cancer Institute, vol. 92, No. 19, pp. 1573-1581, (2000).
Mandler, et al., "Modifications in synthesis strategy improve the yield and efficacy of Geldanamycin-Herceptin immunoconjugates", Bioconjugate Chem., 13: 786-791, (2002).
Mandler, et al., "Synthesis and evaluation of antiproliferative activity of a Geldanamycin-Herceptin immunoconjugate", Bioorganic & Medicinal chemistry Letters, 10: 1025-1028, (2000).
Mao, et al., "EphB2 as a therapeutic antibody drug target for the treatment of colorectal cancer", Cancer Research, 64: 781-788, (2004).
Marks, James D., et al., "By-passing Immunization Human Antibodies from V-gene Libraries Displayed on Phage", J. Mol. Biol., vol. 222, pp. 581-597, 1991.
Marquardt, et al., "Transforming growth factors produced by retrovirus-transformed rodent fibroblasts and human melanoma cells: Amino acid sequence homology with epidermal growth factor", PNAS, vol. 80, pp. 4684-4688, (1983).

(56) References Cited

OTHER PUBLICATIONS

Matsubara et al., "Identification of New Genes by Systematic Analysis of CDNAs and Database Construction" Current Opinion in Biotechnology, London, GB, 4:6:672-677 (1993), XP002322875, ISSN: 0958-1669.
Miller, et al., "IRTAs: A new family of immunoglobulinlike receptors differentially expressed in B cells", Blood, vol. 99, No. 8, pp. 2662-2669, (2002).
Niculescu-Duvaz, et al., "Antibody-directed enzyme prodrug therapy (ADEPT): A review", Advanced Drug Delivery Reviews, 26: 151-172, (1997).
Payne, "Progress in immunoconjugate cancer therapeutics", Cancer Cell, vol. 3, pp. 207-212, (2003).
Perl, Daniel, et al., "Neuropathology of Dementia", Neurologic Clinics, vol. 4, No. 2, pp. 355-368, May 1986.
Petito, Carol K., et al., "Hippocampal Injury and Alterations in Neuronal Chemokine Co-Receptor Expression in Patients With Aids, Journal of Neuropathology and Experimental Neurology", vol. 60, No. 4, pp. 377-385, Apr. 2001.
Plata-Salamin, Carlos R., et al., "Epidermal Growth Factor and the Nervous System", Peptides, vol. 12, pp. 653663, 1991.
Polson, et al., "Expression pattern of the human FcRH/IRTA receptors in normal tissue and in B-chronic lymphocytic leukemia", International Immunology, vol. 18, No. 9, pp. 1363-1373, (2006).
Quayle, S.N. and Sadar, M. D., "A truncated isofoll of TMEFF2 encodes a secreted protein in prostate cancer cells", Genomics 87: 633-637 (2006).
Reyes M.D, Edgardo, et al., "Hippocampal Involvement Associated With Human Immunodeficiency Virus Encephalitis in Mexico", Arch. Pathol. Lab Med., vol. 118, pp. 1130-1134, Nov. 1994.
Reichmann, Lutz, et al., "Reshaping human antibodies for therapy", Nature, vol. 332, pp. 323-327, Mar. 24, 1988.
Rowland, et al., "Drug localisation and growth inhibition studies of vindesine-monnoclonal anti-CEA conjugates in a human tumour xenograft", Cancer Immnol. Immunother., 21: 183-187, (1986).
Sa, M. J., et al., "AIDS does not alter the total number of neurons in the hippocampal formulation but indices cell atrophy: a stereological study", Acta Neuropathol., vol. 99, pp. 643-653, 2000.
Schiff, D., et al, "Bilirubin toxicity in neural cell lines N115 and NBR10A", Pediatric Research, vol. 19, pp. 908911, 1985.
Senter, Proceedings of the American Association for Cancer Research, vol. 45, Abstract No. 623, presented Mar. 28, 2004.
Syrigos, et al., "Antibody directed enzyme prodrug therapy (ADEPT): A review of the experimental and clinical considerations", Anticancer Research, 19: 605-614, (1999).
Tu, et al., "Protein footprinting at cysteines: Probing ATP-modulated contacts in cysteine-substitution mutants of yeast DNA topoisomerase II", P.N.A.S., vol. 96, pp. 4862-4867, (1999).
Uchida, et al., "A novel epidermal browth factor-like molecule containing two follistatin modules stimulates tyrosine phosphorylation of erbB-4 in MKN28 gastric cancer cells", biochemical and biophysical research commincations, 266: 593-602, (1999).
Verhoeyen, Martine, et al., "Reshaping Human Antibodies: Grafting an Antilysozyme Activity", Science, vol. 239, pp. 1534-1536, Feb. 1988.
Weinstock et al., "CDNA Sequencing: A Means of Understanding Cellular Physiology" Current ( )Pinion in Biotechnology, 5(6)599-603 (1994), XP009091639, ISSN: 0958-1669.
Wu, et al., "Arming antibodies: prospects and challenges for immunoconjugates", Nature Biotechnology, vol. 23, No. 9, pp. 1137-1146, (2005).
Zhang, et al., "Complete disulfide bond assignment of a recombinant immunoglobulin G4 monoclonal antibody", Analytical Biochemistry, 311: 1-9, (2002).
Aerts et al. "Disparity between in vivo EGFR expression and 89Zr-labeled cetuximab uptake assessed with PET", J Nuclear Medicine 50(1):123-131, 2009.
All drugs online. Retrieved from the internet http:/ww.all-drugs-online.com/Drugs/Oncology/1377.aspx> retrieved Jan. 5, 2009.

Baca et al. "Antibody humanization using monovalent phage display", J. Biol. Chem, 272(16):10678-10684, 1997.
Biopharma [online] http://ww.biopharma.com/Samples/184.html. retrieved on Jan. 5, 2009.
Borjesson et al. "Performance of immuno-positron emisson tomography with zirconium-89-labeled chimeric monoclonal antibody U36 in the detection of lymph node metastases in head and neck cancer patients", Clin Cancer Res. 12:2133-2140, 2006.
Carter et al. "Humanization of an anti-p185HER2 antibody for human cancer therapy", Proc Natl Acad Sci USA 89(10):4285-4289, 1992.
CellTiter-Glo luminescent cell viability assay (Technical Bulletin No. 288), Madison, WI: Promega Corp. pp. 1-11, 2004.
Chang et al. "High-level secretion or human growth hormone by *Escherichia coli*", Gene 55:189-196, 1987.
Collaborative Computational Project No. 4 "The CCP4 Suite: programs for protein crystallography", Acta. Cryst. D50:760-763, 1994.
Corneillie et al. "Converting weak binders into infinite binders", Bioconjug Chem. 15:1389-1391, 2004.
Dennis et al. "Albumin binding as a general strategy for improving the pharmacokinetics of proteins", J. Biol. Chem. 277:35035-35043, 2002.
Dijkers et al. "Development and characterization of clinical-grade 89Zr-trastuzumab for HER2/neu immunoPET imaging", J Nucl. Med. 50:974-981, 2009.
Eigenbrot et al. "X-ray structures of the antigen-binding domains from three variants of humanized anti-p185HERS antibody 4D5 and comparison with molecular modeling", J Mol Biol. 229:969-995, 1993.
Gagnon et al. "High-throughput in vivo screening of targeted molecular imaging agents", Proc Natl Acad. Sci. USA 106:17904-17909, 2009.
Gerstner et al. "Sequence plasticity in the antigen-binding site of a therapeutic anti-HER2 antibody", J Mol Biol. 321(5):851-862, 2002.
Gill et al. "A modular platform for the rapid site-specific radiolabeling of proteins with 18F exemplified by quantitative positron emission tomography of human epidermal growth factor receptor 2", J Med Chem. 52(19):5816-5825, 2009.
Govindan et al. "Deferoxamine as a chelator for 67Ga in the preparation of antibody conjugates", Nuc. Med Biol. 32(5):513-519, 2005.
Hafner et al. "Noncompetitive immunoassay of small analytes at the femtomoloar level by affinity probe capillary electrophoresis: direct analysis of digoxin using a uniform-labeled scFv imunoreagent", Anal. Chem. 72:5579-5586, 2000.
Hausner et al. "Use of a peptide derived from foot-and-mouth disease virus for the noninvasive imaging of human cancer: generation and evaluation of 4-[18F]fluorobenzoyl A20FMDV2 for in vivo imaging of integrin alphavbeta6 expression with positron emisson tomography", Cancer Res. 67:7833-7840, 2007.
Hausner et al. "Targeted in vivo imaging of integrin alphavbeta6 with an improved radiotracer and its relevance in a pancreatic tumor model", Cancer Res. 69:5843-5850, 2009.
Hausner et al. "In vivo positron emission tomography (PET) imaging with an alphavbeta6 specific peptide radiolabeled using 18F-"click" chemistry: evaluation and comparison with the corresponding 4-[18F] fluorobenzoyl- and 2-[18F] fluoropropionyl-peptides", J Med. Chem. 51:5901-5904, 2008.
Ho et al. "Site-directed mutagenesis by overlap extension using the polymerase chain reaction", Gene 77(1):51-59, 1989.
Ito et al. "A general method for introducing a series of mutations into cloned DNA using the polymerase chain reaction", Gene 102(1):67-70, 1991.
Junutula et al. "Site-specific conjugation of a cytotoxic drug to an antibody improves the therapeutic index", Nat Biotechnol. 26(8):925-932, 2008.
Kabat et al. "Sequences of proteins of immunological interest", US Department of Health and Human Services, Public Health Service, NIH 4th Ed. pp. 160 and 294, 1987.
King et al. "Facile synthesis of maleimide bifunctional linkers", Tetrahedron Letters 43:1987-1990, 2002.
Kumaresan et al. "Evaluation of ketone oxime method for developing therapeutic on-demand cleavable immunoconjugates", Bioconjug Chem. 19(6):1313-1318, 2008.

(56) References Cited

OTHER PUBLICATIONS

Lewis et al. "Maleimidocysteineamido-DOTA derivatives: new reagents for radiometal chelate conjugation to antibody sulfhydryl groups undergo pH-dependent cleavage reactions", Bioconjug Chem 9(1):72-86, 1998.

Liu, S. "Bifunctional coupling agents for radiolabeling of biomolecules and target-specific delivery of metallic radionuclides", Adv Drug Deliv Rev. 60(12):1347-1370, 2008.

Lowman, HB "Phage display of peptide libraries on protein scaffolds", Methods Mol Biol. 87:249-264, 1998.

Lund et al. "Expression and characterization of truncated forms of humanized L243 IgG1. Architectural features can influence synthesis of its oligosaccharide chains and affect superoxide production triggered through human Fcgamma receptor 1", Eur J Biochem 267:7246-7257, 2000.

MacCallum et al. "Antibody-antigen interactions: contact analysis and binding site topography", J Mol Biol. 262(5):732-745, 1996.

Meijs et al. "A facile method for the labeling of proteins with zirconium isotopes", Nucl Med Biol.23(4):439-448, 1996.

Meijs et al. "Zirconium-labeled monoclonal antibodies and their distribution in tumor-bearing nude mice", J Nucl Med 38(1):112-118, 1997.

Miller, MJ. "Syntheses and therapeutic potential of hydroxamic acid based siderophores and analogues", Chem. Rev. 89:1563-1579, 1989.

Nagengast et al. "In vivo VEGF imaging with radiolabeled bevacizumab in a human ovarian tumor xenograft", J Nucl Med. 48(8):1313-1319, 2007.

Olafsen et al. "Characterization of engineered anti-p185HER-2 (scFv-CH3)2 antibody fragments (minibodies) for tumor targeting", Protein Eng Des Sel. 17:315-323, 2004.

Perk et al. "Preparation and evaluation of (89)Zr-Zevalin for monitoring of (90)Y-Zevalin biodistribution with positron emission tomography", Eur J Nucl Med Mol Imaging 33(11):1337-1345, 2006.

Perk et al. "Quantitative PET imaging or Met-expressing human cancer xenografts with 89Zr-labelled monoclonal antibody DN30", Eur J Nucl Med Mol Imaging 35:1857-1867, 2008.

Perk et al. "(89) Zr as a PET surrogate radioisotope for scouting biodistribution of the therapeutic radiometals (90)Y and (177)Lu in tumor-bearing nude mice after coupling to the internalizing antibody cetuximab", J Nucl Med. 46:1898-1906, 2005.

Renard et al. "Deriving topological constraints from functional data for the design or reagentless fluorescent immunosensors", J Mol Biol. 326(1):167-175, 2003.

Roux et al. "Comparisons of the ability of human IgG3 hinge mutants, IgM, IgE, and IgA2 to form small immune complexes: a role for flexibility and geometry", J Immunol. 161:4083-4090, 1998.

Rudikoff et al. "Single amino acid substitution altering antigen-binding specificity", Proc. Natl. Acad. Sci. USA 79:1979-1983, 1982.

Schelte et al. "Differential reactivity of maleimide and bromoacetyl functions with thiols: application to the preparation of liposomal diepitope constructs", Bioconjug Chem. 11(1):118-123, 2000.

Shopes, B. "A genetically engineered human IgG with limited flexibility fully initiates cytolysis via complement", Mol Immunol. 30(6)603-609, 1993.

Singh et al. "Labeling of antibodies by in situ modification of thiol groups generated from selenol-catalyzed reduction of native disulfide bonds", Anal Biochem. 304(2):147-156, 2002.

Stimmel et al. "Site-specific conjugation on serine right-arrow cysteine variant monoclonal antibodies", J Biol. Chem. 275:30445-30450, 2000.

Sun et al. "Enabling ScFvs as multi-drug carriers: a dendritic approach", Bioorg Med Chem 11(8):1761-1768, 2003.

Sun et al. "Syntheses of dendritic linkers containing chlorambucil residues for the preparation of antibody-multidrug immunoconjugates", Bioorg Med Chem Lett. 12(16):2213-2215, 2002.

Tartis et al. "Dynamic microPET imaging of ultrasound contrast agents and lipid delivery", J Control Release 131(3):161-166, 2008.

Tinianow, et al. "Site-specifically 89Zr-labeled monoclonal antibodies for immunoPET", Nucl Med Biol. 37(3):289-297, 2010.

Trail et al. "Monoclonal antibody drug immunoconjugates for targeted treatment of cancer", Cancer Immunol. Immunother. 52(5):328-337, 2003.

Verel et al. "Quantitative 89Zr immuno-PET for in vivo scouting of 90Y-labeled monoclonal antibodies in xenograft-bearing nude mice", J Nucl Med 44(10):1663-1670, 2003.

Verel et al. "89Zr immuno-PET: comprehensive procedures for the production of 89Zr-labeled monoclonal antibodies", J Nucl Med. 44(8):1271-1281, 2003.

Vosjan et al. "Conjugation and radiolabeling of monoclonal antibodies with zirconium-89 for PET imaging using the bifunctional chelate p-isothiocyanatobenzyl-desferrioxamine", Nat Protoc. 5(4):739-743, 2010.

Wu et al. "Humanization of a murine monoclonal antibody by simultaneous optimization of framework and CDR residues", J Mol. Biol. 294(1):151-162, 1999.

* cited by examiner

Human TMEFF2#19 (Pr1) anti-TENB2 Ab heavy chain amino acid sequence (signal peptide is underlined):

<u>MAVLGLLLCLVTFPSCVLSD</u>VQLQESGPGLVKPSETLSLTCAVSGYSITSGYYWSWIRQPPGKGLEWMGFIS
YDGSNKYNPSLKNRITISRDTSKNQFSLKLSSVTAADTAVYYCARGLRRGDYSMDYWGQGTLVTVSSASTKG
PSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVLDSDGSFFLYSKL
TVDKSRWQQGNVFSCSVMHEALHNHYTQKSLSLSPGK                SEQ ID NO:1

Human TMEFF2#19 (Pr1) anti-TENB2 Ab light chain amino acid sequence (signal peptide is underlined):

<u>MDFQVQIFSFLLISASVIMSRG</u>DIQMTQSPSSLSASVGDRVTITCKASQNVTAVAWYQQKPGKAPKLLIYSASNRHT
GVPSRFSGSGSGTDFTLTISSLQPEDFATYYCQQYSSYPFTFGGGTKVEIKRTVAAPSVFIFPPSDEQLKSGTASVVC
LLNNFYPREAKVQWKVDNALQSGNSQESVTEQDSKDSTYSLSSTLTLSKADYEKHKVYACEVTHQGLSSPVTKSFNRG
EC                SEQ ID NO:2

FIG. 1

A121C thio hu TMEFF2#19 (Pr1) heavy chain amino acid sequence (signal peptide is underlined):

MAVLGLLLCLVTFPSCVLSDVQLQESGPGLVKPSETLSLTCAVSGYSITSGYYWSWIRQPPGKGLEWMGFI
SYDGSNKYNPSLKNRITISRDTSKNQFSLKLSSVTAADTAVYYCARGLRRGDYSMDYWGQGTLVTVSSCST
KGPSVFPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK                SEQ ID NO:3

A121C thio hu TMEFF2#19 (Pr1) light chain amino acid sequence (signal peptide is underlined):

MDFQVQIFSFLLISASVIMSRGDIQMTQSPSSLSASVGDRVTITCKASQNVVTAVAWYQQKPGKAPKLLIYSASNRH
TGVPSRFSGSGSGTDFTLTISSLQPEDFATYYCQQYSSYPFTFGGGTKVEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGLSSPVTKSF
NRGEC                                                     SEQ ID NO:2

Thio-anti-TENB2 heavy chain amino acid sequence (signal sequence is underlined). Cysteine substitution is at Ala-121 residue in the heavy chain

FIG. 2

```
Hu4D5Light    1 DIQMTQSPSSLSASVGDRVTITCRASQDVNTAVAWYQQKPGKAPKLLIYS 50
PR1-LC        1 DIQMTQSPSSLSASVGDRVTITCKASQNVTAVAWYQQKPGKAPKLLIYS 50
                                            15

Hu4D5Light   51 ASFLYSGVPSRFSGSRSGTDFTLTISSLQPEDFATYYCQQHYTTPPTFGQ 100
PR1-LC       51 ASNRHTGVPSRFSGSGSGTDFTLTISSLQPEDFATYYCQQYSSYPFTFGG 100

Hu4D5Light  101 GTKVEIKRTVAAPSVFIFPPSDEQLKSGTASVVCLLNNFYPREAKVQWKV 150
PR1-LC      101 GTKVEIKRTVAAPSVFIFPPSDEQLKSGTASVVCLLNNFYPREAKVQWKV 150
                            110         121   127

Hu4D5Light  151 DNALQSGNSQESVTEQDSKDSTYSLSSTLTLSKADYEKHKVYACEVTHQG 200
PR1-LC      151 DNALQSGNSQESVTEQDSKDSTYSLSSTLTLSKADYEKHKVYACEVTHQG 200
                                 168

Hu4D5Light  201 LSSPVTKSFNRGEC 214
PR1-LC      201 LSSPVTKSFNRGEC 214
                    205
```

The numbering denotes for PR1 (anti-TENB2) light chain according to sequential numbering

FIG. 3

```
Hu4D5Heavy   1   E V Q L V E S G G G L V Q P G G S L R L S C A A S G F N I K D T Y I - H W V R Q A P G K G L E W V A   49
PR1-HC       1   D V Q L Q E S G P G L V K P S E T L S L T C A V S G Y S I T S G Y Y W S W I R Q P P G K G L E W M G   50
                     5                                     23

Hu4D5Heavy   50  R I Y P T N G Y T R Y A D S V K G R F T I S A D T S K N T A Y L Q M N S L R A E D T A V Y Y C S R W   99
PR1-HC       51  F I - S Y D G S N K Y N P S L K N R I T I S R D T S K N Q F S L K L S S V T A A D T A V Y Y C A R G   99
                                                                                          88

Hu4D5Heavy   100 G G D G F Y A M P Y W G Q G T L V T V S S A S T K G P S V F P L A P S S K S T S G G T A A L G C L V   149
PR1-HC       100 L R R G D Y S M D Y W G Q G T L V T V S S A S T K G P S V F P L A P S S K S T S G G T A A L G C L V   149
                             119 121 123

Hu4D5Heavy   150 K D Y F P E P V T V S W N S G A L T S G V H T F P A V L Q S S G L Y S L S S V V T V P S S S L G T Q   199
PR1-HC       150 K D Y F P E P V T V S W N S G A L T S G V H T F P A V L Q S S G L Y S L S S V V T V P S S S L G T Q   199

Hu4D5Heavy   200 T Y I C N V N H K P S N T K V D K K V E P K S C D K T H T C P P C P A P E L L G G P S V F L F P P K   249
PR1-HC       200 T Y I C N V N H K P S N T K V D K K V E P K S C D K T H T C P P C P A P E L L G G P S V F L F P P K   249

Hu4D5Heavy   250 P K D T L M I S R T P E V T C V V V D V S H E D P E V K F N W Y V D G V E V H N A K T K P R E E Q Y   299
PR1-HC       250 P K D T L M I S R T P E V T C V V V D V S H E D P E V K F N W Y V D G V E V H N A K T K P R E E Q Y   299
                                                                           285

Hu4D5Heavy   300 N S T Y R V V S V L T V L H Q D W L N G K E Y K C K V S N K A L P A P I E K T I S K A K G Q P R E P   349
PR1-HC       300 N S T Y R V V S V L T V L H Q D W L N G K E Y K C K V S N K A L P A P I E K T I S K A K G Q P R E P   349

Hu4D5Heavy   350 Q V Y T L P P S R E E M T K N Q V S L T C L V K G F Y P S D I A V E W E S N G Q P E N N Y K T T P P   399
PR1-HC       350 Q V Y T L P P S R D E L T K N Q V S L T C L V K G F Y P S D I A V E W E S N G Q P E N N Y K T T P P   399
                                                             378

Hu4D5Heavy   400 V L D S D G S F F L Y S K L T V D K S R W Q Q G N V F S C S V M H E A L H N H Y T Q K S L S L S P G   449
PR1-HC       400 V L D S D G S F F L Y S K L T V D K S R W Q Q G N V F S C S V M H E A L H N H Y T Q K S L S L S P G   449
                         403

Hu4D5Heavy   450 K   450
PR1-HC       450 K   450
```

The numbering denotes for PR1 (anti-TENB2) heavy chain according to sequential numbering

FIG. 4

Immunohistochemistry: TENB2 expression in human prostate tumors
Top and bottom panels are from human prostate explant models,
PC3TENB2 medium stable cell line with vector control and prostate tumor,
respectively.

Internalization of TENB2 monoclonal antibody (Mab) on PC3TENB2Medium cell line and Lucap 70 tumor.

AntiTENB2 on PC3TENB2 medium with 2hrs treatment at 37°C

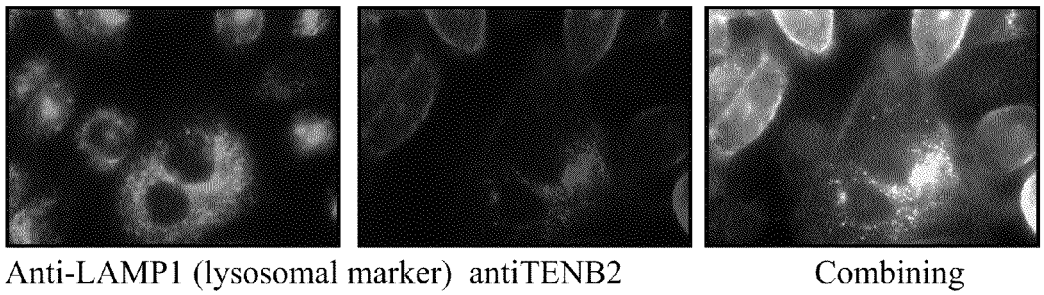

Anti-LAMP1 (lysosomal marker)  antiTENB2                Combining

AntiTENB2 on LuCaP70 with 2 and 18hrs at 37°C incubation

AntiTENB2 AB internalized in PC3TENB2Medium cells faster than LuCaP70 tumor. AntiTENB2 AB was internalized more than 60% on LuCap70 cells at 18 hours.

FIG. 9

Cell killing Assay on PC3TENB2 Medium cells with conventional anti-TENB2 and thio-anti-TENB2 ADCs

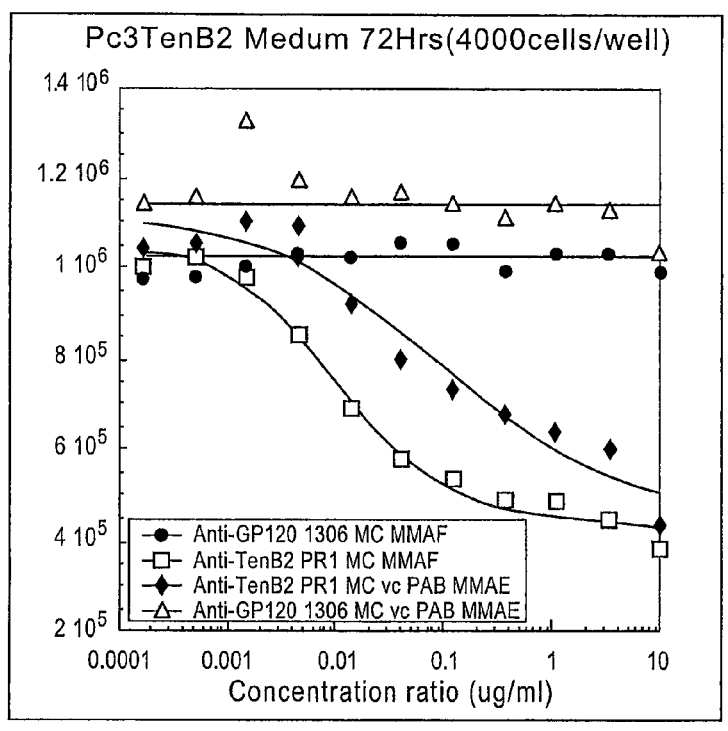

Conventional anti-TENB2-ADCs

TENB2 -expressing PC3 cells was killed by conventional or thio-anti-TENB2 ADCs. The PC3 cell lines stably over expressing TENB2 (PC3TENB2 Medium) was treated with increasing concentrations of conventional, Thio-anti-TENB2ADCs and control ADCs. Cell viability was measured after 3 days

FIG. 11A

Different level TENB2 protein expression levels observed on LuCaP transplant tumors, in which LuCaP77 is highest and LuCaP35V is lowest This data is consistent to our Taqman data on those tumor lines (data not show in here)

Toxicology studies with anti-TENB2 ADCs in rats and cynomolgus monkeys (both binding species) were performed and revealed no target-related toxicities in normal tissues and non-target-dependent toxicities at doses substantially higher than the anticipated efficacious dose Anti-TENB2-vc-MMAE and –MC-MMAF in cynomolgus monkeys:

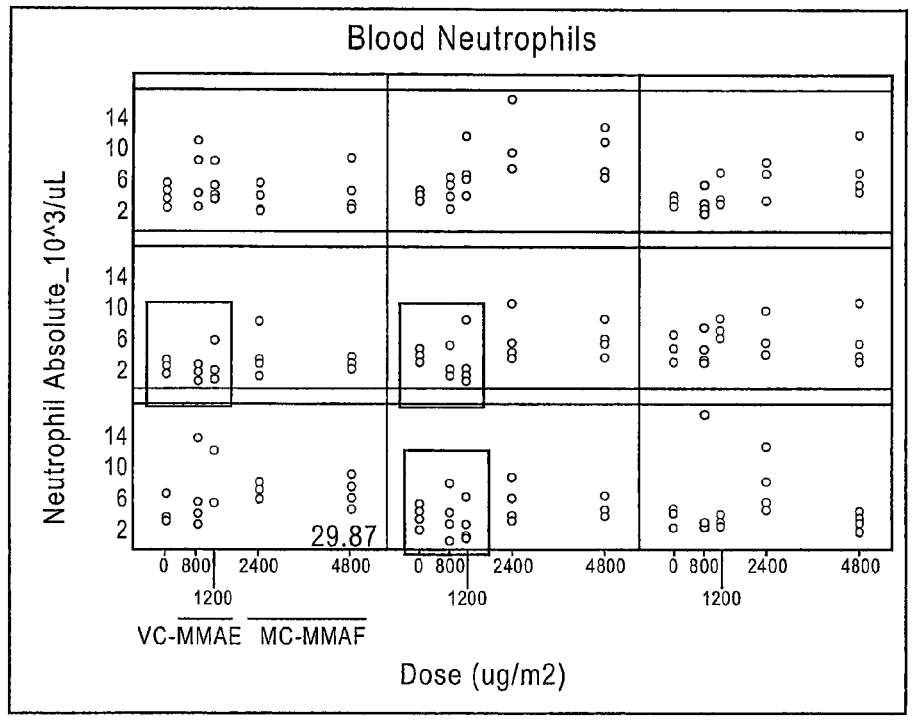

Groups: 1 Vehicle, 2 Naked PR1, 3 and 4 PR1vcE (800,1200 ug/m$^2$),
5 and 6 PR1MC F (2400, 4800 ug/m$^2$)
Note: 800ug/m$^2$ equivalent to 8.7mg/kg.

Toxicology studies with anti-TENB2 ADCs in rats and cynomolgus monkeys (both binding species) were performed and revealed no target-related toxicities in normal tissues and non-target-dependent toxicities at doses substantially higher than the anticipated efficacious dose

FIG. 17A

Thio-anti-TENB2-vc-MMAE compared with anti-TENB2-vc-MMAE in rats

Thio-anti-TENB2-vc-MMAE: improvement in neutrophil counts and AST levels

CYSTEINE ENGINEERED ANTI-TENB2 ANTIBODIES AND ANTIBODY DRUG CONJUGATES

CROSS REFERENCE TO RELATED APPLICATIONS

This application is a non-provisional application filed under 37 CFR 1.53(b)(1), claiming priority under 35 USC 119(e) to provisional application No. 60/981,411 filed Oct. 19, 2007, the contents of which are incorporated herein by reference.

FIELD OF THE INVENTION

The invention relates generally to antibodies engineered with reactive cysteine residues and more specifically to antibodies with therapeutic or diagnostic applications. The cysteine engineered antibodies may be conjugated with chemotherapeutic drugs, toxins, affinity ligands such as biotin, and detection labels such as fluorophores. The invention also relates to methods of using antibodies and antibody-drug conjugate compounds for in vitro, in situ, and in vivo diagnosis or treatment of mammalian cells, or associated pathological conditions.

BACKGROUND OF THE INVENTION

Antibody therapy has been established for the targeted treatment of patients with cancer, immunological and angiogenic disorders. Transmembrane or otherwise tumor-associated polypeptides specifically expressed on the surface of cancer cells as compared to normal, non-cancerous cell(s) have been identified as cellular targets for cancer diagnosis and therapy with antibodies. Identification of such tumor-associated cell surface antigen polypeptides, i.e. tumor associated antigens (TAA), allows specific targeting of cancer cells for destruction via antibody-based therapies.

The use of antibody-drug conjugates (ADC), i.e. immunoconjugates, for the local delivery of cytotoxic or cytostatic agents, i.e. drugs to kill or inhibit tumor cells in the treatment of cancer (Lambert, J. (2005) Curr. Opinion in Pharmacology 5:543-549; Wu et al (2005) Nature Biotechnology 23(9):1137-1146; Payne, G. (2003) Cancer Cell 3:207-212; Syrigos and Epenetos (1999) Anticancer Research 19:605-614; Niculescu-Duvaz and Springer (1997) Adv. Drug Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al (1986) Lancet pp. (Mar. 15, 1986): 603-05; Thorpe, (1985) "Antibody Carriers Of Cytotoxic Agents In Cancer Therapy: A Review," in Monoclonal Antibodies '84: Biological And Clinical Applications, A. Pinchera et al (ed.s), pp. 475-506). Efforts to improve the therapeutic index, i.e. maximal efficacy and minimal toxicity of ADC have focused on the selectivity of polyclonal (Rowland et al (1986) Cancer Immunol. Immunother., 21:183-87) and monoclonal antibodies (mAbs) as well as drug-linking and drug-releasing properties (Lambert, J. (2005) Curr. Opinion in Pharmacology 5:543-549). Drug moieties used in antibody drug conjugates include bacterial protein toxins such as diphtheria toxin, plant protein toxins such as ricin, small molecules such as auristatins, geldanamycin (Mandler et al (2000) J. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al (1996) Proc. Natl. Acad. Sci. USA 93:8618-8623), calicheamicin (Lode et al (1998) Cancer Res. 58:2928; Hinman et al (1993) Cancer Res. 53:3336-3342), daunomycin, doxorubicin, methotrexate, and vindesine (Rowland et al (1986) supra). The drug moieties may affect cytotoxic and cytostatic mechanisms including tubulin binding, DNA binding, or topoisomerase inhibition. Some cytotoxic drugs tend to be inactive or less active when conjugated to large antibodies or protein receptor ligands.

The auristatin peptides, auristatin E (AE) and monomethylauristatin (MMAE), synthetic analogs of dolastatin (WO 02/088172), have been conjugated as drug moieties to: (i) chimeric monoclonal antibodies cBR96 (specific to Lewis Y on carcinomas); (ii) cAC10 which is specific to CD30 on hematological malignancies (Klussman, et al (2004), Bioconjugate Chemistry 15(4):765-773; Doronina et al (2003) Nature Biotechnology 21(7):778-784; Francisco et al (2003) Blood 102(4):1458-1465; US 2004/0018194; (iii) anti-CD20 antibodies such as rituxan (WO 04/032828) for the treatment of CD20-expressing cancers and immune disorders; (iv) anti-EphB2R antibody 2H9 for treatment of colorectal cancer (Mao et al (2004) Cancer Research 64(3):781-788); (v) E-selectin antibody (Bhaskar et al (2003) Cancer Res. 63:6387-6394); (vi) trastuzumab (HERCEPTIN®, US 2005/0238649), and (vi) anti-CD30 antibodies (WO 03/043583). Variants of auristatin E are disclosed in U.S. Pat. No. 5,767,237 and U.S. Pat. No. 6,124,431. Monomethyl auristatin E conjugated to monoclonal antibodies are disclosed in Senter et al, Proceedings of the American Association for Cancer Research, Volume 45, Abstract Number 623, presented Mar. 28, 2004. Auristatin analogs MMAE and MMAF have been conjugated to various antibodies (US 2005/0238649).

Conventional means of attaching, i.e. linking through covalent bonds, a drug moiety to an antibody generally leads to a heterogeneous mixture of molecules where the drug moieties are attached at a number of sites on the antibody. For example, cytotoxic drugs have typically been conjugated to antibodies through the often-numerous lysine residues of an antibody, generating a heterogeneous antibody-drug conjugate mixture. Depending on reaction conditions, the heterogeneous mixture typically contains a distribution of antibodies with from 0 to about 8, or more, attached drug moieties. In addition, within each subgroup of conjugates with a particular integer ratio of drug moieties to antibody, is a potentially heterogeneous mixture where the drug moiety is attached at various sites on the antibody. Analytical and preparative methods may be inadequate to separate and characterize the antibody-drug conjugate species molecules within the heterogeneous mixture resulting from a conjugation reaction. Antibodies are large, complex and structurally diverse biomolecules, often with many reactive functional groups. Their reactivities with linker reagents and drug-linker intermediates are dependent on factors such as pH, concentration, salt concentration, and co-solvents. Furthermore, the multistep conjugation process may be nonreproducible due to difficulties in controlling the reaction conditions and characterizing reactants and intermediates.

Cysteine thiols are reactive at neutral pH, unlike most amines which are protonated and less nucleophilic near pH 7. Since free thiol (RSH, sulfhydryl) groups are relatively reactive, proteins with cysteine residues often exist in their oxidized form as disulfide-linked oligomers or have internally bridged disulfide groups. Extracellular proteins generally do not have free thiols (Garman, 1997, Non-Radioactive Labelling: A Practical Approach, Academic Press, London, at page 55). Antibody cysteine thiol groups are generally more reactive, i.e. more nucleophilic, towards electrophilic conjugation reagents than antibody amine or hydroxyl groups. Cysteine residues have been introduced into proteins by genetic engineering techniques to form covalent attachments to ligands or to form new intramolecular disulfide bonds (Better et al (1994) J. Biol. Chem. 13:9644-9650; Bernhard et al (1994) Bioconjugate Chem. 5:126-132; Greenwood et al (1994) Therapeutic Immunology 1:247-255; Tu et al (1999) Proc. Natl. Acad. Sci. USA 96:4862-4867; Kanno et al (2000) J. of Biotechnology, 76:207-214; Chmura et al (2001) Proc. Nat. Acad. Sci. USA 98(15):8480-8484; U.S. Pat. No. 6,248,564). However, engineering in cysteine thiol groups by the mutation of various amino acid residues of a protein to cysteine amino acids is potentially problematic, particularly in the case of unpaired (free Cys) residues or those which are relatively accessible for reaction or oxidation. In concentrated solutions of the protein, whether in the periplasm of *E. coli*, culture supernatants, or partially or completely purified protein, unpaired Cys residues on the surface of the protein can pair and oxidize to form intermolecular disulfides, and hence protein dimers or multimers. Disulfide dimer formation renders the new Cys unreactive for conjugation to a drug, ligand, or other label. Furthermore, if the protein oxidatively forms an intramolecular disulfide bond between the newly engineered Cys and an existing Cys residue, both Cys thiol groups are unavailable for active site participation and interactions. Furthermore, the protein may be rendered inactive or non-specific, by misfolding or loss of tertiary structure (Zhang et al (2002) Anal. Biochem. 311:1-9).

Cysteine-engineered antibodies have been designed as FAB antibody fragments (thioFab) and expressed as fulllength, IgG monoclonal (thioMab) antibodies (US 2007/0092940, the contents of which are incorporated by reference). ThioFab and ThioMab antibodies have been conjugated through linkers at the newly introduced cysteine thiols with thiol-reactive linker reagents and drug-linker reagents to prepare antibody drug conjugates (Thio ADC).

TENB2 is a tumor associated antigen polypeptide (also known as PR1), and the TENB2 protein contains 2 follistatin-like domains and a conserved EGF-like domain. The gene encoding the protein was first characterized from a human brain cDNA library (see Uchida, et al. (1999) Biochem. Biophys. Res. Commun. 266:593-602), and later isolated from a human fetal brain cDNA library (see Horie, et al. (2000) Genomics 67:146-152). See also, e.g., Online Mendelian Inheritance in Man, number 605734; Unigene Cluster Hs. 22791; LocusLink 23671; and other linked sites. TENB2 has been referred to as PR1, tomoregulin, TR, hyperplastic polyposis gene 1, HPP1, and TMEFF2. It's nucleic acid sequence can be identified by ATCC Accession Nos. AF264150, AB004064, AB017269, and AF179274; and it's amino acid sequence can be identified by ATCC Accession Nos. AAF91397, BAA90820, BAA87897, and AAD55776. TENB2's UniGene Cluster identification number is hs.22791, Locuslink identification number is 23671, and OMIM identification number is 605734.

The gene has also been implicated in certain cancerous conditions. Young, et al. (2001) Proc. Nat'l Acad. Sci. USA 98:265-270 reported expression in colorectal polyps. Glynne-Jones, et al. (2001) Int. J. Cancer 94:178-184 reported it as a marker for prostate cancer.

Due to its overexpression in certain human tumors, the TENB2 polypeptide and the nucleic acid encoding that polypeptide are targets for quantitative and qualitative comparisons among various mammalian tissue samples. The unique expression profiles of TENB2 polypeptide, and the nucleic acid encoding that polypeptide, can be exploited for the diagnosis and therapeutic treatment of certain types of cancerous tumors in mammals.

Recently, certain anti-TENB2 antibodies, including anti-TMEFF2 antibody #19, were disclosed and shown to be internalized and useful for the treatment of proliferative conditions of the prostate, including, e.g., benign prostate hyperplasia and prostate cancer (PCT/US03/07209; U.S. Ser. No. 10/383,447, filed Mar. 7, 2003, now U.S. Pat. No. 7,288, 248; Vinay et al., "Antibodies Against Cancer Antigen TMEFF2 and Uses Thereof" the contents of which are incorporated by reference).

SUMMARY

In one aspect, the invention includes a cysteine engineered anti-TENB2 antibody comprising one or more free cysteine amino acids and a sequence selected from SEQ ID NOS: 8-23. The cysteine engineered anti-TENB2 antibody may bind to a TENB2 polypeptide. Tumor-associated antigens (TAA) such as TENB2 polypeptides can be prepared for use in generating cysteine engineered antibodies using methods and information which are well known in the art, and for example in PCT/US03/07209 (U.S. Pat. No. 7,288,248). The cysteine engineered anti-TENB2 antibody may be prepared by a process comprising replacing one or more amino acid residues of a parent anti-TENB2 antibody by cysteine.

The one or more free cysteine amino acid residues of the cysteine engineered anti-TENB2 antibody are located in a light chain or a heavy chain.

In one aspect, the invention includes a method of determining the presence of a TENB2 protein in a sample suspected of containing said protein, said method comprising exposing said sample to a cysteine engineered anti-TENB2 antibody and determining binding of said antibody to said TENB2 protein in said sample, wherein binding of the antibody to said protein is indicative of the presence of said protein in said sample.

Cysteine engineered anti-TENB2 antibodies may be used as naked antibodies (unconjugated to a drug or label moiety) or as antibody-drug conjugates (ADC). The cysteine engineered anti-TENB2 antibody may be covalently attached to an auristatin drug moiety whereby an antibody drug conjugate is formed. The antibody-drug conjugate may comprising a cysteine engineered anti-TENB2 antibody (Ab), and an auristatin drug moiety (D) wherein the cysteine engineered anti-TENB2 antibody is attached through one or more free cysteine amino acids by a linker moiety (L) to D; the compound having Formula I:

Ab-(L-D)$_p$      I where p is 1, 2, 3, or 4. Auristatin drug moieties include MMAE and MMAF.

An aspect of the invention is an assay for detecting cancer cells comprising: (a) exposing cells to an antibody-drug conjugate compound; and (b) determining the extent of binding of the antibody-drug conjugate compound to the cells.

An aspect of the invention is a pharmaceutical formulation comprising the antibody drug conjugate, and a pharmaceutically acceptable diluent, carrier or excipient.

An aspect of the invention is a method of inhibiting cellular proliferation comprising treating mammalian tumor cells in a cell culture medium with an antibody-drug conjugate compound, whereby proliferation of the tumor cells is inhibited.

An aspect of the invention is a method of treating cancer comprising administering to a patient the pharmaceutical formulation. The patient may be administered a chemotherapeutic agent in combination with the antibody-drug conjugate compound.

An aspect of the invention is an article of manufacture comprising the pharmaceutical formulation, a container; and a package insert or label indicating that the compound can be used to treat cancer characterized by the overexpression of a TENB2 polypeptide.

An aspect of the invention is a method for making a Formula I antibody drug conjugate compound comprising the steps of: (a) reacting an engineered cysteine group of the cysteine engineered antibody with a linker reagent to form antibody-linker intermediate Ab-L; and (b) reacting Ab-L with an activated drug moiety D; whereby the antibody-drug conjugate is formed; or comprising the steps of: (c) reacting a nucleophilic group of a drug moiety with a linker reagent to form drug-linker intermediate D-L; and (d) reacting D-L with an engineered cysteine group of the cysteine engineered antibody; whereby the antibody-drug conjugate is formed.

BRIEF DESCRIPTION OF THE DRAWINGS

FIG. 1 shows the Heavy Chain sequence: SEQ ID NO:1, and Light Chain sequence: SEQ ID NO:2 of humanized anti-TENB2 antibody, hu TMEFF2#19.

FIG. 2 shows the Heavy Chain sequence: SEQ ID NO:3, and Light Chain sequence: SEQ ID NO:2 of a humanized cysteine engineered anti-TENB2 antibody, A121C thio hu TMEFF2#19. Signal sequence is not included in the sequential numbering of anti-TENB2 antibody.

FIG. 3 shows alignment of humanized trastuzumab light chain (HuTMAb-LC, SEQ ID NO:4) and hu TMEFF2#19 light chain (SEQ ID NO:5). The numbering follows the sequential numbering convention.

FIG. 4 shows alignment of humanized trastuzumab heavy chain (HuTMAb-HC, SEQ ID NO:6), and hu TMEFF2#19 heavy chain (SEQ ID NO:7). The numbering follows the sequential numbering convention.

FIG. 9 shows internalization of TENB2 monoclonal antibody (Mab) on PC3TENB2 Medium cell line and LuCaP 70 tumor.

DETAILED DESCRIPTION OF EXEMPLARY EMBODIMENTS

Figure 5:
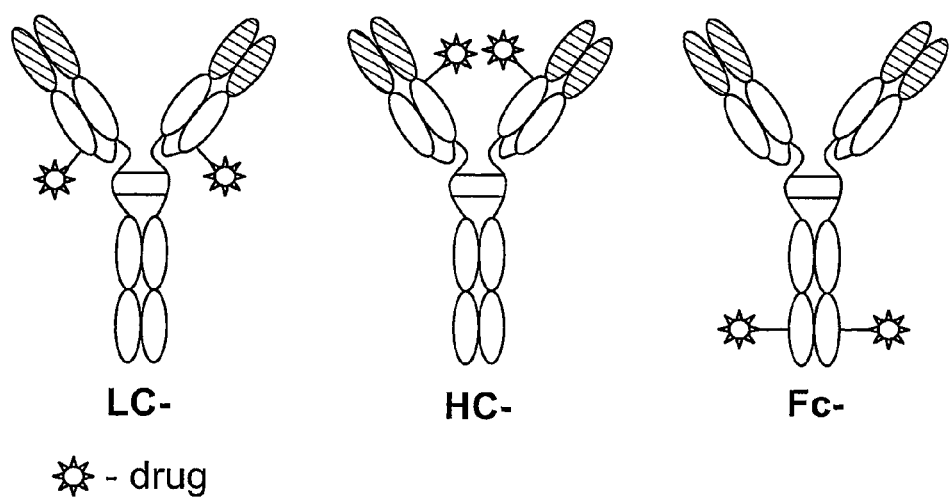
FIG. 5 shows depictions of cysteine engineered anti-TENB2 antibody drug conjugates (ADC) where a drug moiety is attached to an engineered cysteine group in: the light chain (LC-ADC); the heavy chain (HC-ADC); and the Fc region (Fc-ADC).

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

DEFINITIONS

Unless defined otherwise, technical and scientific terms used herein have the same meaning as commonly understood by one of ordinary skill in the art to which this invention belongs, and are consistent with: Singleton et al (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) Jour. of Immunology 170:4854-4861). Antibodies may be murine, human, humanized, chimeric, or derived from other species. An antibody is a protein that is capable of recognizing and binding to a specific antigen (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species such as human, murine, or rabbit. For the structure and properties of the different classes of antibodies, see, e.g., *Basic and Clinical Immunology,* 8th edition, Daniel P. Stites, Abba I. Terr and Tristram G. Parslow (eds.), Appleton & Lange, Norwalk, Conn., 1994, page 71 and Chapter 6.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; minibodies (U.S. Pat. No. 5,641,870, Example 2; Zapata et al (1995) Protein Eng. 8(10): 1057-1062); Olafsen et al (2004) Protein Eng. Design & Sel. 17(4):315-323), fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (see for example: U.S. Pat. No. 4,816,567; U.S. Pat. No. 5,807,715). In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, (1986) *Monoclonal Antibodies: Principles and Practice,* pp. 59-103 Academic Press). The monoclonal antibodies may also be isolated from phage antibody libraries using the techniques described in Clackson et al (1991) Nature, 352:624-628; Marks et al (1991) J. Mol. Biol., 222:581-597.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., Proc. Natl. Acad. Sci. USA, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape etc) and human constant region sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all, or substantially all, of the FRs are those of a human immunoglobulin sequence. The humanized antibody optionally also will comprise at least a portion of an immunoglobulin constant region (Fc), typically that of a human immunoglobulin. The Fc fragment comprises the carboxy-terminal portions of both H chains held together by disulfides. The effector functions of antibodies are determined by sequences in the Fc region, which region is also the part recognized by Fc receptors (FcR) found on certain types of cells (Jones et al (1986) Nature 321:522-525; Riechmann et al (1988) Nature 332:323-329; Presta, (1992) Curr. Op. Struct. Biol. 2:593-596; Verhoeyen et al (1988) Science, 239: 1534-1536; Sims et al (1993) J. Immunol. 151:2296; Chothia et al (1987) J. Mol. Biol., 196:901). Other methods use a particular framework region derived from the consensus sequence of all human antibodies of a particular subgroup of light or heavy chains (Carter et al (1992) Proc. Natl. Acad. Sci. USA, 89:4285; Presta et al (1993) J. Immunol. 151: 2623).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Transgenic animals (e.g., mice) are available that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge (Jakobovits et al (1993) Proc. Natl. Acad. Sci. USA, 90:2551; Jakobovits et al (1993) Nature, 362:255-258; Bruggemann et al (1993) Year in Immuno. 7:33; U.S. Pat. No. 5,545,806; U.S. Pat. No. 5,569,825; U.S. Pat. No. 5,591,669; U.S. Pat. No. 5,545,807; and WO 97/17852.

An "affinity matured" antibody is one with one or more alterations in one or more CDRs thereof which result in an improvement in the affinity of the antibody for antigen, compared to an antibody which does not possess those alteration(s). Preferred affinity matured antibodies will have nanomolar or even picomolar affinities for the target antigen. Affinity matured antibodies are produced affinity maturation by VH and VL domain shuffling (Marks et al (1992) Bio/Technology 10:779-783), or random mutagenesis of CDR and/or framework residues (Barbas et al (1994) Proc Nat. Acad. Sci, USA 91:3809-3813; Schier et al (1995) Gene 169:147-155; Yelton et al (1995) J. Immunol. 155:1994-2004; Jackson et al (1995) J. Immunol. 154(7):3310-9; and Hawkins et al (1992) J. Mol. Biol. 226:889-896).

An "intact antibody" herein is one comprising VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fe constant region (a native sequence Fe region or amino acid sequence variant Fe region) of an antibody. Examples of antibody effector functions include C1q binding; complement dependent cytotoxicity; Fe receptor binding; antibody-dependent cell-mediated cytotoxicity (ADCC); phagocytosis; and down regulation of cell surface receptors such as B cell receptor and BCR.

The term "amino acid sequence variant" refers to polypeptides having amino acid sequences that differ to some extent from a native sequence polypeptide. Ordinarily, amino acid sequence variants will possess at least about 70% sequence identity with at least one receptor binding domain of a native sequence polypeptide or with at least one ligand binding domain of a native receptor, and preferably, they will be at least about 80%, more preferably, at least about 90% homologous by sequence with such receptor or ligand binding domains. The amino acid sequence variants possess substitutions, deletions, and/or insertions at certain positions within the amino acid sequence of the native amino acid sequence. Amino acids are designated by the conventional names, one-letter and three-letter codes.

"Sequence identity" is defined as the percentage of residues in the amino acid sequence variant that are identical after aligning the sequences and introducing gaps, if necessary, to achieve the maximum percent sequence identity. Methods and computer programs for the alignment are well known in the art. One such computer program is "Align 2," authored by Genentech, Inc., which was filed with user documentation in the United States Copyright Office, Washington, D.C. 20559, on Dec. 10, 1991, and which code is found in PCT/US03/07209 (U.S. Pat. No. 7,288,248).

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, (1991) "Annu. Rev. Immunol." 9:457-92. To assess ADCC activity of a molecule of interest, an in vitro ADCC assay, such as that described in U.S. Pat. No. 5,500, 362 and U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al (1998) Proc. Nat. Acad. Sci. (USA) 95:652-656.

"Human effector cells" are leukocytes which express one or more constant region receptors (FcRs) and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g., from blood or PBMCs as described herein.

The terms "Fc receptor" or "FcR" mean a receptor that binds to the Fc constant region of an antibody. The preferred FcR is a native sequence human FcR. Moreover, a preferred FcR is one which binds an IgG antibody (a gamma receptor) and includes receptors of the FcγRI, FcγRII, and Fcγ RIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See review M. in Daëron, (1997) "Annu. Rev. Immunol." 15:203-234). FcRs are reviewed in Ravetch and Kinet, (1991) "Annu. Rev. Immunol."., 9:457-92; Capel et al (1994) Immunomethods 4:25-34; and de Haas et al (1995) J. Lab. Clin. Med. 126:330-41. Other FcRs, including those to be identified in the future, are encompassed by the term "FcR" herein. The term also includes the neonatal receptor, FcRn, which is responsible for the transfer of maternal IgGs to the fetus (Guyer et al (1976) J. Immunol., 117:587 and Kim et al (1994) J. Immunol. 24:249).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen (Gazzano-Santoro et al (1996) J. Immunol. Methods 202:163).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al (1991) Sequences of Proteins of Immunological Interest, 5th Ed. Public Health Service, National Institutes of Health, Bethesda, Md.). The constant domains are not involved directly in binding an antibody to an antigen, but exhibit various effector functions, such as participation of the antibody in antibody dependent cellular cytotoxicity (ADCC).

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The "contact" hypervariable regions are based on an analysis of the available complex crystal structures. The residues from each of these hypervariable regions are noted below. Unless otherwise denoted, Kabat numbering according to the Kabat Database of aligned sequences of proteins will be employed (Wu and Kabat (1970) J. Exp. Med. 132:211-250; Johnson and Wu (2000) Nuc. Acids Res. 28(1):214-218). Hypervariable region locations are generally as follows: amino acids 24-34 (HVR-L1), amino acids 49-56 (HVR-L2), amino acids 89-97 (HVR-L3), amino acids 26-35A (HVR—H1), amino acids 49-65 (HVR—H2), and amino acids 93-102 (HVR—H3). Hypervariable regions may also comprise "extended hypervariable regions" as follows: amino acids 24-36 (L1), and amino acids 46-56 (L2) in the VL. The variable domain residues are numbered according to Kabat et al., supra for each of these definitions. An "altered hypervariable region" for the purposes herein is a hypervariable region comprising one or more (e.g. one to about 16) amino acid substitution(s) therein. An "un- modified hypervariable region" for the purposes herein is a hypervariable region having the same amino acid sequence as a non-human antibody from which it was derived, i.e. one which lacks one or more amino acid substitutions therein.

The terms "variable domain residue numbering as in Kabat", "amino acid position numbering as in Kabat", and variations thereof, refer to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, an FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

An "antigen" is a predetermined polypeptide, carbohydrate, nucleic acid, lipid, hapten or other naturally occurring or synthetic compound to which an antibody can selectively bind.

"Framework" or "FR" residues are those variable domain residues other than the hypervariable region residues as herein defined. A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al, Sequences of Proteins of Immunological Interest, 5th Ed. Public Health Service, National Institutes of Health, Bethesda, Md. (1991). In one embodiment, for the VL, the subgroup is subgroup kappa I as in Kabat et al. In one embodiment, for the VH, the subgroup is subgroup III as in Kabat et al. A "VH subgroup III consensus framework" comprises the consensus sequence obtained from the amino acid sequences in variable heavy subgroup III of Kabat et al. A "VL subgroup I consensus framework" comprises the consensus sequence obtained from the amino acid sequences in variable light kappa subgroup I of Kabat et al.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the VH and VL domains which enables the scFv to form the desired structure for antigen binding (Plückthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a variable heavy domain (VH) connected to a variable light domain (VL) in the same polypeptide chain (VH-VL). By using a linker that is too short to allow pairing between the two domains on the same chain, the domains are forced to pair with the complementary domains of another chain and create two antigen-binding sites (EP 404,097; WO 93/11161; Hollinger et al (1993) Proc. Natl. Acad. Sci. USA 90:6444-6448).

A "free cysteine amino acid" refers to a cysteine amino acid residue which has been engineered into a parent antibody, has a thiol functional group (—SH), and is not paired as, or otherwise part of, an intramolecular or intermolecular disulfide bridge.

The term "thiol reactivity value" is a quantitative characterization of the reactivity of free cysteine amino acids. The thiol reactivity value is the percentage of a free cysteine amino acid in a cysteine engineered antibody which reacts with a thiol-reactive reagent, and converted to a maximum value of 1. For example, a free cysteine amino acid on a cysteine engineered antibody which reacts in 100% yield with a thiol-reactive reagent, such as a biotin-maleimide reagent, to form a biotin-labelled antibody has a thiol reactivity value of 1.0. Another cysteine amino acid engineered into the same or different parent antibody which reacts in 80% yield with a thiol-reactive reagent has a thiol reactivity value of 0.8. Another cysteine amino acid engineered into the same or different parent antibody which fails totally to react with a thiol-reactive reagent has a thiol reactivity value of 0. Determination of the thiol reactivity value of a particular cysteine may be conducted by ELISA assay, mass spectroscopy, liquid chromatography, autoradiography, or other quantitative analytical tests. Thiol-reactive reagents which allow capture of the cysteine engineered antibody and comparison and quantitation of the cysteine reactivity include biotin-PEO-maleimide ((+)-biotinyl-3-malcimidopropionamidyl-3,6-dioxaoctainediamine, Oda et al (2001) Nature Biotechnology 19:379-382, Pierce Biotechnology, Inc.) Biotin-BMCC, PEO-Iodoacetyl Biotin, Iodoacetyl-LC-Biotin, and Biotin-HPDP (Pierce Biotechnology, Inc.), and Nα-(3-maleimidyl-propionyl)biocytin (MPB, Molecular Probes, Eugene, Oreg.). Other commercial sources for biotinylation, bifunctional and multifunctional linker reagents include Molecular Probes, Eugene, Oreg., and Sigma, St. Louis, Mo.

A "parent antibody" is an antibody comprising an amino acid sequence from which one or more amino acid residues are replaced by one or more cysteine residues. The parent antibody may comprise a native or wild type sequence. The parent antibody may have pre-existing amino acid sequence modifications (such as additions, deletions and/or substitutions) relative to other native, wild type, or modified forms of an antibody. A parent antibody may be directed against a target antigen of interest, e.g. a biologically important polypeptide. Antibodies directed against nonpolypeptide antigens (such as tumor-associated glycolipid antigens; see U.S. Pat. No. 5,091,178) are also contemplated.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody "which binds" a molecular target or an antigen of interest, e.g., TENB2 or CA125 antigens, is one capable of binding that antigen with sufficient affinity such that the antibody is useful in targeting a cell expressing the antigen. Where the antibody is one which binds TENB2, it will usually preferentially bind TENB2, and may be one which does not significantly cross-react with other proteins. In such embodiments, the extent of binding of the antibody to these non-TENB2 proteins (e.g., cell surface binding to endogenous receptor) will be less than 10% as determined by fluorescence activated cell sorting (FACS) analysis or radioimmunoprecipitation (RIA).

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a CA125/O772P polypeptide-expressing cancer if, after receiving a therapeutic amount of an anti-CA125/O772P antibody, such as a cysteine engineered anti-TENB2 antibody, or antibody drug conjugate thereof, according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the cysteine engineered anti-TENB2 antibody, or antibody drug conjugate thereof, may prevent growth and/or kill existing cancer cells, it may be cytostatic and/or cytotoxic. Reduction of these signs or symptoms may also be felt by the patient. The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

The terms "cancer" and "cancerous" refer to or describe the physiological condition in mammals that is typically characterized by unregulated cell growth. A "tumor" comprises one or more cancerous cells, and refers to all neoplastic cell growth and proliferation, whether malignant or benign, and all pre-cancerous and cancerous cells and tissues. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A cancer which "overexpresses" an antigenic receptor is one which has significantly higher levels of the receptor, such as TENB2, at the cell surface thereof, compared to a noncancerous cell of the same tissue type. Such overexpression may be caused by gene amplification or by increased transcription or translation. Receptor overexpression may be determined in a diagnostic or prognostic assay by evaluating increased levels of the receptor protein present on the surface of a cell (e.g., via an immunohistochemistry assay; IHC). Alternatively, or additionally, one may measure levels of receptor-encoding nucleic acid in the cell, e.g., via fluorescent in situ hybridization (FISH; see WO 98/45479), southern blotting, or polymerase chain reaction (PCR) techniques, such as real time quantitative reverse-transcriptase PCR (qRT-PCR).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

The terms "cell proliferative disorder" and "proliferative disorder" refer to disorders that are associated with some degree of abnormal cell proliferation. In one embodiment, the cell proliferative disorder is cancer.

The term "therapeutically effective amount" refers to an amount of a drug, e.g. a cysteine engineered anti-TENB2 antibody drug conjugate or chemotherapeutic agent, effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The term "cytostatic" refers to the effect of limiting the function of cells, such as limiting cellular growth or proliferation of cells. For cancer therapy, efficacy can, for example, be measured by assessing the time to disease progression (TTP) and/or determining the response rate (RR).

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millenium Pharm.), fulvestrant (FASLODEX®, AstraZeneca), sutent (SU11248, Pfizer), letrozole (FEMARA®, Novartis), imatinib mesylate (GLEEVEC®, Novartis), PTK787/ZK 222584 (Novartis), oxaliplatin (Eloxatin®, Sanofi), 5-FU (5-fluorouracil), leucovorin, Rapamycin (Sirolimus, RAPAMUNE®, Wyeth), lapatinib (TYKERB®, GSK572016, GlaxoSmithKline), lonafarnib (SCH 66336), sorafenib (BAY43-9006, Bayer Labs.), and gefitinib (IRESSA®, Astrazeneca), AG 1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; (ii) aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in abherant cell proliferation, such as, for example, PKC-alpha, Ralf and H-Ras; (viii) ribozymes such as a VEGF expression inhibitor (e.g., ANGIOZYME® ribozyme) and a HER2 expression inhibitor; (ix) vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; (x) anti-angiogenic agents such as bevacizumab (AVASTIN®, Genentech); and (xi) pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoictin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "label" means any moiety which can be covalently attached to an antibody and that functions to: (i) provide a detectable signal; (ii) interact with a second label to modify the detectable signal provided by the first or second label, e.g. FRET (fluorescence resonance energy transfer); (iii) stabilize interactions or increase affinity of binding, with antigen or ligand; (iv) affect mobility, e.g. electrophoretic mobility, or cell-permeability, by charge, hydrophobicity, shape, or other physical parameters, or (v) provide a capture moiety, to modulate ligand affinity, antibody/antigen binding, or ionic complexation.

The phrase "pharmaceutically acceptable salt," as used herein, refers to pharmaceutically acceptable organic or inorganic salts of an ADC. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" refers to an association of one or more solvent molecules and an ADC. Examples of solvents that form pharmaceutically acceptable solvates include, but are not limited to, water, isopropanol, ethanol, methanol, DMSO, ethyl acetate, acetic acid, and ethanolamine.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The following abbreviations are used herein and have the indicated definitions: BME is beta-mercaptoethanol, Boc is N-(t-butoxycarbonyl), cit is citrulline (2-amino-5-ureido pentanoic acid), dap is dolaproine, DCC is 1,3-dicyclohexylcarbodiimide, DCM is dichloromethane, DEA is diethylamine, DEAD is diethylazodicarboxylate, DEPC is diethylphosphorylcyanidate, DIAD is diisopropylazodicarboxylate, DIEA is N,N-diisopropylethylamine, dil is dolaisoleucine, DMA is dimethylacetamide, DMAP is 4-dimethylaminopyridine, DME is ethyleneglycol dimethyl ether (or 1,2-dimethoxyethane), DMF is N,N-dimethylformamide, DMSO is dimethylsulfoxide, doe is dolaphenine, dov is N,N-dimethylvaline, DTNB is 5,5'-dithiobis (2-nitrobenzoic acid), DTPA is diethylenetriaminepentaacetic acid, DTT is dithiothreitol, EDCI is 1-(3-dimethylaminopropyl)-3-ethylcarbodiimide hydrochloride, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN ($CH_3CN$) is acetonitrile, MeOH is methanol, Mtr is 4-anisyldiphenylmethyl (or 4-methoxytrityl), nor is (1S,2R)-(+)-norephedrine, PAB is p-aminobenzylcarbamoyl, PBS is phosphate-buffered saline (pH 7), PEG is polyethylene glycol, Ph is phenyl, Pnp is p-nitrophenyl, MC is 6-maleimidocaproyl, phe is L-phenylalanine, PyBrop is bromo tris-pyrrolidino phosphonium hexafluorophosphate, SEC is size-exclusion chromatography, Su is succinimide, TFA is trifluoroacetic acid, TLC is thin layer chromatography, UV is ultraviolet, and val is valine.

Cysteine Engineered Anti-TENB2 Antibodies

The compounds of the invention include cysteine engineered anti-TENB2 antibodies where one or more amino acids of any form of wild-type or parent anti-TENB2 antibody is replaced with a cysteine amino acid. The engineered cysteine amino acid is a free cysteine acid and not part of an intrachain or interchain disulfide unit. Any form of anti-TENB2 antibody may be so engineered, i.e. mutated. For example, a parent Fab antibody fragment may be engineered to form a cysteine engineered Fab, referred to herein as "Thio-Fab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. The cysteine engineered anti-TENB2 antibodies of the invention include monoclonal antibodies, humanized or chimeric monoclonal antibodies, antigen-binding fragments of antibodies, fusion polypeptides and analogs that preferentially bind cell-associated TENB2 polypeptides.

Cysteine engineered anti-TENB2 antibodies retain the antigen binding capability of their wild type, parent anti-TENB2 antibody counterparts. Thus, cysteine engineered anti-TENB2 antibodies are capable of binding to TENB2 antigens.

A cysteine engineered anti-TENB2 antibody comprises one or more free cysteine amino acids with reduced sulfhydryl (thiol) groups wherein the cysteine engineered anti-TENB2 antibody binds to a TENB2 polypeptide.

In one embodiment, the cysteine engineered anti-TENB2 antibody is prepared by a process comprising replacing one or more amino acid residues of a parent anti-TENB2 antibody by cysteine.

Mutants with replaced ("engineered") cysteine (Cys) residues may be evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies of the invention may be in the ranges of 0.6 to 1.0; 0.7 to 1.0; or 0.8 to 1.0.

In one aspect, the invention concerns an isolated cysteine engineered anti-TENB2 antibody comprising an amino acid sequence that is encoded by a nucleotide sequence that hybridizes to the complement of a DNA molecule encoding (a) a cysteine engineered antibody having a full-length amino acid sequence as disclosed herein, (b) a cysteine engineered antibody amino acid sequence lacking the signal peptide as disclosed herein, (c) an extracellular domain of a transmembrane cysteine engineered antibody protein, with or without the signal peptide, as disclosed herein, (d) an amino acid sequence encoded by any of the nucleic acid sequences disclosed herein or (e) any other specifically defined fragment of a full-length cysteine engineered antibody amino acid sequence as disclosed herein.

In one aspect, the invention provides an isolated cysteine engineered anti-TENB2 antibody without the N-terminal signal sequence and/or without the initiating methionine and is encoded by a nucleotide sequence that encodes such an amino acid sequence as described in. Processes for producing the same are also herein described, wherein those processes comprise culturing a host cell comprising a vector which comprises the appropriate encoding nucleic acid molecule under conditions suitable for expression of the cysteine engineered antibody and recovering the cysteine engineered antibody from the cell culture.

Another aspect of the invention provides an isolated cysteine engineered anti-TENB2 antibody which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the cysteine engineered antibody and recovering the cysteine engineered antibody from the cell culture.

In other embodiments, the invention provides isolated anti-TENB2 chimeric cysteine engineered antibodies comprising any of the herein described cysteine engineered antibody fused to a heterologous (non-TENB2) polypeptide. Examples of such chimeric molecules comprise any of the herein described cysteine engineered antibodies fused to a heterologous polypeptide such as, for example, an epitope tag sequence or an Fc region of an immunoglobulin.

The cysteine engineered anti-TENB2 antibody may be a monoclonal antibody, antibody fragment, chimeric antibody, humanized antibody, single-chain antibody or antibody that competitively inhibits the binding of an anti-TENB2 polypeptide antibody to its respective antigenic epitope. Antibodies of the present invention may optionally be conjugated to a growth inhibitory agent or cytotoxic agent such as a toxin, including, for example, an auristatin, an antibiotic, a radioactive isotope, a nucleolytic enzyme, or the like. The antibodies of the present invention may optionally be produced in CHO cells or bacterial cells and preferably inhibit the growth or proliferation of or induce the death of a cell to which they bind. For diagnostic purposes, the antibodies of the present invention may be detectably labeled, attached to a solid support, or the like.

In other embodiments of the present invention, the invention provides vectors comprising DNA encoding any of the herein described cysteine engineered anti-TENB2 antibodies. Host cells comprising any such vector are also provided. By way of example, the host cells may be CHO cells, E. coli cells, or yeast cells. A process for producing any of the herein described polypeptides is further provided and comprises culturing host cells under conditions suitable for expression of the desired polypeptide and recovering the desired polypeptide from the cell culture.

Parent and cysteine engineered anti-TENB2 antibodies bind to a TENB2 polypeptide or TENB2 polypeptide variant described in PCT/US03/07209 (U.S. Pat. No. 7,288,248).

A TENB2 polypeptide variant is a TENB2 polypeptide having at least about 80% amino acid sequence identity with a TENB2 which is a: (i) full-length native sequence; (ii) a polypeptide sequence lacking the signal peptide; (iii) an extracellular domain, with or without the signal peptide; (iv) or any other fragment of a full-length TENB2 polypeptide sequence. Such TENB2 polypeptide variants include, for instance, polypeptides wherein one or more amino acid residues are added, or deleted, at the N- or C-terminus of the full-length native amino acid sequence. Ordinarily, a TENB2 polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence TENB2 polypeptide sequence, a TENB2 polypeptide sequence lacking the signal peptide, an extracellular domain of a TENB2 polypeptide, with or without the signal peptide, or any other specifically defined fragment of a full-length TENB2 polypeptide sequence. Ordinarily, TENB2 polypeptide variants are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, TENB2 variant polypeptides will have no more than one conservative amino acid substitution as compared to the native TENB2 polypeptide sequence, alternatively no more than 2, 3, 4, 5, 6, 7, 8, 9, or 10 conservative amino acid substitution as compared to the native TENB2 polypeptide sequence.

TENB2 polypeptides may be prepared by recombinant expression in: (i) E. coli with pBR322 vector; (ii) mammalian cells such as human HEK293 cells (ATCC CCL 1573), COS (simian fibroblast, SV-40) cells, Chinese Hamster Ovary (CHO) cells with the pRK5 vector; (iii) yeast, such as yeast strain AB110; or (iv) baculovirus-infected insect cells (PCT/US03/07209; U.S. Pat. No. 7,288,248). Native or recombinant TENB2 polypeptides may be purified by a variety of standard techniques in the art of protein purification. For example, pro-TENB2 polypeptide, mature TENB2 polypeptide, or pre-TENB2 polypeptide is purified by immunoaffinity chromatography using antibodies specific for the TENB2 polypeptide of interest. In general, an immunoaffinity column is constructed by covalently coupling the anti-TENB2 polypeptide antibody to an activated chromatographic resin. TENB2 polypeptides may be produced recombinantly as a fusion polypeptide with a heterologous polypeptide, which may be a signal sequence or other polypeptide having a specific cleavage site at the N-terminus of the mature protein or polypeptide. Alternatively, TENB2 polypeptides may be produced as fusion polypeptides with a signal sequence and a heterologous polypeptide sequence that allows purification of the TENB2 fusion polypeptide; examples of such polypeptides are polyhistidine ($His_6$ (SEQ ID NO: 24) or $His_8$ (SEQ ID NO: 25)), human IgG Fc, the FLAG epitope (KDYKDDDDK (SEQ ID NO: 26)), and the gD epitope. (KYALADASLKMADPNRFRGKDLPVL (SEQ ID NO: 27)). The signal sequence may be a component of the vector, or it may be a part of the anti-TENB2 antibody- or TENB2 polypeptide-encoding DNA that is inserted into the vector. The signal sequence may be a prokaryotic signal sequence selected, for example, from the group of the alkaline phosphatase, penicillinase, 1 pp, or heat-stable enterotoxin II leaders. For yeast secretion the signal sequence may be, e.g., the yeast invertase leader, alpha factor leader (including Saccharomyces and Kluyveromyces a-factor leaders (U.S. Pat. No. 5,010,182), or acid phosphatase leader, the C. albicans glucoamylase leader (EP 0362179), or the signal described in WO 90/13646. In mammalian cell expression, mammalian signal sequences may be used to direct secretion of the protein, such as signal sequences from secreted polypeptides of the same or related species, as well as viral secretory leaders.

A TENB2-expressing cell expresses an endogenous or transfected TENB2 polypeptide antigen either on the cell surface or in a secreted form. A TENB2-expressing cancer comprises cells that have a TENB2 polypeptide present on the cell surface or that produce and secrete a TENB2 antigenic polypeptide. A TENB2-expressing cancer optionally produces sufficient levels of TENB2 polypeptide on the surface of cells thereof, such that an anti-TENB2 antibody, or antibody drug conjugate thereof, can bind thereto and may exert a therapeutic effect with respect to the cancer. A cancer which overexpresses a TENB2 polypeptide is one which has significantly higher levels of TENB2 polypeptide at the cell surface thereof, or produces and secretes, compared to a noncancerous cell of the same tissue type. Such overexpression may be caused by gene amplification or by increased transcription or translation. TENB2 polypeptide overexpression may be determined in a clinical setting by evaluating increased levels of the TENB2 protein present on the surface of a cell, or secreted by the cell (e.g., via an immunohistochemistry assay using anti-TENB2 antibodies prepared against an isolated TENB2 polypeptide which may be prepared using recombinant DNA technology from an isolated nucleic acid encoding the TENB2 polypeptide; FACS analysis, etc.). Alternatively, or additionally, one may measure levels of TENB2 polypeptide-encoding nucleic acid or mRNA in the cell, e.g., via fluorescent in situ hybridization (FISH) using a nucleic acid based probe corresponding to a TENB2-encoding nucleic acid or the complement thereof; (WO 98/45479), Southern blotting, Northern blotting, or polymerase chain reaction (PCR) techniques, such as real time quantitative reverse-transcriptase PCR (qRT-PCR). One may also detect TENB2 polypeptide overexpression by measuring shed antigen in a biological fluid such as serum, e.g., using antibody-based assays (U.S. Pat. No. 4,933,294; WO 91/05264; U.S. Pat. No. 5,401,638; Sias et al (1990) J. Immunol. Methods 132:73-80). Various other in vivo assays may be contemplated. Alternatively, cells within the body of the patient may be exposed to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

Parent and cysteine engineered anti-TENB2 antibodies are capable of binding, preferably specifically, to a TENB2 polypeptide as described herein. TENB2 binding oligopeptides may be identified without undue experimentation using well known techniques. In this regard, it is noted that techniques for screening oligopeptide libraries for oligopeptides that are capable of specifically binding to a polypeptide target are well known in the art (U.S. Pat. No. 5,556,762; U.S. Pat. No. 5,750,373; U.S. Pat. No. 4,708,871; U.S. Pat. No. 4,833,092; U.S. Pat. No. 5,223,409; U.S. Pat. No. 5,403,484; U.S. Pat. No. 5,571,689; U.S. Pat. No. 5,663,143; WO 84/03506; WO84/03564; Geysen et al (1984) Proc. Natl. Acad. Sci. USA, 81:3998-4002; Geysen et al (1985) Proc. Natl. Acad. Sci. USA, 82:178-182; Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

The parent and cysteine engineered anti-TENB2 antibodies of the invention include polyclonal, monoclonal, humanized, human, bispecific, and heteroconjugate antibodies.

Various forms of a humanized anti-TENB2 antibody are contemplated. For example, the humanized antibody may be an antibody fragment, such as a Fab. Alternatively, the humanized antibody may be an intact antibody, such as an intact IgG1 antibody.

Bispecific anti-TENB2 antibodies are antibodies that have binding specificities for at least two different epitopes. Exemplary bispecific anti-TENB2 antibodies may bind to two different epitopes of a TENB2 protein as described herein. Other such antibodies may combine a TENB2 binding site with a binding site for another protein. Alternatively, an anti-TENB2 arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the TENB2-expressing cell. Bispecific antibodies may also be used to localize cytotoxic agents to cells which express TENB2. These antibodies possess a TENB2-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies). Traditional production of full length bispecific antibodies is based on the co-expression of two immunoglobulin heavy chain-light chain pairs, where the two chains have different specificities (Millstein et al (1983) Nature 305:537-539).

Heteroconjugate anti-TENB2 antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies may be prepared in vitro using known methods in synthetic protein chemistry, including those involving crosslinking agents.

The anti-TENB2 antibodies of the present invention can be multivalent antibodies with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH—CH1-flexible linker-VH—CH1-Fc region chain; or VH—CH1-VH—CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

The effector function of an anti-TENB2 antibody may be modified by introducing one or more amino acid substitutions in an Fc region. Such modification may enhance antigen-dependent cell-mediated cyotoxicity (ADCC) and/or complement dependent cytotoxicity (CDC) of the anti-TENB2 antibody. The homodimeric antibody thus generated may have improved internalization capability and/or increased complement-mediated cell killing and antibody-dependent cellular cytotoxicity (ADCC). See Caron et al (1992) J. Exp Med. 176:1191-1195 and Shopes, B. J. (1992) Immunol. 148:2918-2922. Homodimeric anti-TENB2 antibodies with enhanced anti-tumor activity may also be prepared using heterobifunctional cross-linkers as described in Wolff et al (1993) Cancer Research 53:2560-2565. Alternatively, an antibody can be engineered which has dual Fc regions and may thereby have enhanced complement lysis and ADCC capabilities (Stevenson et al (1989) Anti-Cancer Drug Design 3:219-230).

The serum half life of an anti-TENB2 antibody may be modulated by incorporating a salvage receptor binding epitope, e.g. an antibody fragment (U.S. Pat. No. 5,739,277). As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Monoclonal antibodies binding to TENB2 epitopes, including TMEFF2#19, are determined by standard competitive binding analysis and epitope mapping (PCT/US03/07209; U.S. Pat. No. 7,288,248).

Immunohistochemistry analysis was performed using TMEFF2#19 monoclonal antibodies (PCT/US03/07209; Sambrook et al *Molecular Cloning: A Laboratory Manual*, New York: Cold Spring Harbor Press, 1989; Ausubel et al., *Current Protocols of Molecular Biology*, Unit 3.16, John Wiley and Sons, 1997). Monoclonal antibody TMEFF2#19 demonstrated weak to strong binding in 176 of 241 human prostate cancer specimens.

Monoclonal antibody TMEFF2#19 becomes internalized into cells to which it binds TENB2 polypeptide on the cell surface at a rapid rate.

Modifications of Anti-TENB2 Antibodies

Modifications and variations in the anti-TENB2 antibodies described herein, can be made, for example, using any of the techniques and guidelines known in the art for conservative and non-conservative mutations, for example, those in U.S. Pat. No. 5,364,934. Variations may be a substitution, deletion or insertion of one or more codons encoding the antibody or polypeptide that results in a change in the amino acid sequence as compared with the native sequence anti-TENB2 antibody. Optionally the variation is by substitution of at least one amino acid with any other amino acid in one or more of the domains of the anti-TENB2 antibody. The variations can be made using methods known in the art such as oligonucleotide-mediated (site-directed) mutagenesis, alanine scanning, and PCR mutagenesis. Site-directed mutagenesis (Carter et al (1986) Nucl. Acids Res., 13:4331; Zoller et al (1987) Nucl. Acids Res., 10:6487), cassette mutagenesis (Wells et al (1985) Gene, 34:315), restriction selection mutagenesis (Wells et al (1986) Philos. Trans. R. Soc. London SerA, 317:415) or other known techniques can be performed on the cloned DNA to produce the anti-TENB2 antibody variant DNA. Amino acid changes may alter post-translational processes of the anti-TENB2 antibody, such as changing the number or position of glycosylation sites or altering the membrane anchoring characteristics. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, (1983) W.H. Freeman & Co., San Francisco, pp. 79-86), acetylation of the N-terminal amine, and amidation of any C-terminal carboxyl group. Anti-TENB2 antibodies can be prepared by introducing appropriate nucleotide changes into the encoding DNA, and/or by chemical synthesis.

Anti-TENB2 antibody fragments may be truncated at the N-terminus or C-terminus, or may lack internal residues, for example, when compared with a full length anti-TENB2 antibody. Certain fragments lack amino acid residues that are not essential for a desired biological activity of the anti-TENB2 antibody. Anti-TENB2 antibody fragments may be prepared by any of a number of conventional techniques. Desired peptide fragments may be chemically synthesized. An alternative approach involves generating antibody fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or fragment, by polymerase chain reaction (PCR). Oligonucleotides that define the desired termini of the DNA fragment are employed at the 5' and 3' primers in the PCR. Preferably, anti-TENB2 antibody fragments share at least one biological and/or immunological activity with the native anti-TENB2 antibody disclosed herein.

A particularly preferred type of substitutional variant involves substituting one or more hypervariable region residues of a humanized or human antibody. Generally, the resulting variant(s) selected for further development will have improved biological properties relative to the antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human TENB2 polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of covalent modification of the anti-TENB2 antibody included within the scope of this invention comprises altering the native glycosylation pattern of the antibody or polypeptide by deleting one or more carbohydrate moieties found in native sequence anti-TENB2 antibody (either by removing the underlying glycosylation site or by deleting the glycosylation by chemical and/or enzymatic means), and/or adding one or more glycosylation sites that are not present in the native sequence anti-TENB2 antibody. In addition, the modification includes qualitative changes in the glycosylation of the native proteins, involving a change in the nature and proportions of the various carbohydrate moieties present. Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-Linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. Addition of glycosylation sites to the anti-TENB2 antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the anti-TENB2 antibody (for O-linked glycosylation sites). The anti-TENB2 antibody amino acid sequence may optionally be altered through changes at the DNA level, particularly by mutating the DNA encoding the anti-TENB2 antibody at preselected bases such that codons are generated that will translate into the desired amino acids.

Another means of increasing the number of carbohydrate moieties on the anti-TENB2 antibody is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem*., pp. 259-306 (1981).

Removal of carbohydrate moieties present on the anti-TENB2 antibody may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties can be achieved by the use of a variety of endo- and exo-glycosidases as described by Thotakura et al (1987) Meth. Enzymol. 138:350.

Another type of covalent modification of anti-TENB2 antibody comprises linking the antibody or polypeptide to one of a variety of nonproteinaceous polymers, e.g., polyethylene glycol (PEG), polypropylene glycol, or polyoxyalkylenes, in the manner set forth in U.S. Pat. No. 4,640,835; U.S. Pat. No. 4,496,689; U.S. Pat. No. 4,301,144; U.S. Pat. No. 4,670,417; U.S. Pat. No. 4,791,192 or U.S. Pat. No. 4,179,337. The antibody or polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* 16th edition, Oslo, A., Ed., (1980).

The anti-TENB2 antibody of the present invention may also be modified in a way to form chimeric molecules comprising an anti-TENB2 antibody fused to another, heterologous polypeptide or amino acid sequence. In one embodiment, such a chimeric molecule comprises a fusion of the anti-TENB2 antibody with a tag polypeptide which provides an epitope to which an anti-tag antibody can selectively bind. The epitope tag is generally placed at the amino- or carboxyl-terminus of the anti-TENB2 antibody. The presence of such epitope-tagged forms of the anti-TENB2 antibody can be detected using an antibody against the tag polypeptide. Also, provision of the epitope tag enables the anti-TENB2 antibody to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al (1988) Mol. Cell. Biol., 8:2159-2165); the c-myc tag and the 8F9, 3C7, 6E10, G4, B7 and 9E10 antibodies thereto (Evan et al (1985) Molecular and Cellular Biology, 5:3610-3616); and the Herpes Simplex virus glycoprotein D (gD) tag and its antibody (Paborsky et al (1990) Protein Engineering, 3(6):547-553). Other tag polypeptides include the Flag-peptide (Hopp et al (1988) BioTechnology 6:1204-1210); the KT3 epitope peptide (Martin et al (1992) Science, 255:192-194); an $\alpha$-tubulin epitope peptide (Skinner et al (1991) J. Biol. Chem., 266:15163-15166); and the T7 gene 10 protein peptide tag (Lutz-Freyermuth et al (1990) Proc. Natl. Acad. Sci. USA, 87:6393-6397).

In an alternative embodiment, the chimeric molecule may comprise a fusion of the anti-TENB2 antibody with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an anti-TENB2 antibody in place of at least one variable region within an Ig molecule. In a particularly preferred embodiment, the immunoglobulin fusion includes the hinge, $CH_2$ and $CH_3$, or the hinge, $CH_1$, $CH_2$ and $CH_3$ regions of an IgG1 molecule (U.S. Pat. No. 5,428,130).

Preparation of Anti-TENB2 Antibodies

DNA encoding an amino acid sequence variant of the cysteine engineered anti-TENB2 antibodies and parent anti-TENB2 antibodies of the invention is prepared by a variety of methods which include, but are not limited to, isolation from a natural source (in the case of naturally occurring amino acid sequence variants), preparation by site-directed (or oligonucleotide-mediated) mutagenesis (Carter (1985) et al Nucleic Acids Res. 13:4431-4443; Ho et al (1989) Gene (Amst.) 77:51-59; Kunkel et al (1987) Proc. Natl. Acad. Sci. USA 82:488; Liu et al (1998) J. Biol. Chem. 273:20252-20260), PCR mutagenesis (Higuchi, (1990) in PCR Protocols, pp. 177-183, Academic Press; Ito et al (1991) Gene 102:67-70; Bernhard et al (1994) Bioconjugate Chem. 5:126-132; and Vallette et al (1989) Nuc. Acids Res. 17:723-733), and cassette mutagenesis (Wells et al (1985) Gene 34:315-323) of an earlier prepared DNA encoding the polypeptide. Mutagenesis protocols, kits, and reagents are commercially available, e.g. QuikChange® Multi Site-Direct Mutagenesis Kit (Stratagene, La Jolla, Calif.). Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition; Zoller et al (1983) Methods Enzymol. 100:468-500; Zoller, M. J. and Smith, M. (1982) Nucl. Acids Res. 10:6487-6500). Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies (Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993).

Phage display technology (McCafferty et al (1990) Nature 348:552-553) can be used to produce anti-TENB2 human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell (Johnson et al (1993) Current Opinion in Structural Biology 3:564-571; Clackson et al (1991) Nature, 352:624-628; Marks et al (1991) J. Mol. Biol. 222:581-597; Griffith et al (1993) EMBO J. 12:725-734; U.S. Pat. No. 5,565,332; U.S. Pat. No. 5,573,905; U.S. Pat. No. 5,567,610; U.S. Pat. No. 5,229,275).

Anti-TENB2 antibodies may be chemically synthesized using known oligopeptide synthesis methodology or may be prepared and purified using recombinant technology. The appropriate amino acid sequence, or portions thereof, may be produced by direct peptide synthesis using solid-phase techniques (Stewart et al., Solid-Phase Peptide Synthesis, (1969) W.H. Freeman Co., San Francisco, Calif.; Merrifield, (1963) J. Am. Chem. Soc., 85:2149-2154). In vitro protein synthesis may be performed using manual techniques or by automation. Automated solid phase synthesis may be accomplished, for instance, employing t-BOC or Fmoc protected amino acids and using an Applied Biosystems Peptide Synthesizer (Foster City, Calif.) using manufacturer's instructions. Various portions of the anti-TENB2 antibody or TENB2 polypeptide may be chemically synthesized separately and combined using chemical or enzymatic methods to produce the desired anti-TENB2 antibody or TENB2 polypeptide.

Various techniques have been developed for the production of antibody fragments. Traditionally, these fragments were derived via proteolytic digestion of intact antibodies (Morimoto et al (1992) Journal of Biochemical and Biophysical Methods 24:107-117; and Brennan et al (1985) Science, 229:81), or produced directly by recombinant host cells. Fab, Fv and ScFv anti-TENB2 antibody fragments can all be expressed in and secreted from E. coli, thus allowing the facile production of large amounts of these fragments. Antibody fragments can be isolated from the antibody phage libraries discussed herein. Alternatively, Fab'-SH fragments can be directly recovered from E. coli and chemically coupled to form F(ab')$_2$ fragments (Carter et al (1992) Bio/Technology 10:163-167), or isolated directly from recombinant host cell culture. The anti-TENB2 antibody may be a (scFv) single chain Fv fragment (WO 93/16185; U.S. Pat. No. 5,571,894; U.S. Pat. No. 5,587,458). The anti-TENB2 antibody fragment may also be a "linear antibody" (U.S. Pat. No. 5,641,870). Such linear antibody fragments may be monospecific or bispecific.

The description below relates primarily to production of anti-TENB2 antibodies by culturing cells transformed or transfected with a vector containing anti-TENB2 antibody-encoding nucleic acid. DNA encoding anti-TENB2 antibodies may be obtained from a cDNA library prepared from tissue believed to possess the anti-TENB2 antibody mRNA and to express it at a detectable level. Accordingly, human anti-TENB2 antibody or TENB2 polypeptide DNA can be conveniently obtained from a cDNA library prepared from human tissue. The anti-TENB2 antibody-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding anti-TENB2 antibody or TENB2 polypeptide is PCR methodology (Sambrook et al., supra; Dieffenbach et al., PCR Primer: A Laboratory Manual, Cold Spring Harbor Laboratory Press, 1995).

Host cells are transfected or transformed with expression or cloning vectors described herein for anti-TENB2 antibody or TENB2 polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as E. coli. Various E. coli strains are publicly available, such as E. coli K12 strain MM294 (ATCC 31,446); E. coli X1776 (ATCC 31,537); E. coli strain W3110 (ATCC 27,325) and K5 772 (ATCC 53,635). Other suitable prokaryotic host cells include Enterobacteriaceae such as Escherichia, e.g., E. coli, Enterobacter, Erwinia, Klebsiella, Proteus, Salmonella, e.g., Salmonella typhimurium, Serratia, e.g., Serratia marcescans, and Shigella, as well as Bacilli such as B. subtilis and B. licheniformis (e.g., B. licheniformis 41P disclosed in DD 266,710 published 12 Apr. 1989), Pseudomonas such as P. aeruginosa, and Streptomyces. These examples are illustrative rather than limiting. Strain W3110 is an exemplary host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including E. coli W3110 strain 1A2, which has the complete genotype tonA; E. coli W3110 strain 9E4, which has the complete genotype tonA ptr3; E. coli W3110 strain 27C7 (ATCC 55,244), which has the complete genotype tonA ptr3 phoA E15 (argF-lac)169 degP ompT kan$^r$; E. coli W3110 strain 37D6, which has the complete genotype tonA ptr3 phoA E15 (argF-lac)169 degP ompT rbs7 ilvG kan$^r$; E. coli W3110 strain 40B4, which is strain 37D6 with a non-kanamycin resistant degP deletion mutation; and an E. coli strain having mutant periplasmic protease (U.S. Pat. No. 4,946,783). Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* may be faster and more cost efficient using, for example, expression of antibody fragments and polypeptides in bacteria with translation initiation regio (TIR) and signal sequences for optimizing expression and secretion (U.S. Pat. No. 5,648,237; U.S. Pat. No. 5,789,199; U.S. Pat. No. 5,840,523). After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for anti-TENB2 antibody- or TENB2 polypeptide-encoding vectors. *Saccharomyces cerevisiae* is a commonly used lower eukaryotic host microorganism. Others include *Schizosaccharomyces pombe* (Beach and Nurse, (1981) Nature, 290: 140; EP 139,383); *Kluyveromyces* hosts (U.S. Pat. No. 4,943,529; Fleer et al (1991) Bio/Technology, 9:968-975) such as, e.g., *K. lactis* (MW98-8C, CBS683, CBS4574; Louvencourt et al (1983) J. Bacteriol., 154(2):737-742), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al (1990) Bio/Technology, 8:135), *K. thermotolerans*, and *K. marxianus; yarrowia* (EP 402226); *Pichia pastoris* (EP 183070; Sreckrishna et al (1988) J. Basic Microbiol., 28:265-278); *Candida; Trichoderma reesia* (EP 244234); *Neurospora crassa* (Case et al (1979) Proc. Natl. Acad. Sci. USA, 76:5259-5263); *Schwanniomyces* such as *Schwanniomyces occidentalis* (EP 394538); and filamentous fungi such as, e.g., *Neurospora, Penicillium, Tolypocladium* (WO 91/00357), and *Aspergillus* hosts such as *A. nidulans* (Ballance et al (1983) Biochem. Biophys. Res. Commun., 112:284-289; Tilburn et al (1983) Gene, 26:205-221; Yelton et al (1984) Proc. Natl. Acad. Sci. USA, 81: 1470-1474) and *A. niger* (Kelly and Hynes, (1985) EMBO J., 4:475-479). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*.

Suitable host cells for the expression of glycosylated anti-TENB2 antibody or TENB2 polypeptide may also be derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Examples of useful mammalian host cell lines are monkey kidney CV1 line transformed by SV40 (COS-7, ATCC CRL 1651); human embryonic kidney line (293 or 293 cells subcloned for growth in suspension culture, Graham et al (1977) J. Gen Virol. 36:59); baby hamster kidney cells (BHK, ATCC CCL 10); Chinese hamster ovary cells/-DHFR(CHO, Urlaub et al (1980) Proc. Natl. Acad. Sci. USA 77:4216); mouse sertoli cells (TM4, Mather (1980) Biol. Reprod. 23:243-251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al (1982) Annals N.Y. Acad. Sci. 383:44-68); MRC 5 cells; FS4 cells; and a human hepatoma line (Hep G2).

Host cells are transformed with the above-described expression or cloning vectors for anti-TENB2 antibody production and cultured in conventional nutrient media modified as appropriate for inducing promoters, selecting transformants, or amplifying the genes encoding the desired sequences. The nucleic acid (e.g., cDNA or genomic DNA) encoding anti-TENB2 antibody or TENB2 polypeptide may be inserted into a replicable vector for cloning (amplification of the DNA) or for expression. The vector may, for example, be in the form of a plasmid, cosmid, viral particle, or phage. The appropriate nucleic acid sequence may be inserted into the vector by a variety of procedures.

Growth inhibition of tumor cells in vitro or in vivo can be determined in various ways known in the art, such as inhibiting cell proliferation of a TENB2-expressing tumor cell in vitro or in vivo by about 25-100% compared to the untreated tumor cell, or by about 30-100%, or by about 50-100% or 70-100%, in one embodiment, at an antibody concentration of about 0.5 to 30 µg/ml. The growth inhibitory effects of an anti-TENB2 antibody in vitro may be assessed by methods known in the art, e.g., using cells which express a TENB2 polypeptide either endogenously or following transfection with the TENB2 gene. For example, appropriate tumor cell lines and TENB2-transfected cells may treated with an anti-TENB2 monoclonal antibody at various concentrations for a few days (e.g., 2-7) days and stained with crystal violet or MTT or analyzed by some other colorimetric assay. A reduced signal indicates growth inhibition. Another method of measuring proliferation would be by comparing $^3$H-thymidine uptake by the cells treated in the presence or absence an anti-TENB2 antibody. After treatment, the cells are harvested and the amount of radioactivity incorporated into the DNA quantitated in a scintillation counter. Inhibition of proliferation would be demonstrated by a reduction of radioactivity. To select for an anti-TENB2 antibody which induces cell death, loss of membrane integrity as indicated by, e.g., propidium iodide (PI), trypan blue or 7AAD uptake, may be assessed relative to control. Appropriate positive controls include treatment of a selected cell line with a growth inhibitory antibody known to inhibit growth of that cell line. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-TENB2 antibody at about 1 µg/kg to about 100 mg/kg body weight results in reduction in tumor size or reduction of tumor cell proliferation within about 5 days to 3 months from the first administration of the antibody, preferably within about 5 to 30 days.

Preparation of Cysteine Engineered Anti-TENB2 Antibodies

The design, selection, and preparation methods of the invention enable cysteine engineered anti-TENB2 antibodies which are reactive with electrophilic functionality. These methods further enable antibody conjugate compounds such as antibody-drug conjugate (ADC) compounds with drug molecules at designated, designed, selective sites. Reactive cysteine residues on an antibody surface allow specifically conjugating a drug moiety through a thiol reactive group such as maleimide or haloacetyl. The nucleophilic reactivity of the thiol functionality of a Cys residue to a maleimide group is about 1000 times higher compared to any other amino acid functionality in a protein, such as amino group of lysine residues or the N-terminal amino group. Thiol specific functionality in iodoacetyl and maleimide reagents may react with amine groups, but higher pH (>9.0) and longer reaction times are required (Garman, 1997, Non-Radioactive Labelling: A Practical Approach, Academic Press, London). The amount of free thiol in a protein may be estimated by the standard Ellman's assay. Immunoglobulin M is an example of a disulfide-linked pentamer, while immunoglobulin G is an example of a protein with internal disulfide bridges bonding the subunits together. In proteins such as this, reduction of the disulfide bonds with a reagent such as dithiothreitol (DTT) or selenol (Singh et al (2002) Anal. Biochem. 304:147-156) is required to generate the reactive free thiol. This approach may result in loss of antibody tertiary structure and antigen binding specificity.

The PHESELECTOR (Phage ELISA for Selection of Reactive Thiols) Assay allows for detection of reactive cysteine groups in antibody-Fabs in an ELISA phage format thereby assisting in the design of cysteine engineered antibodies (US 2007/0092940). The antigen that binds to cysteine engineered antibody is coated on well surfaces, followed by incubation with phage particles displaying cysteine engineered Fabs, addition of HRP labeled secondary antibody, and absorbance detection. Mutant proteins displayed on phage may be screened in a rapid, robust, and high-throughput manner. Libraries of cysteine engineered antibodies can be produced and subjected to binding selection using the same approach to identify appropriately reactive sites of free Cys incorporation from random protein-phage libraries of antibodies or other proteins. This technique includes reacting cysteine mutant proteins displayed on phage with an affinity reagent or reporter group which is also thiol-reactive.

The PHESELECTOR assay allows screening of reactive thiol groups in antibodies. Identification of the A121C variant by this method is exemplary. The entire Fab molecule may be effectively searched to identify more ThioFab variants with reactive thiol groups. A parameter, fractional surface accessibility, was employed to identify and quantitate the accessibility of solvent to the amino acid residues in a polypeptide. The surface accessibility can be expressed as the surface area ($Å^2$) that can be contacted by a solvent molecule, e.g. water. The occupied space of water is approximated as a 1.4 Å radius sphere. Software is freely available or licensable (Secretary to CCP4, Daresbury Laboratory, Warrington, Wash. 4 4AD, United Kingdom, Fax: (+44) 1925 603825 as the CCP4 Suite of crystallography programs which employ algorithms to calculate the surface accessibility of each amino acid of a protein with known x-ray crystallography derived coordinates ("The CCP4 Suite: Programs for Protein Crystallography" (1994) Acta. Cryst. D50:760-763). Two exemplary software modules that perform surface accessibility calculations are "AREAIMOL" and "SURFACE", based on the algorithms of B. Lee and F. M. Richards (1971) J. Mol. Biol. 55:379-400. AREAIMOL defines the solvent accessible surface of a protein as the locus of the centre of a probe sphere (representing a solvent molecule) as it rolls over the Van der Waals surface of the protein. AREAIMOL calculates the solvent accessible surface area by generating surface points on an extended sphere about each atom (at a distance from the atom centre equal to the sum of the atom and probe radii), and eliminating those that lie within equivalent spheres associated with neighboring atoms. AREAIMOL finds the solvent accessible area of atoms in a PDB coordinate file, and summarizes the accessible area by residue, by chain and for the whole molecule. Accessible areas (or area differences) for individual atoms can be written to a pseudo-PDB output file. AREAIMOL assumes a single radius for each element, and only recognizes a limited number of different elements.

AREAIMOL and SURFACE report absolute accessibilities, i.e. the number of square Angstroms (Å). Fractional surface accessibility is calculated by reference to a standard state relevant for an amino acid within a polypeptide. The reference state is tripeptide Gly-X-Gly, where X is the amino acid of interest, and the reference state should be an 'extended' conformation, i.e. like those in beta-strands. The extended conformation maximizes the accessibility of X. A calculated accessible area is divided by the accessible area in a Gly-X-Gly tripeptide reference state and reports the quotient, which is the fractional accessibility. Percent accessibility is fractional accessibility multiplied by 100. Another exemplary algorithm for calculating surface accessibility is based on the SOLV module of the program xsae (Broger, C., F. Hoffman-LaRoche, Basel) which calculates fractional accessibility of an amino acid residue to a water sphere based on the X-ray coordinates of the polypeptide. The fractional surface accessibility for every amino acid in an antibody may be calculated using available crystal structure information (Eigenbrot et al. (1993) J Mol. Biol. 229:969-995).

DNA encoding the cysteine engineered antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as E. coli cells, simian COS cells, Chinese Hamster Ovary (CHO) cells, or other mammalian host cells, such as myeloma cells (U.S. Pat. No. 5,807,715; US 2005/0048572; US 2004/0229310) that do not otherwise produce the antibody protein, to obtain the synthesis of monoclonal antibodies in the recombinant host cells.

After design and selection, cysteine engineered antibodies, e.g. ThioFabs, with the engineered, highly reactive unpaired Cys residues, may be produced by: (i) expression in a bacterial, e.g. E. coli, system (Skerra et al (1993) Curr. Opinion in Immunol. 5:256-262; Plückthun (1992) Immunol. Revs. 130: 151-188) or a mammalian cell culture system (WO 01/00245), e.g. Chinese Hamster Ovary cells (CHO); and (ii) purification using common protein purification techniques (Lowman et al (1991) J. Biol. Chem. 266(17):10982-10988).

The engineered Cys thiol groups react with electrophilic linker reagents and drug-linker intermediates to form cysteine engineered antibody drug conjugates and other labelled cysteine engineered antibodies. Cys residues of cysteine engineered antibodies, and present in the parent antibodies, which are paired and form interchain and intrachain disulfide bonds do not have any reactive thiol groups (unless treated with a reducing agent) and do not react with electrophilic linker reagents or drug-linker intermediates. The newly engineered Cys residue, can remain unpaired, and able to react with, i.e. conjugate to, an electrophilic linker reagent or drug-linker intermediate, such as a drug-maleimide. Exemplary drug-linker intermediates include: MC-MMAE, MC-MMAF, MC-vc-PAB-MMAE, and MC-vc-PAB-MMAF. The structure positions of the engineered Cys residues of the heavy and light chains are numbered according to a sequential numbering system. This sequential numbering system is correlated to the Kabat numbering system (Kabat et al., (1991) Sequences of Proteins of Immunological Interest, 5th Ed. Public Health Service, National Institutes of Health, Bethesda, Md.) starting at the N-terminus, differs from the Kabat numbering scheme (bottom row) by insertions noted by a, b, c. Using the Kabat numbering system, the actual linear amino acid sequence may contain fewer or additional amino acids corresponding to a shortening of, or insertion into, a FR or CDR of the variable domain. The cysteine engineered heavy chain variant sites are identified by the sequential numbering and Kabat numbering schemes.

In one embodiment, the cysteine engineered anti-TENB2 antibody is prepared by a process comprising:

(a) replacing one or more amino acid residues of a parent anti-TENB2 antibody by cysteine; and (b) determining the thiol reactivity of the cysteine engineered anti-TENB2 antibody by reacting the cysteine engineered antibody with a thiol-reactive reagent.

The cysteine engineered antibody may be more reactive than the parent antibody with the thiol-reactive reagent.

The free cysteine amino acid residues may be located in the heavy or light chains, or in the constant or variable domains. Antibody fragments, e.g. Fab, may also be engineered with one or more cysteine amino acids replacing amino acids of the antibody fragment, to form cysteine engineered antibody fragments.

Another embodiment of the invention provides a method of preparing (making) a cysteine engineered anti-TENB2 antibody, comprising:

(a) introducing one or more cysteine amino acids into a parent anti-TENB2 antibody in order to generate the cysteine engineered anti-TENB2 antibody; and (b) determining the thiol reactivity of the cysteine engineered antibody with a thiol-reactive reagent;

wherein the cysteine engineered antibody is more reactive than the parent antibody with the thiol-reactive reagent.

Step (a) of the method of preparing a cysteine engineered antibody may comprise:

(i) mutagenizing a nucleic acid sequence encoding the cysteine engineered antibody;

(ii) expressing the cysteine engineered antibody; and (iii) isolating and purifying the cysteine engineered antibody.

Step (b) of the method of preparing a cysteine engineered antibody may comprise expressing the cysteine engineered antibody on a viral particle selected from a phage or a phagemid particle.

Step (b) of the method of preparing a cysteine engineered antibody may also comprise:

(i) reacting the cysteine engineered antibody with a thiol-reactive affinity reagent to generate an affinity labelled, cysteine engineered antibody; and (ii) measuring the binding of the affinity labelled, cysteine engineered antibody to a capture media.

Another embodiment of the invention is a method of screening cysteine engineered antibodies with highly reactive, unpaired cysteine amino acids for thiol reactivity comprising:

(a) introducing one or more cysteine amino acids into a parent antibody in order to generate a cysteine engineered antibody;

(b) reacting the cysteine engineered antibody with a thiol-reactive affinity reagent to generate an affinity labelled, cysteine engineered antibody; and (c) measuring the binding of the affinity labelled, cysteine engineered antibody to a capture media; and (d) determining the thiol reactivity of the cysteine engineered antibody with the thiol-reactive reagent.

Step (a) of the method of screening cysteine engineered antibodies may comprise:

(i) mutagenizing a nucleic acid sequence encoding the cysteine engineered antibody;

(ii) expressing the cysteine engineered antibody; and (iii) isolating and purifying the cysteine engineered antibody.

Step (b) of the method of screening cysteine engineered antibodies may comprise expressing the cysteine engineered antibody on a viral particle selected from a phage or a phagemid particle.

Step (b) of the method of screening cysteine engineered antibodies may also comprise:

(i) reacting the cysteine engineered antibody with a thiol-reactive affinity reagent to generate an affinity labelled, cysteine engineered antibody; and (ii) measuring the binding of the affinity labelled, cysteine engineered antibody to a capture media.

Cysteine Engineering of TMEFF2#19 IgG Variants

Cysteine was introduced at the heavy chain 121 (sequential numbering excluding the signal sequence) site into full-length, humanized parent monoclonal anti-TENB2 TMEFF2#19 antibodies by the cysteine engineering methods described herein to give A121C thio hu anti-TENB2 TMEFF2#19 humanized variant with heavy chain sequence: SEQ ID NO:1, and light chain sequence: SEQ ID NO:2, FIG. 1. These cysteine engineered monoclonal antibodies were expressed in CHO (Chinese Hamster Ovary) cells by transient fermentation in media containing 1 mM cysteine.

According to one embodiment, humanized TMEFF2#19 cysteine engineered anti-TENB2 antibodies comprise one or more of the following variable region heavy chain sequences with a free cysteine amino acid (Table 1).

TABLE I

Comparison of heavy chain Sequential, Kabat and Eu numbering for hu TMEFF2#19 cysteine engineered anti-TENB2 antibody variants

| Sequence near Cys mutation | Sequential Numbering | Kabat Numbering | Eu Numbering | Seq I.D. |
|---|---|---|---|---|
| DVQLCESGPG | Q5C | Q5C | | 8 |
| LSLTCCVSGYS | A23C | A23C | | 9 |
| LSSVTCADTAV | A88C | A84C | | 10 |
| TLVTVCSASTK | S119C | S112C | | 11 |
| VTVSSCSTKGP | A121C | A114C | A118C | 12 |
| VSSASCKGPSV | T123C | T116C | T120C | 13 |
| WYVDGCEVHNA | V285C | V278C | V282C | 14 |
| KGFYPCDIAVE | S378C | S371C | S375C | 15 |
| PPVLDCDGSFF | S403C | S396C | S400C | 16 |

According to one embodiment, humanized TMEFF2#19 cysteine engineered anti-TENB2 antibodies comprise one or more of the following variable region light chain sequences with a free cysteine amino acid (Table 2).

TABLE 2

Comparison of light chain Sequential and Kabat numbering for hu TMEFF2#19 cysteine engineered anti-TENB2 antibody variants

| Sequence near Cys mutation | Sequential Numbering | Kabat Numbering | Seq. I.D. |
|---|---|---|---|
| SLSAS<u>C</u>GDRVT | V15C | V15C | 17 |
| ETKRT<u>C</u>AAPSV | V110C | V110C | 18 |
| TVAAP<u>C</u>VFIFP | S114C | S114C | 19 |
| FIFPP<u>C</u>DEQLK | S121C | S121C | 20 |
| DEQLK<u>C</u>GTASV | S127C | S127C | 21 |
| VTEQD<u>C</u>KDSTY | S168C | S168C | 22 |
| GLSSP<u>C</u>TKSFN | V205C | V205C | 23 |

Labelled Cysteine Engineered Anti-TENB2 Antibodies

Cysteine engineered anti-TENB2 antibodies may be site-specifically and efficiently coupled with a thiol-reactive reagent. The thiol-reactive reagent may be a multifunctional linker reagent, a capture, i.e. affinity, label reagent (e.g. a biotin-linker reagent), a detection label (e.g. a fluorophore reagent), a solid phase immobilization reagent (e.g. SEPHAROSE™, polystyrene, or glass), or a drug-linker intermediate. One example of a thiol-reactive reagent is N-ethyl maleimide (NEM). In an exemplary embodiment, reaction of a ThioFab with a biotin-linker reagent provides a biotinylated ThioFab by which the presence and reactivity of the engineered cysteine residue may be detected and measured. Reaction of a ThioFab with a multifunctional linker reagent provides a ThioFab with a functionalized linker which may be further reacted with a drug moiety reagent or other label. Reaction of a ThioFab with a drug-linker intermediate provides a ThioFab drug conjugate.

The exemplary methods described here may be applied generally to the identification and production of antibodies, and more generally, to other proteins through application of the design and screening steps described herein.

Such an approach may be applied to the conjugation of other thiol-reactive reagents in which the reactive group is, for example, a maleimide, an iodoacetamide, a pyridyl disulfide, or other thiol-reactive conjugation partner (Haugland, 2003, Molecular Probes Handbook of Fluorescent Probes and Research Chemicals, Molecular Probes, Inc.; Brinkley, 1992, Bioconjugate Chem. 3:2; Gannan, 1997, Non-Radioactive Labelling: A Practical Approach, Academic Press, London; Means (1990) Bioconjugate Chem. 1:2; Hemmanson, G. in Bioconjugate Techniques (1996) Academic Press, San Diego, pp. 40-55, 643-671). The thiol-reactive reagent may be a drug moiety, a fluorophore such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent.

Uses of Cysteine Engineered Anti-TENB2 Antibodies

Cysteine engineered anti-TENB2 antibodies, and conjugates thereof may find use as therapeutic and/or diagnostic agents. The present invention further provides methods of preventing, managing, treating or ameliorating one or more symptoms associated with a TENB2 related disorder. In particular, the present invention provides methods of preventing, managing, treating, or ameliorating one or more symptoms associated with a cell proliferative disorder, such as cancer, e.g., ovarian cancer, cervical cancer, uterine cancer, pancreatic cancer, lung cancer and breast cancer. The present invention still further provides methods for diagnosing a TENB2 related disorder or predisposition to developing such a disorder, as well as methods for identifying antibodies, and antigen-binding fragments of antibodies, that preferentially bind cell-associated TENB2 polypeptides.

Another embodiment of the present invention is directed to the use of a cysteine engineered anti-TENB2 antibody for the preparation of a medicament useful in the treatment of a condition which is responsive to a TENB2 related disorder.

Cysteine Engineered Anti-TENB2 Antibody Drug Conjugates

Another aspect of the invention is an antibody-drug conjugate compound comprising a cysteine engineered anti-TENB2 antibody (Ab), and an auristatin drug moiety (D) wherein the cysteine engineered antibody is attached through one or more free cysteine amino acids by a linker moiety (L) to D; the compound having Formula I:

$$\text{Ab-(L-D)}_p \qquad \qquad \text{I}$$

where p is 1, 2, 3, or 4; and wherein the cysteine engineered antibody is prepared by a process comprising replacing one or more amino acid residues of a parent anti-TENB2 antibody by one or more free cysteine amino acids.

FIG. 5 shows embodiments of cysteine engineered anti-TENB2 antibody drug conjugates (ADC) where an auristatin drug moiety is attached to an engineered cysteine group in: the light chain (LC-ADC); the heavy chain (HC-ADC); and the Fc region (Fc-ADC).

Potential advantages of cysteine engineered anti-TENB2 antibody drug conjugates include improved safety (larger therapeutic index), improved PK parameters, the antibody interchain disulfide bonds are retained which may stabilize the conjugate and retain its active binding conformation, the sites of drug conjugation are defined, and the preparation of cysteine engineered antibody drug conjugates from conjugation of cysteine engineered antibodies to drug-linker reagents results in a more homogeneous product.

Drug Moieties

Auristatin drug moieties of the antibody-drug conjugates (ADC) of Formula I include dolastatins, auristatins (U.S. Pat. No. 5,635,483; U.S. Pat. No. 5,780,588; U.S. Pat. No. 5,767,237; U.S. Pat. No. 6,124,431), and analogs and derivatives thereof. Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). Various forms of a dolastatin or auristatin drug moiety may be covalently attached to an antibody through the N (amino) terminus or the C (carboxyl) terminus of the peptidic drug moiety (WO 02/088172; Doronina et al (2003) Nature Biotechnology 21(7):778-784; Francisco et al (2003) Blood 102 (4):1458-1465).

Exemplary auristatin embodiments include the N-terminus linked monomethylauristatin drug moieties DE and DF, disclosed in: WO 2005/081711; Senter et al, Proceedings of the American Association for Cancer Research, Volume 45, Abstract Number 623, presented Mar. 28, 2004, the disclosure of each which are expressly incorporated by reference in their entirety. Exemplary auristatin drug moieties include MMAE, and MMAF.

The auristatin drug moiety (D) of the antibody-drug conjugates (ADC) of Formula I include the monomethylauristatin drug moieties MMAE and MMAF. The N-terminus of the MMAE or MMAF drug moiety is covalently attached via a linker to a engineered cysteine of the antibody.

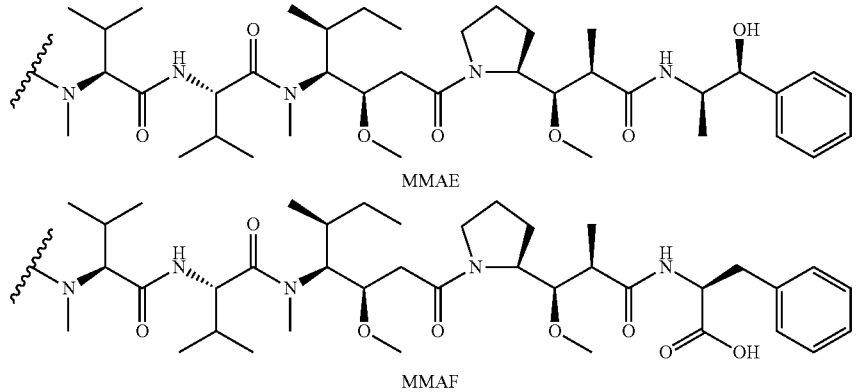

MMAE

MMAF

Other exemplary auristatin drug moieties include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry.

Linkers

"Linker", "Linker Unit", or "link" means a chemical moiety comprising a covalent bond or a chain of atoms that covalently attaches an antibody to a drug moiety. In various embodiments, a linker is specified as L. A "Linker" (L) is a bifunctional or multifunctional moiety which can be used to link one or more Drug moieties (D) and an antibody unit (Ab) to form antibody-drug conjugates (ADC) of Formula I. Antibody-drug conjugates (ADC) can be conveniently prepared using a Linker having reactive functionality for binding to the Drug and to the Antibody. A cysteine thiol of a cysteine engineered antibody (Ab) can form a bond with an electrophilic functional group of a linker reagent, a drug moiety or drug-linker intermediate.

In one aspect, a Linker has a reactive site which has an electrophilic group that is reactive to a nucleophilic cysteine present on an antibody. The cysteine thiol of the antibody is reactive with an electrophilic group on a Linker and forms a covalent bond to a Linker. Useful electrophilic groups include, but are not limited to, maleimide and haloacetamide groups.

Linkers include a divalent radical such as an alkyldiyl, an arylene, a heteroarylene, moieties such as: $-(CR_2)_n$ $O(CR_2)_n-$, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

Cysteine engineered antibodies react with linker reagents or drug-linker intermediates, with electrophilic functional groups such as maleimide or α-halo carbonyl, according to the conjugation method at page 766 of Klussman, et al (2004), Bioconjugate Chemistry 15(4):765-773, and according to the protocol of Example 3.

The linker may be composed of one or more linker components. Exemplary linker components include 6-maleimidocaproyl ("MC"), maleimidopropanoyl ("MP"), valine-citrulline ("val-cit" or "vc"), alanine-phenylalanine ("ala-phe" or "af"), p-aminobenzyloxycarbonyl ("PAB"), N-succinimidyl 4-(2-pyridylthio) pentanoate ("SPP"), N-succinimidyl 4-(N-maleimidomethyl)cyclohexane-1 carboxylate ("SMCC"), N-Succinimidyl (4-iodo-acetyl)aminobenzoate ("SIAB"), ethyleneoxy —CH$_2$CH$_2$O— as one or more repeating units ("EO" or "PEO"). Additional linker components are known in the art and some are described herein.

In one embodiment, linker L of an ADC has the formula:

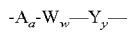

wherein:
-A- is a Stretcher unit covalently attached to a cysteine thiol of the antibody (Ab);
a is 0 or 1;
each —W— is independently an Amino Acid unit;
w is independently an integer ranging from 0 to 12;
—Y— is a Spacer unit covalently attached to the drug moiety; and
y is 0, or 2.

Stretcher Unit

The Stretcher unit (-A-), when present, is capable of linking an antibody unit to an amino acid unit (—W—). In this regard an antibody (Ab) has a free cysteine thiol group that can form a bond with an electrophilic functional group of a Stretcher Unit. Exemplary stretcher units in Formula I conjugates are depicted by Formulas II and III, wherein Ab-, —W—, —Y—, -D, w and y are as defined above, and R$^{17}$ is a divalent radical selected from $(CH_2)_r$, C$_3$-C$_8$ carbocyclyl, O—(CH$_2$)$_r$, arylene, (CH$_2$)$_r$-arylene, -arylene-(CH$_2$)$_r$—, (CH$_2$)$_r$—(C$_3$-C$_8$ carbocyclyl), (C$_3$-C$_8$ carbocyclyl)-(CH$_2$)$_r$, C$_3$-C$_8$ heterocyclyl, (CH$_2$)$_r$—(C$_3$-C$_8$ heterocyclyl), —(C$_3$-C$_8$ heterocyclyl)-(CH$_2$)$_r$—, —(CH$_2$)$_r$C(O)NR$^b$(CH$_2$)$_r$—, —(CH$_2$CH$_2$O)$_r$—, —(CH$_2$C$_{1-20}$)$_r$, CH$_2$—, —(CH$_2$)$_r$C(O) NR$^b$(CH$_2$CH$_2$O)$_r$—, —(CH$_2$)$_r$C(O)NR$^b$(CH$_2$CH$_2$O)$_r$ CH$_2$—, —(CH$_2$CH$_2$O)$_r$C(O)NR$^b$(CH$_2$CH$_2$O)$_r$—, —(CH$_2$CH$_2$O)$_r$C(O)NR$^b$(CH$_2$CH$_2$O)$_r$CH$_2$—, and —(CH$_2$CH$_2$O)$_r$C(O)NR$^b$(CH$_2$)$_r$—; where R$^b$ is H, C$_1$-C$_6$ alkyl, phenyl, or benzyl; and r is independently an integer ranging from 1-10.

Arylene includes divalent aromatic hydrocarbon radicals of 6-20 carbon atoms derived by the removal of two hydrogen atoms from the aromatic ring system. Typical arylene groups include, but are not limited to, radicals derived from benzene, substituted benzene, naphthalene, anthracene, biphenyl, and the like.

Heterocyclyl groups include a ring system in which one or more ring atoms is a heteroatom, e.g. nitrogen, oxygen, and sulfur. The heterocycle radical comprises 1 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4Ah-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

Carbocyclyl groups include a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

It is to be understood from all the exemplary embodiments of Formula I ADC such as II-V, that even where not denoted expressly, from 1 to 4 drug moieties are linked to an antibody (p=1-4), depending on the number of engineered cysteine residues.

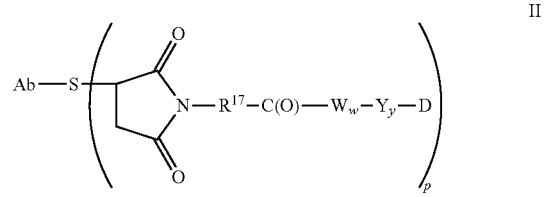

An illustrative Formula II Stretcher unit is derived from maleimido-caproyl (MC) wherein R$^{17}$ is —(CH$_2$)$_5$—:

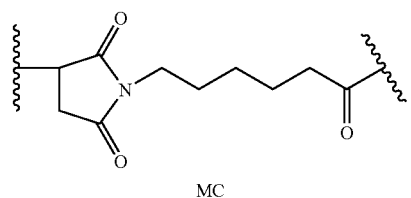 [SMILES: *C(=O)CCCCCN1C(=O)CC(*)C1=O]

MC

An illustrative Stretcher unit of Formula II, and is derived from maleimido-propanoyl (MP) wherein R$^{17}$ is —(CH$_2$)$_2$—:

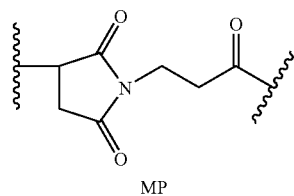

MP

Another illustrative Stretcher unit of Formula II wherein R$^{17}$ is —(CH$_2$CH$_2$O)$_r$—CH$_2$— and r is 2:

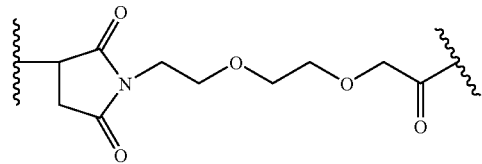

Another illustrative Stretcher unit of Formula II wherein R$^7$ is —(CH$_2$)$_r$C(O)NR$^b$(CH$_2$CH$_2$O)$_r$—CH$_2$— where R$^b$ is H and each r is 2:

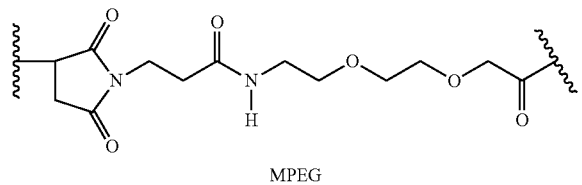

MPEG

Ab—S—(CH$_2$—CONH—R$^{17}$—C(O)—W$_w$-Y$_y$—D)$_p$     III

An illustrative Stretcher unit of Formula III wherein R$^{17}$ is —(CH$_2$)$_5$—:

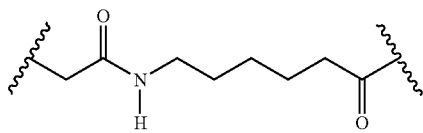

In another embodiment, the Stretcher unit is linked to the cysteine engineered anti-TENB2 antibody via a disulfide bond between the engineered cysteine sulfur atom of the antibody and a sulfur atom of the Stretcher unit. A representative Stretcher unit of this embodiment is depicted by Formula IV, wherein $R^7$, Ab-, —W—, —Y—, -D, w and y are as defined above.

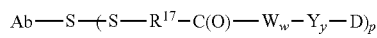
                                                                         IV In yet another embodiment, the reactive group of the Stretcher contains a thiol-reactive functional group that can form a bond with a free cysteine thiol of an antibody. Examples of thiol-reaction functional groups include, but are not limited to, maleimide, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted by Formulas Va and Vb, wherein —$R^{17}$—, Ab-, —W—, —Y—, -D, w and y are as defined above;

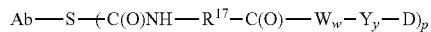
                                                                          Va
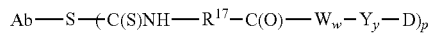
                                                                          Vb In another embodiment, the linker may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768; King (2002) Tetrahedron Letters 43:1987-1990). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker.

Amino Acid Unit

The linker may comprise amino acid residues. The Amino Acid unit (—$W_w$—), when present, links the antibody (Ab) to the drug moiety (D) of the cysteine engineered antibody-drug conjugate (ADC) of the invention.

—$W_w$— is a dipeptide, tripeptide, tetrapeptide, pentapeptide, hexapeptide, heptapeptide, octapeptide, nonapeptide, decapeptide, undecapeptide or dodecapeptide unit. Amino acid residues which comprise the Amino Acid unit include those occurring naturally, as well as minor amino acids and non-naturally occurring amino acid analogs, such as citrulline. Each —W— unit independently has the formula denoted below in the square brackets, and w is an integer ranging from 0 to 12:

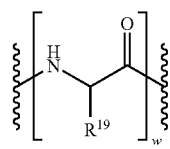

wherein $R^{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC$ (=NH)$NH_2$, —$(CH_2)_3NH_2$, —$(CH_2)_3NHCOCH_3$, —$(CH_2)_3$ NHCHO, —$(CH_2)_4NHC$(=NH)$NH_2$, —$(CH_2)_4$ $NH_2$, —$(CH_2)_4NHCOCH_3$, —$(CH_2)_4NHCHO$, —$(CH_2)_3$ NHCONH$_2$, —$(CH_2)_4NHCONH_2$, —$CH_2CH_2CH(OH)$ $CH_2NH_2$, 2-pyridylmethyl-, 3-pyridylmethyl-, 4-pyridylmethyl-, phenyl, cyclohexyl,

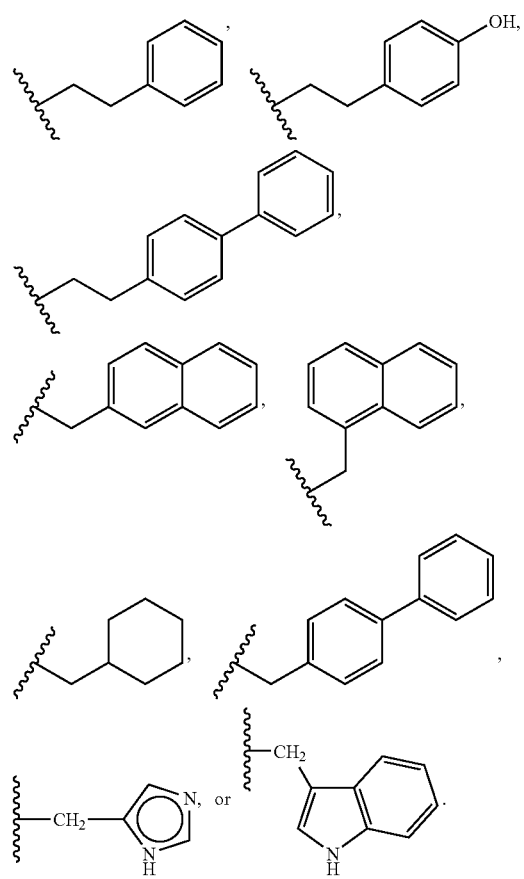

When $R^{19}$ is other than hydrogen, the carbon atom to which $R^{19}$ is attached is chiral. Each carbon atom to which $R^{19}$ is attached is independently in the (S) or (R) configuration, or a racemic mixture. Amino acid units may thus be enantiomerically pure, racemic, or diastereomeric.

Exemplary —$W_w$— Amino Acid units include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline.

The Amino Acid unit can be enzymatically cleaved by one or more enzymes, including a tumor-associated protease, to liberate the Drug moiety (-D), which in one embodiment is protonated in vivo upon release to provide a Drug (D). Amino acid linker components can be designed and optimized in their selectivity for enzymatic cleavage by a particular enzymes, for example, a tumor-associated protease, cathepsin B, C and D, or a plasmin protease.

Spacer Unit

The Spacer unit (—$Y_y$—), when present (y=1 or 2), links an Amino Acid unit (—$W_w$—) to the drug moiety (D) when an Amino Acid unit is present (w=1-12). Alternately, the Spacer unit links the Stretcher unit to the Drug moiety when the Amino Acid unit is absent. The Spacer unit also links the drug moiety to the antibody unit when both the Amino Acid unit and Stretcher unit are absent (w, y=0). Spacer units are of two general types: self-immolative and non self-immolative. A non self-immolative Spacer unit is one in which part or all of the Spacer unit remains bound to the Drug moiety after cleavage, particularly enzymatic, of an Amino Acid unit from the antibody-drug conjugate or the Drug moiety-linker. When an ADC containing a glycine-glycine Spacer unit or a glycine Spacer unit undergoes enzymatic cleavage via a tumor-cell associated-protease, a cancer-cell-associated protease or a lymphocyte-associated protease, a glycine-glycine-Drug moiety or a glycine-Drug moiety is cleaved from Ab-$A_a$-Ww-. In one embodiment, an independent hydrolysis reaction takes place within the target cell, cleaving the glycine-Drug moiety bond and liberating the Drug.

In another embodiment, —$Y_y$— is a p-aminobenzylcarbamoyl (PAB) unit whose phenylene portion is substituted with $Q_m$ wherein Q is —$C_1$-$C_8$ alkyl, —O—($C_1$-$C_8$ alkyl), -halogen, -nitro or -cyano; and m is an integer ranging from 0-4.

Exemplary embodiments of a non self-immolative Spacer unit (—Y—) are: -Gly-Gly-; -Gly-; -Ala-Phe-; -Val-Cit-.

In one embodiment, a Drug moiety-linker or an ADC is provided in which the Spacer unit is absent (y=0), or a pharmaceutically acceptable salt or solvate thereof.

Alternatively, an ADC containing a self-immolative Spacer unit can release-D. In one embodiment, —Y— is a PAB group that is linked to —$W_w$— via the amino nitrogen atom of the PAB group, and connected directly to -D via a carbonate, carbamate or ether group, where the ADC has the exemplary structure:

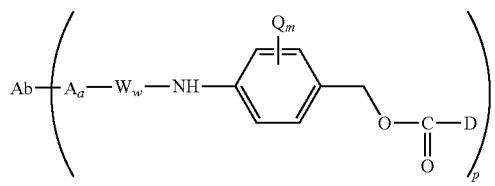

wherein Q is —$C_1$-$C_8$ alkyl, —O—($C_1$-$C_8$ alkyl), -halogen, -nitro or -cyano; m is an integer ranging from 0-4; and p ranges from 1 to 4.

Other examples of self-immolative spacers include, but are not limited to, aromatic compounds that are electronically similar to the PAB group such as 2-aminoimidazol-5-methanol derivatives (Hay et al. (1999) Bioorg. Med. Chem. Lett. 9:2237), heterocyclic PAB analogs (US 2005/0256030), beta-glucuronide (WO 2007/011968), and ortho or para-aminobenzylacetals. Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Elimination of amine-containing drugs that are substituted at glycine (Kingsbury et al (1984) J. Med. Chem. 27:1447) are also examples of self-immolative spacer useful in ADCs.

Exemplary Spacer units (—$Y_y$—) are represented by Formulas X-XII:

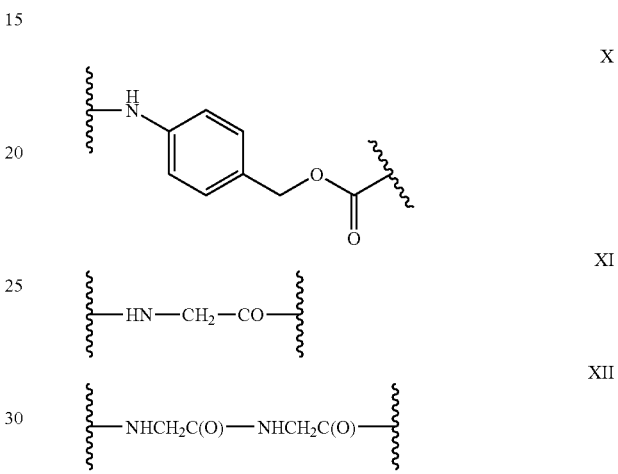

Dendritic Linkers

In another embodiment, linker L may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker. Exemplary embodiments of branched, dendritic linkers include 2,6-bis(hydroxymethyl)-p-cresol and 2,4,6-tris(hydroxymethyl)-phenol dendrimer units (WO 2004/01993; Szalai et al (2003) J. Amer. Chem. Soc. 125: 15688-15689; Shamis et al (2004) J. Amer. Chem. Soc. 126: 1726-1731; Amir et al (2003) Angew. Chem. Int. Ed. 42:4494-4499).

In one embodiment, the Spacer unit is a branched bis (hydroxymethyl)styrene (BHMS), which can be used to incorporate and release multiple drugs, having the structure:

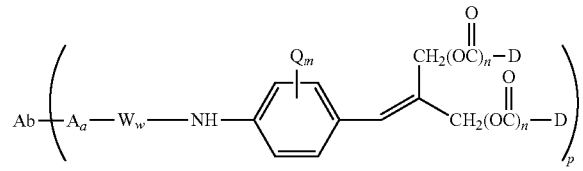

comprising a 2-(4-aminobenzylidene)propane-1,3-diol dendrimer unit (WO 2004/043493; de Groot et al (2003) Angew. Chem. Int. Ed. 42:4490-4494), wherein Q is —$C_1$-$C_8$ alkyl, —O—($C_1$-$C_8$ alkyl), -halogen, -nitro or -cyano; m is an integer ranging from 0-4; n is 0 or 1; and p ranges ranging from 1 to 4.

Exemplary embodiments of the Formula I antibody-drug conjugate compounds include XIIIa (MC), XIIIb (val-cit), XIIIc (MC-val-cit), and XIIId (MC-val-cit-PAB):

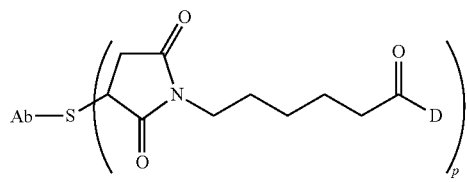
XIIIa

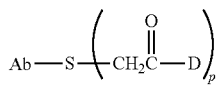
XIVc

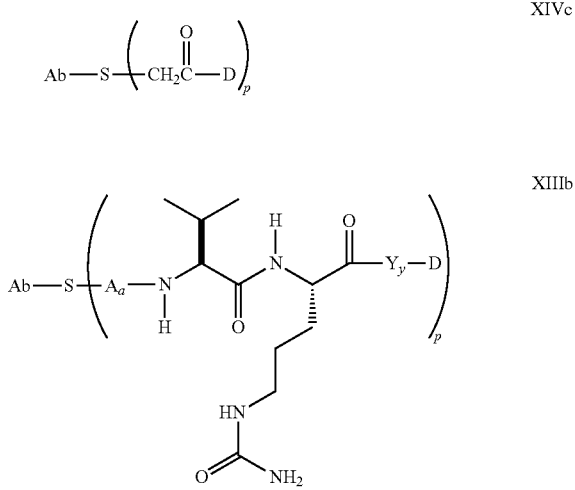
XIIIb

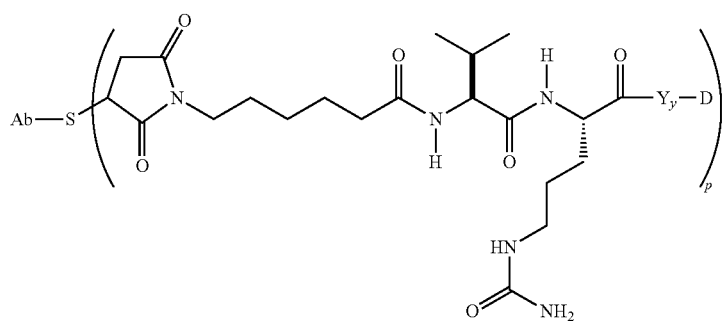
XIIIc

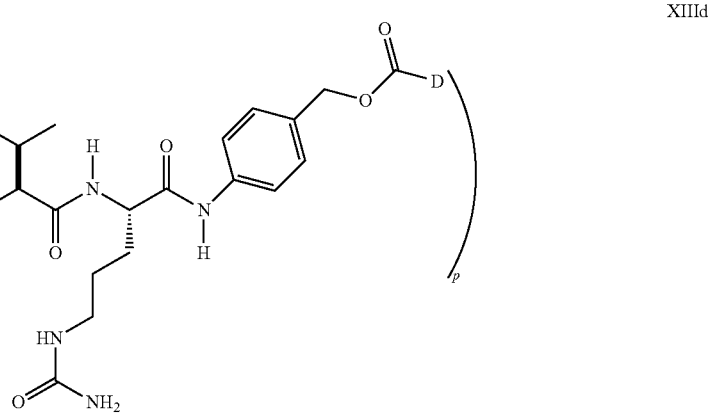
XIIId

Other exemplary embodiments of the Formula Ia antibody-drug conjugate compounds include XIVa-e:

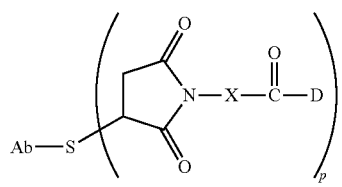
XIVa

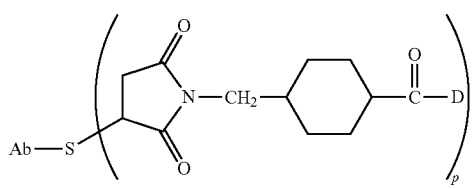
XIVd

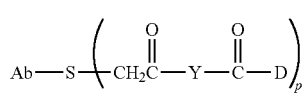
XIVb

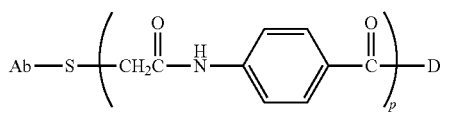
XIVe

-continued where X is:

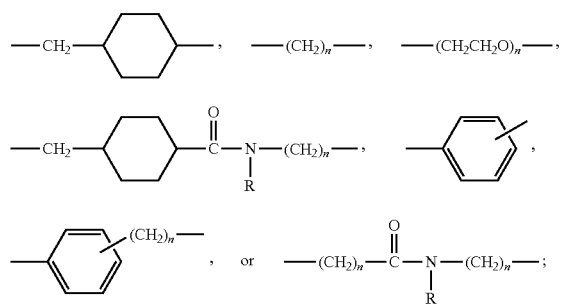

Y is:

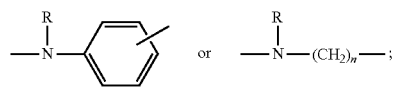

where R is independently H or $C_1$-$C_6$ alkyl; and n is 1 to 12.

In another embodiment, a Linker has a reactive functional group which has a nucleophilic group that is reactive to an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

Typically, peptide-type Linkers can be prepared by forming a peptide bond between two or more amino acids and/or peptide fragments. Such peptide bonds can be prepared, for example, according to the liquid phase synthesis method (E. Schröder and K. Lübke (1965) "The Peptides", volume 1, pp 76-136, Academic Press) which is well known in the field of peptide chemistry. Linker intermediates may be assembled with any combination or sequence of reactions including Spacer, Stretcher, and Amino Acid units. The Spacer, Stretcher, and Amino Acid units may employ reactive functional groups which are electrophilic, nucleophilic, or free radical in nature. Reactive functional groups include, but are not limited to carboxyls, hydroxyls, para-nitrophenylcarbonate, isothiocyanate, and leaving groups, such as O-mesyl, O-tosyl, —Cl, —Br, —I; or maleimide.

In another embodiment, the Linker may be substituted with groups which modulated solubility or reactivity. For example, a charged substituent such as sulfonate (—$SO_3^-$) or ammonium, may increase water solubility of the reagent and facilitate the coupling reaction of the linker reagent with the antibody or the drug moiety, or facilitate the coupling reaction of Ab-L (antibody-linker intermediate) with D, or D-L (drug-linker intermediate) with Ab, depending on the synthetic route employed to prepare the ADC.

Linker Reagents

Conjugates of the antibody and auristatin may be made using a variety of bifunctional linker reagents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

The antibody drug conjugates may also be prepared with linker reagents: BMPEO, BMPS, EMCS, GMBS, HBVS, LC-SMCC, MBS, MPBH, SBAP, SIA, SIAB, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and including bis-maleimide reagents: DTME, BMB, BMDB, BMH, BMOE, BM(PEO)$_3$, and BM(PEO)$_4$, which are commercially available from Pierce Biotechnology, Inc., P.O. Box 117, Rockford, Ill. 61105, USA. Bis-maleimide reagents allow the attachment of the thiol group of a cysteine engineered antibody to a thiol-containing drug moiety, label, or linker intermediate, in a sequential or concurrent fashion. Other functional groups besides maleimide, which are reactive with a thiol group of a cysteine engineered antibody, drug moiety, label, or linker intermediate include iodoacetamide, bromoacetamide, vinyl pyridine, disulfide, pyridyl disulfide, isocyanate, and isothiocyanate.

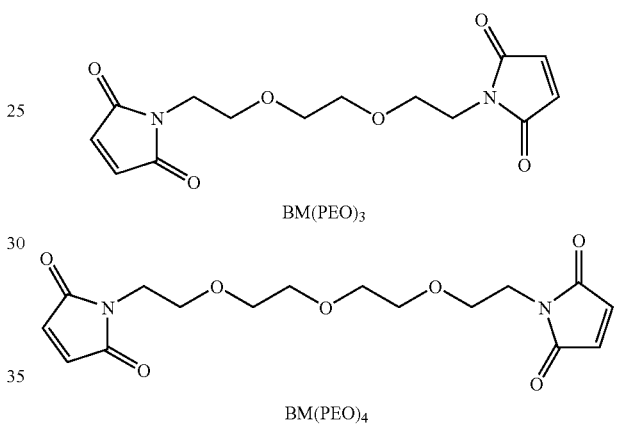

BM(PEO)$_3$

BM(PEO)$_4$

Useful linker reagents can also be obtained via other commercial sources, such as Molecular Biosciences Inc. (Boulder, Colo.), or synthesized in accordance with procedures described in Toki et al (2002) J. Org. Chem. 67:1866-1872; Walker, M. A. (1995) J. Org. Chem. 60:5352-5355; Frisch et al (1996) Bioconjugate Chem. 7:180-186; U.S. Pat. No. 6,214,345; WO 02/088172; US 2003130189; US2003096743; WO 03/026577; WO 03/043583; and WO 04/032828.

Stretchers of formula (IIa) can be introduced into a Linker by reacting the following linker reagents with the N-terminus of an Amino Acid unit:

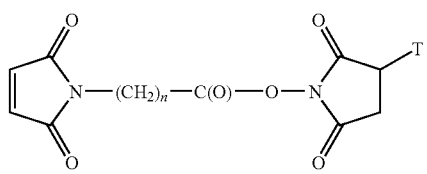

where n is an integer ranging from 1-10 and T is —H or —$SO_3$Na;

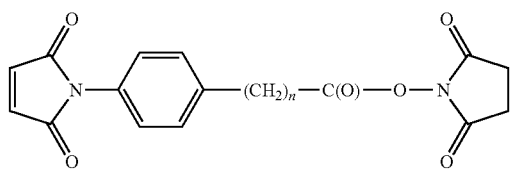

where n is an integer ranging from 0-3;

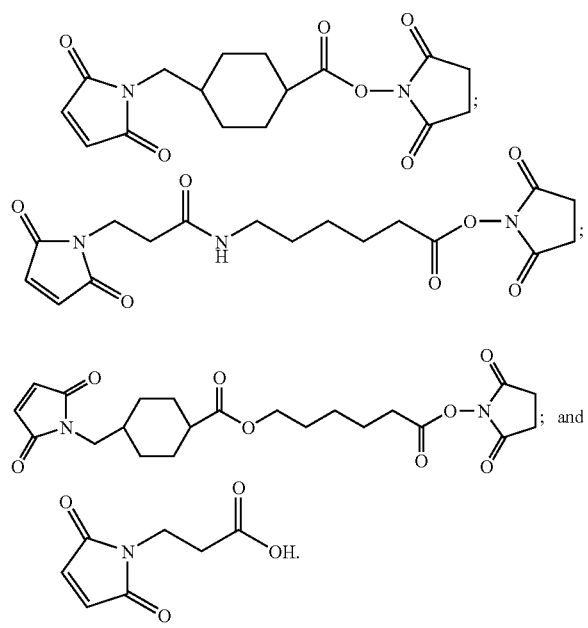

Stretcher units of can be introduced into a Linker by reacting the following bifunctional reagents with the N-terminus of an Amino Acid unit:

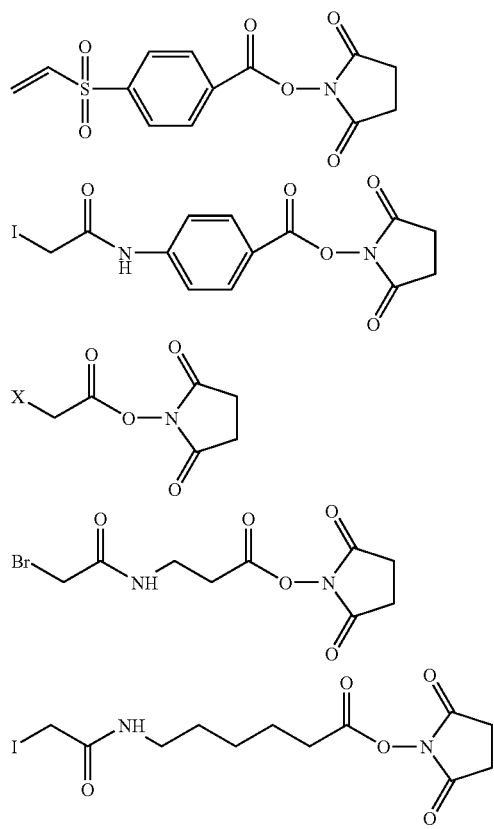

where X is Br or I.

Stretcher units of formula can also be introduced into a Linker by reacting the following bifunctional reagents with the N-terminus of an Amino Acid unit:

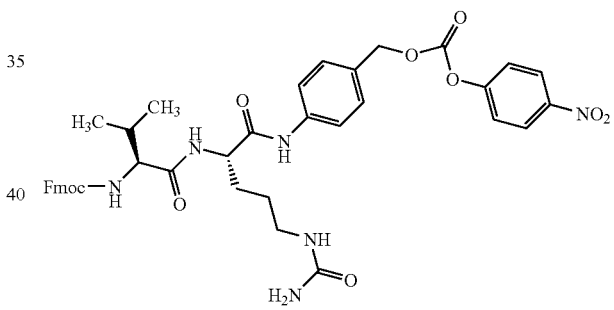

An exemplary valine-citrulline (val-cit or vc) dipeptide linker reagent having a maleimide Stretcher and a para-aminobenzylcarbamoyl (PAB) self-immolative Spacer has the structure:

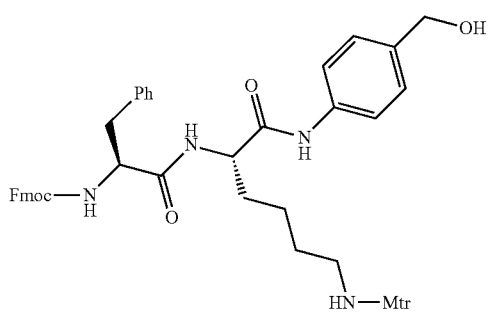

An exemplary phe-lys(Mtr, mono-4-methoxytrityl) dipeptide linker reagent having a maleimide Stretcher unit and a PAB self-immolative Spacer unit can be prepared according to Dubowchik, et al. (1997) Tetrahedron Letters, 38:5257-60, and has the structure:

Exemplary drug-linker intermediates include:
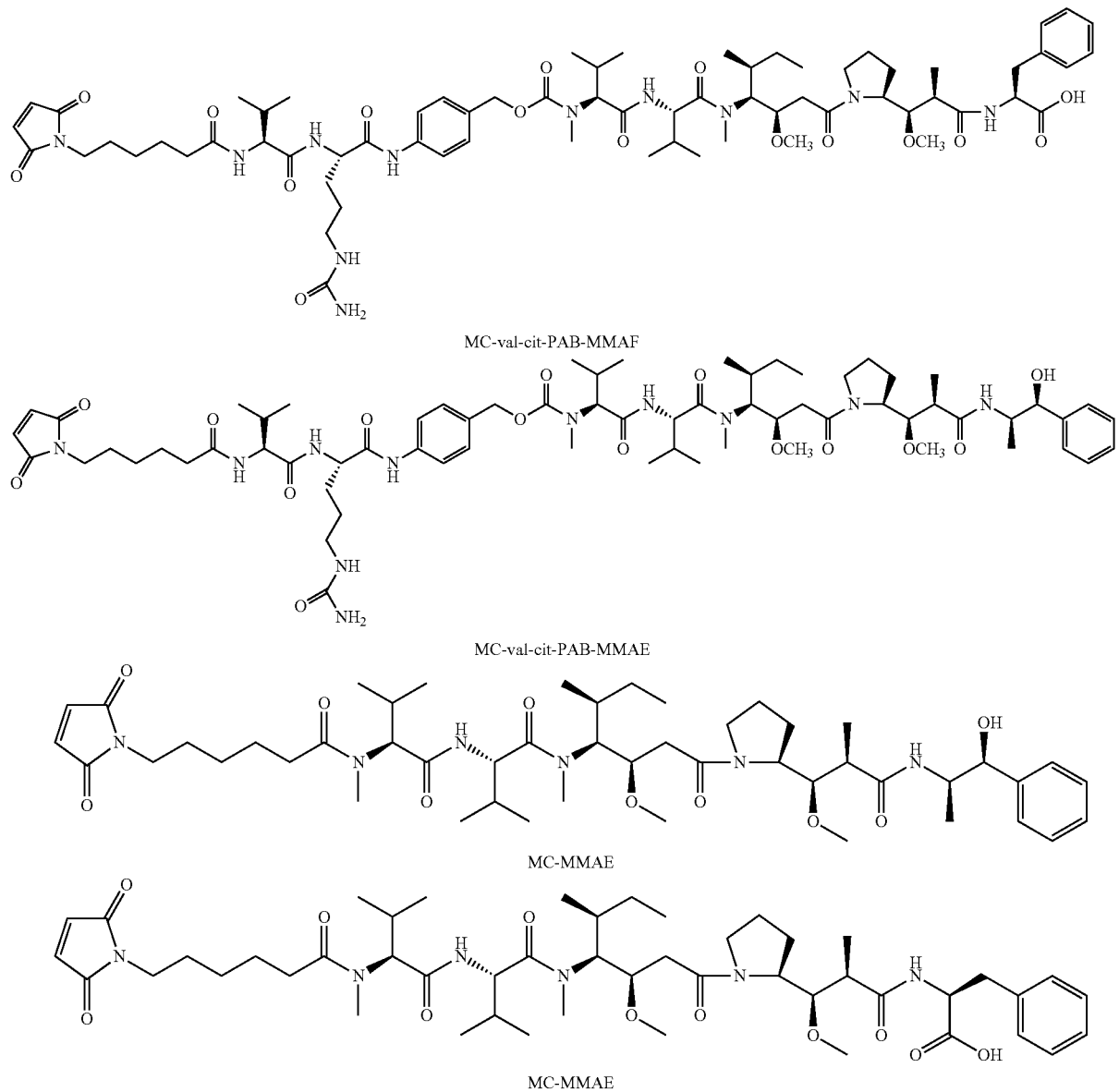
Exemplary antibody-drug conjugate compounds of the invention include:
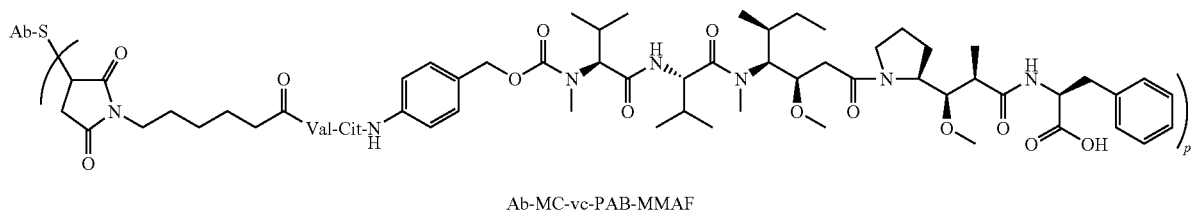

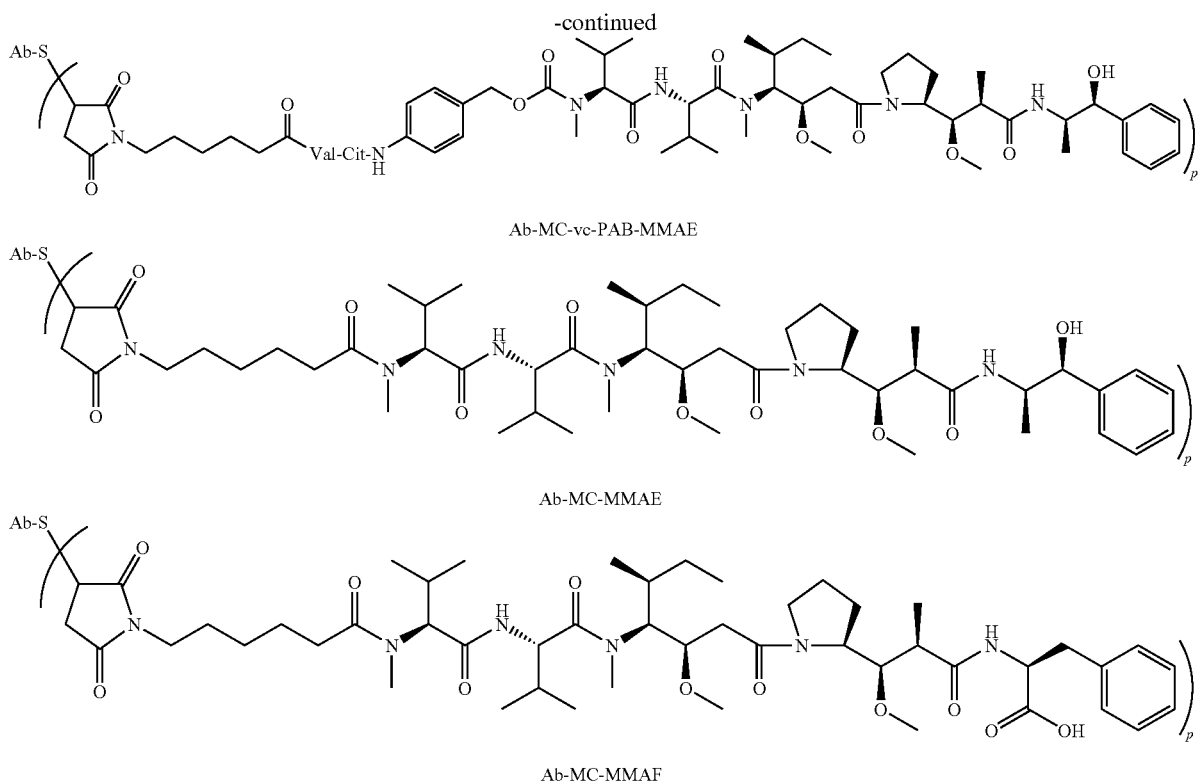

Ab-MC-vc-PAB-MMAE

Ab-MC-MMAE

Ab-MC-MMAF where Val is valine; Cit is citrulline; p is 1, 2, 3, or 4; and Ab is a cysteine engineered anti-TENB2 antibody.

Preparation of Cysteine Engineered Anti-TENB2 Antibody-Drug Conjugates

The ADC of Formula I may be prepared by several routes, employing organic chemistry reactions, conditions, and reagents known to those skilled in the art, including: (1) reaction of a cysteine group of a cysteine engineered antibody with a linker reagent, to form antibody-linker intermediate Ab-L, via a covalent bond, followed by reaction with an activated drug moiety D; and (2) reaction of a nucleophilic group of a drug moiety with a linker reagent, to form drug-linker intermediate D-L, via a covalent bond, followed by reaction with a cysteine group of a cysteine engineered antibody. Conjugation methods (1) and (2) may be employed with a variety of cysteine engineered antibodies, drug moieties, and linkers to prepare the antibody-drug conjugates of Formula I.

Antibody cysteine thiol groups are nucleophilic and capable of reacting to form covalent bonds with electrophilic groups on linker reagents and drug-linker intermediates including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Cysteine engineered antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.), followed by reoxidation to reform interchain and intrachain disulfide bonds (Example 2). For example, full length, cysteine engineered monoclonal antibodies (ThioMabs) expressed in CHO cells are reduced with about a 50 fold excess of TCEP for 3 hrs at 37° C. to reduce disulfide bonds in cysteine adducts which may form between the newly introduced cysteine residues and the cysteine present in the culture media. The reduced ThioMab is diluted and loaded onto HiTrap S column in 10 mM sodium acetate, pH 5, and eluted with PBS containing 0.3M sodium chloride. Disulfide bonds were reestablished between cysteine residues present in the parent Mab with dilute (200 nM) aqueous copper sulfate ($CuSO_4$) at room temperature, overnight. Alternatively, dehydroascorbic acid (DHAA) is an effective oxidant to reestablish the intrachain disulfide groups of the cysteine engineered antibody after reductive cleavage of the cysteine adducts. Other oxidants, i.e. oxidizing agents, and oxidizing conditions, which are known in the art may be used. Ambient air oxidation is also effective. This mild, partial reoxidation step forms intrachain disulfides efficiently with high fidelity and preserves the thiol groups of the newly introduced cysteine residues. An approximate 3 fold excess of drug-linker intermediate, e.g. MC-vc-PAB-MMAE, relative to antibody (about 1.5 fold excess relative to newly introduced cysteine residues) was added, mixed, and let stand for about an hour at room temperature to effect conjugation and form the TMEFF2#19 anti-TENB2 antibody-drug conjugate. The conjugation mixture was gel filtered and loaded and eluted through a HiTrap S column to remove excess drug-linker intermediate and other impurities.

Figure 6:
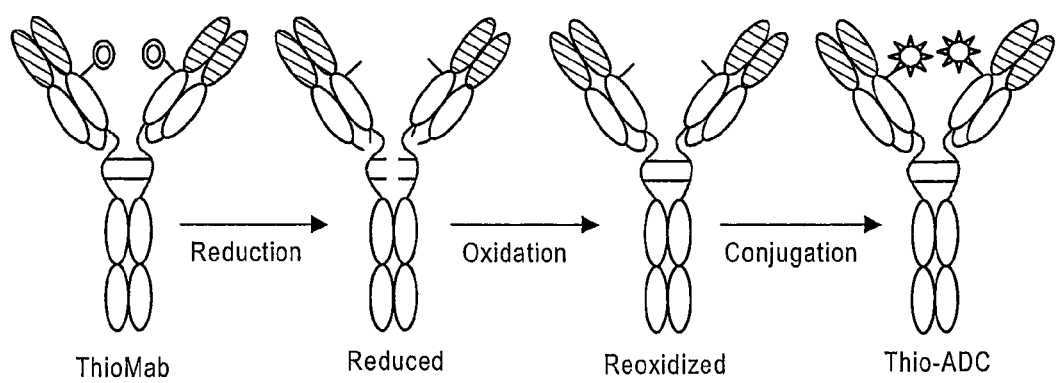
FIG. 6 shows the steps of: (i) reducing cysteine disulfide adducts and interchain and intrachain disulfides in a cysteine engineered anti-TENB2 antibody (ThioMab); (ii) partially oxidizing, i.e. reoxidation to reform interchain and intrachain disulfides; and (iii) conjugation of the reoxidized antibody with a drug-linker intermediate to form a cysteine engineered anti-TENB2 antibody drug conjugate (ADC).
Figure 7:
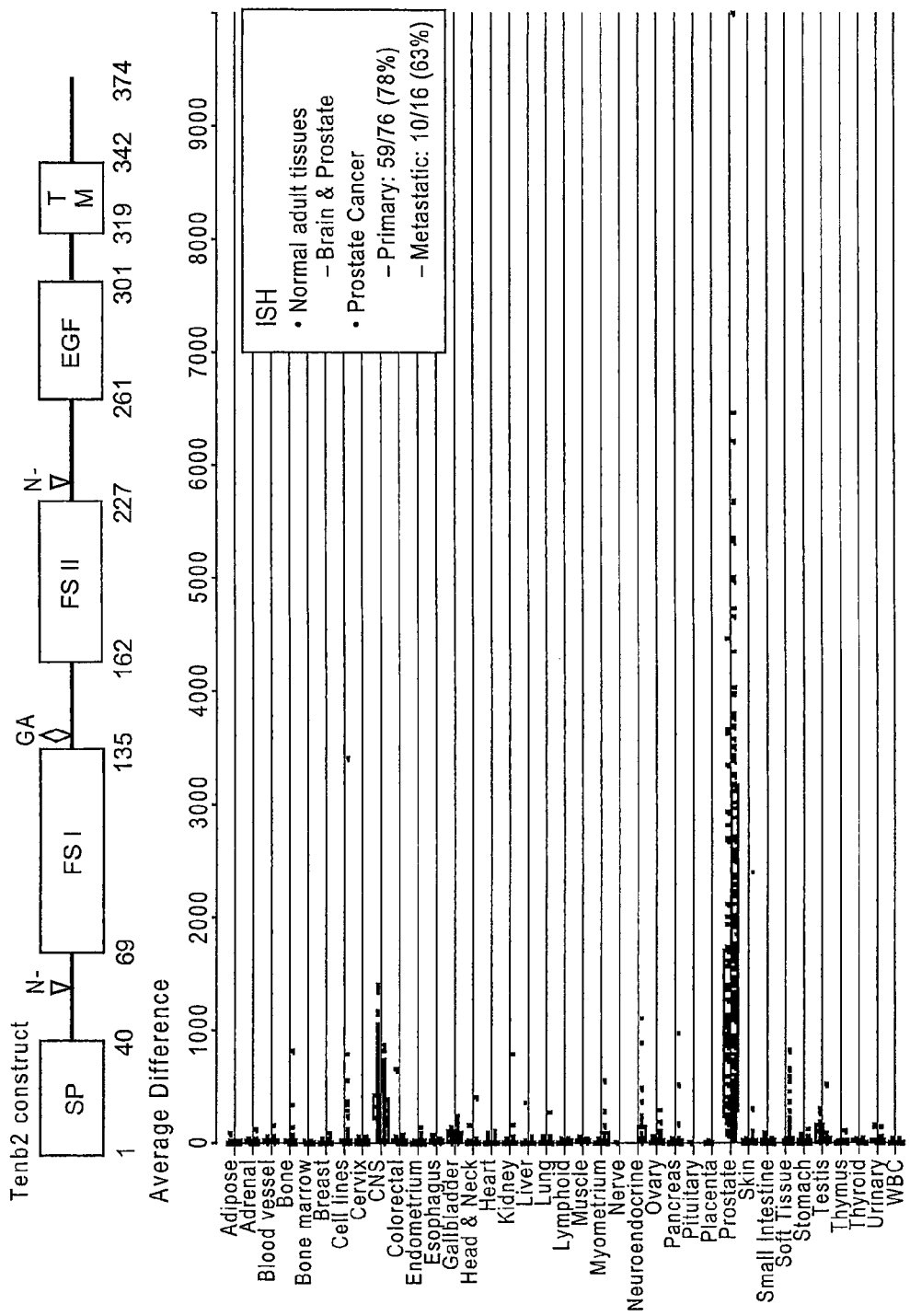
FIG. 7 shows expression of TENB2 in cancer and normal human tissues: oligonucleotide microarray analysis was performed on RNA extracted from 4841 human tissue samples. Each box in the plot provides signal intensity (average difference scaled to 100) for TENB2 for a sample of the indicated tissue. Green boxes are normal tissue, red boxes are tumors, and blue boxes represent other diseased tissues.
Figure 8:
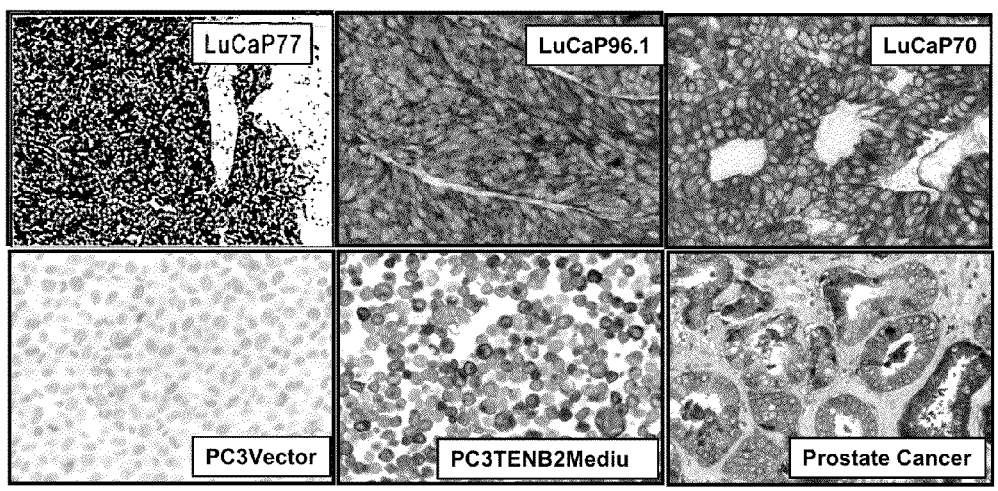
FIG. 8 shows TENB2 expression in human prostate tumors: Top and bottom panels are from human prostate explant models, PC3TENB2 medium stable cell line with vector control and prostate tumor, respectively.
Figure 10A:
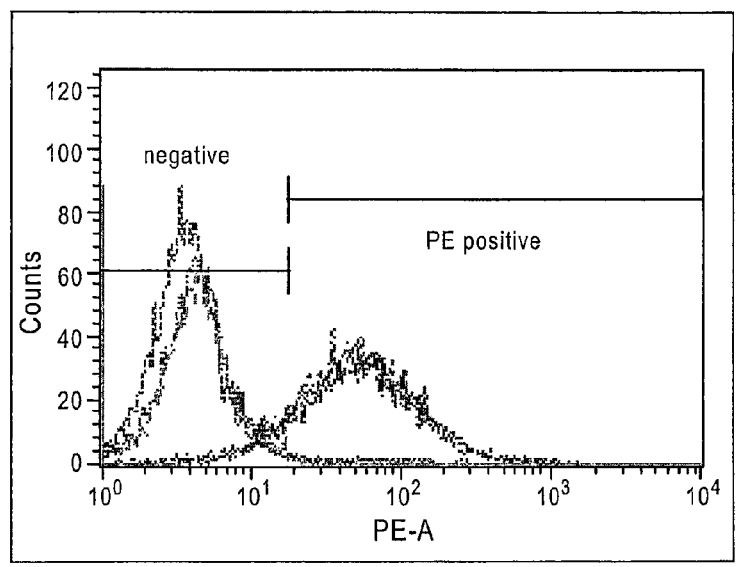
FIG. 10 shows FACS data on PC3 TENB2 Medium cells with thio (FIG. 10B) or conventional anti-TENB2 ADC treatment (FIG. 10A).
Figure 10B:
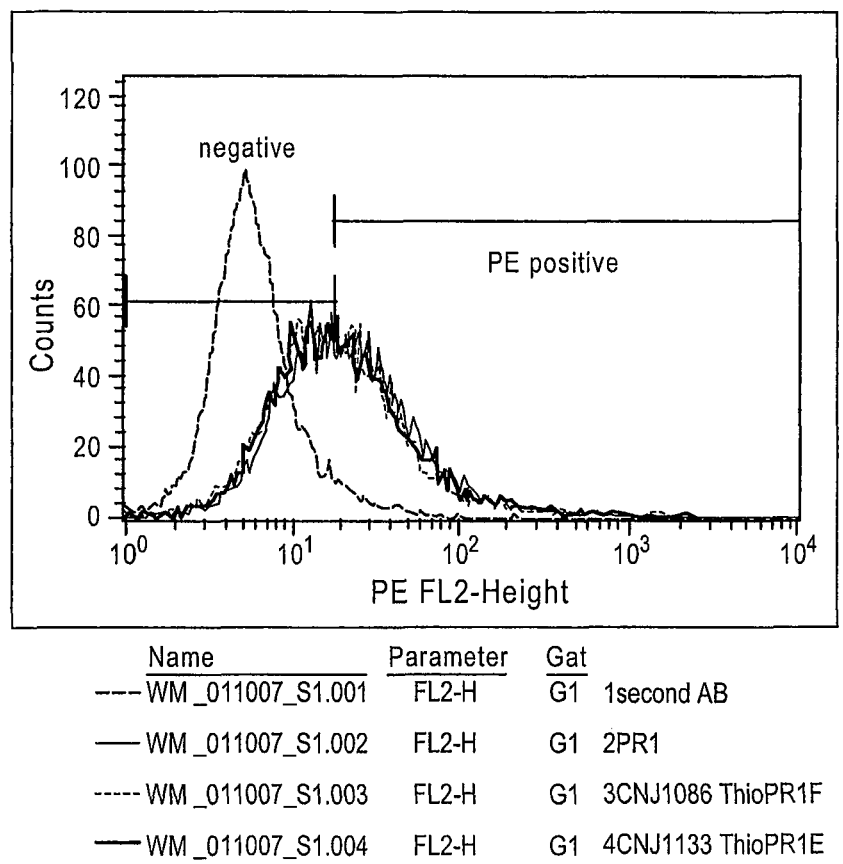
Figure 11B:
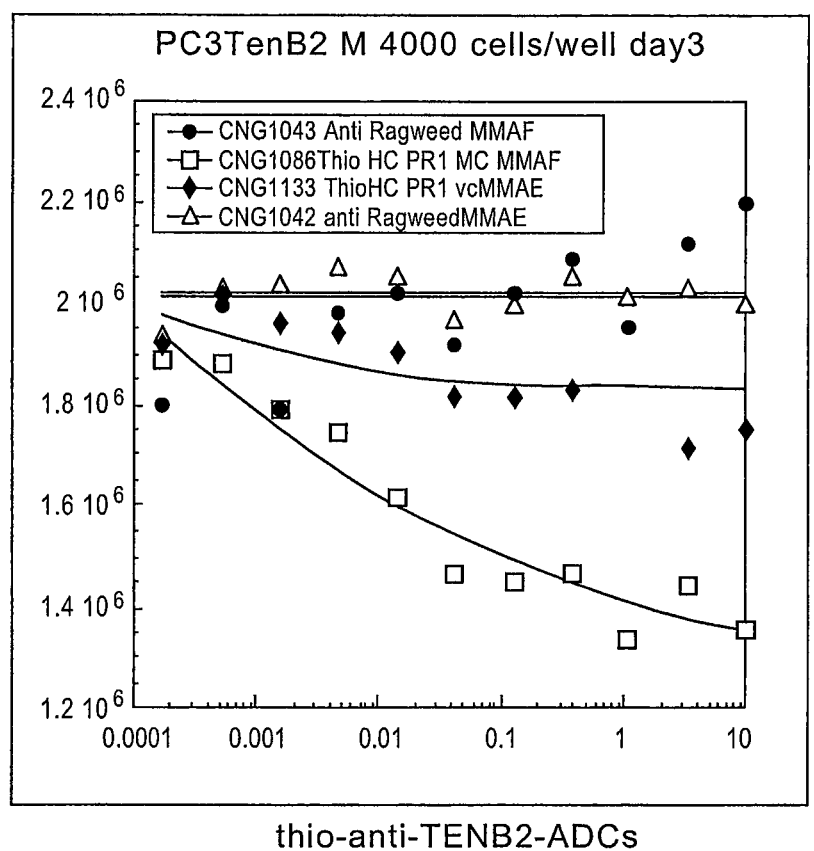
FIG. 11 shows a cell killing assay on PC3 TENB2 Medium cells with conventional anti-TENB2 (FIG. 11A) and thio-anti-TENB2 ADCs (FIG. 11B).
Figure 12:
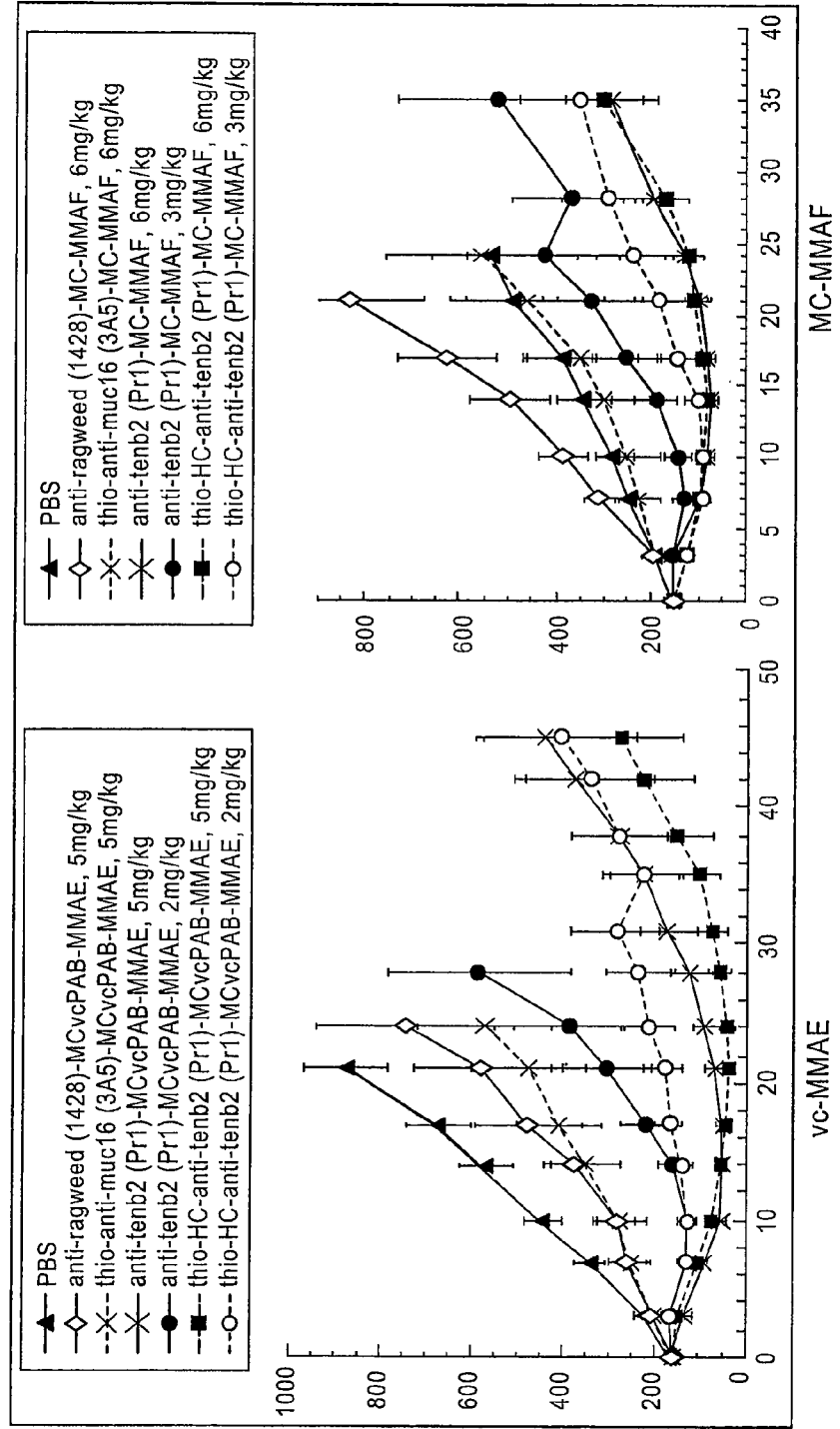
FIG. 12 shows an efficacy study on PC3 TENB2 Medium cells using anti-TENB2 and thio-anti-TENB2 ADCs (conjugated with vc-MMAE or MC-MMAF).
Figure 13:
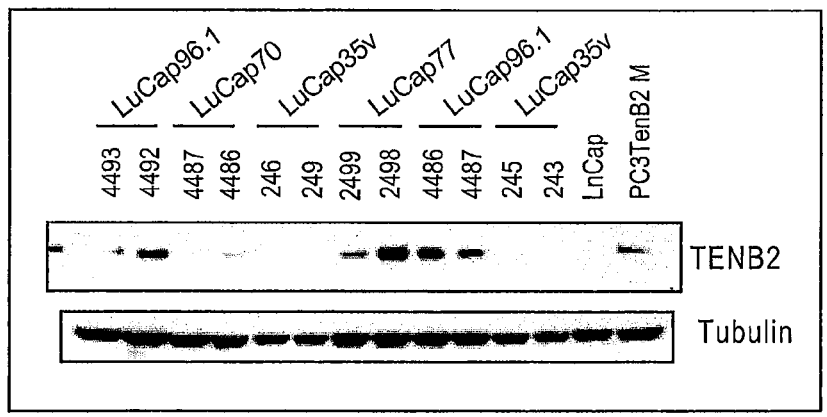
FIG. 13 shows a Western Blot with various LuCaP explant tumor tissues using humanized anti-TENB2 Ab (hu TMEFF2#19).
Figure 14:
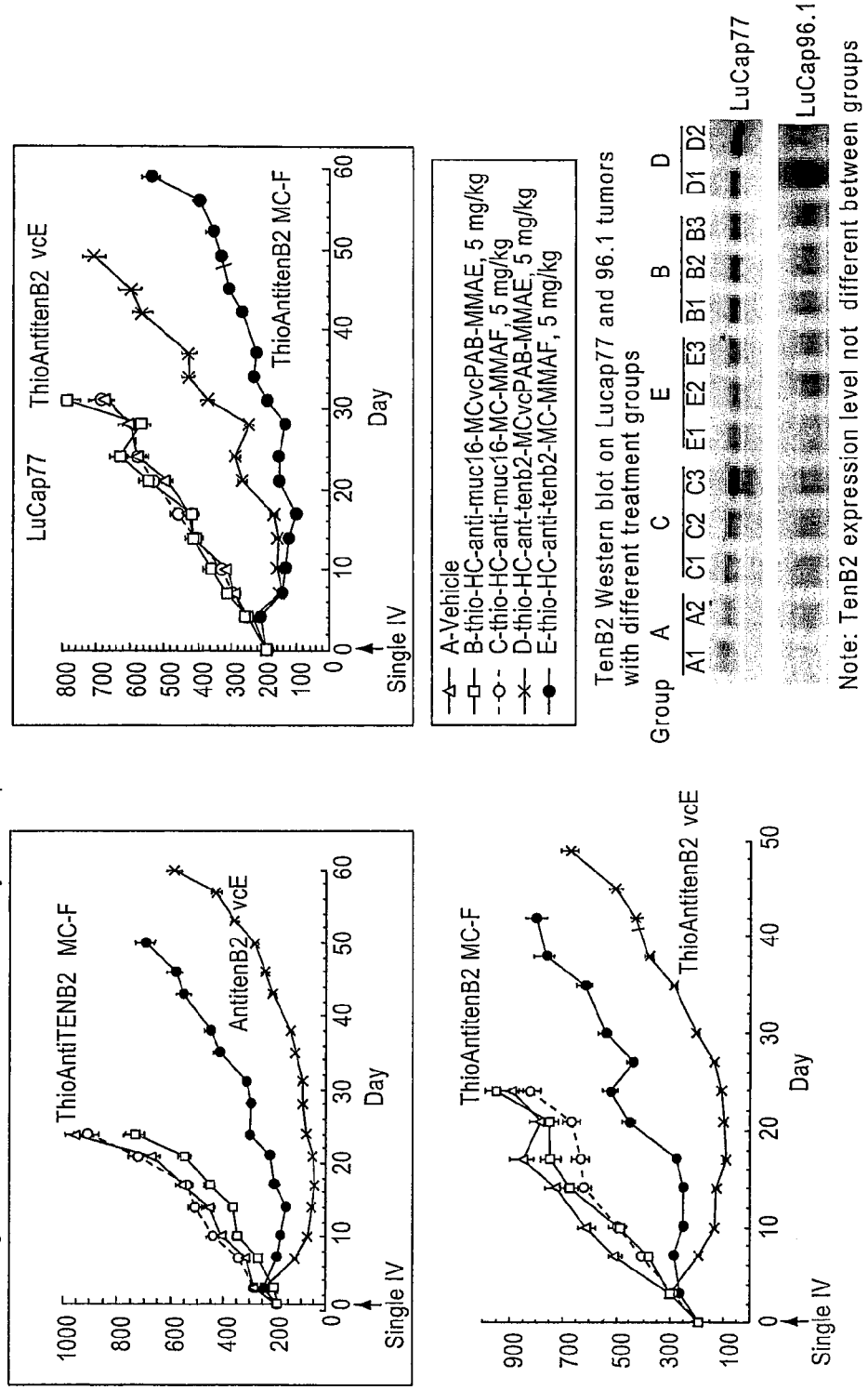
FIG. 14 shows xenograft experiments using human prostate cancer LuCaP 70, 77 and 96.1.

FIG. 6 shows the general process to prepare a cysteine engineered antibody expressed from cell culture for conjugation. When the cell culture media contains cysteine, disulfide adducts can form between the newly introduced cysteine amino acid and cysteine from media. These cysteine adducts, depicted as a circle in the exemplary ThioMab (left) in FIG. 6, must be reduced to generate cysteine engineered antibodies reactive for conjugation. Cysteine adducts, presumably along with various interchain disulfide bonds, are reductively cleaved to give a reduced form of the antibody with reducing agents such as TCEP. The interchain disulfide bonds between paired cysteine residues are reformed under partial oxidation conditions with copper sulfate, DHAA, or exposure to ambient oxygen. The newly introduced, engineered, and unpaired cysteine residues remain available for reaction with linker reagents or drug-linker intermediates to form the antibody conjugates of the invention. The ThioMabs expressed in mammalian cell lines result in externally conjugated Cys adduct to an engineered Cys through —S—S— bond formation. Hence the purified ThioMabs are treated with the reduction and reoxidation procedures as described in Example 2 to produce reactive ThioMabs. These ThioMabs are used to conjugate with maleimide containing cytotoxic drugs, fluorophores, and other labels.

Analysis of cysteine engineered antibody drug conjugate reactions show decreased heterogeneity relative to antibody drug conjugates prepared by reduction of interchain or intrachain disulfide bonds followed by conjugation (standard ADC) with a thiol reactive drug linker intermediate.

Methods of Screening

Yet another embodiment of the present invention is directed to a method of determining the presence of a TENB2 polypeptide in a sample suspected of containing the TENB2 polypeptide, wherein the method comprises exposing the sample to a cysteine engineered anti-TENB2 antibody, or antibody drug conjugate thereof, that binds to the TENB2 polypeptide and determining binding of the cysteine engineered anti-TENB2 antibody, or antibody drug conjugate thereof, to the TENB2 polypeptide in the sample, wherein the presence of such binding is indicative of the presence of the TENB2 polypeptide in the sample. Optionally, the sample may contain cells (which may be cancer cells) suspected of expressing the TENB2 polypeptide. The cysteine engineered anti-TENB2 antibody, or antibody drug conjugate thereof, employed in the method may optionally be delectably labeled, attached to a solid support, or the like.

Another embodiment of the present invention is directed to a method of diagnosing the presence of a tumor in a mammal, wherein the method comprises (a) contacting a test sample comprising tissue cells obtained from the mammal with a cysteine engineered anti-TENB2 antibody, or antibody drug conjugate thereof, that binds to a TENB2 polypeptide and (b) detecting the formation of a complex between the cysteine engineered anti-TENB2 antibody, or antibody drug conjugate thereof, and the TENB2 polypeptide in the test sample, wherein the formation of a complex is indicative of the presence of a tumor in the mammal. Optionally, the cysteine engineered anti-TENB2 antibody, or antibody drug conjugate thereof, is detectably labeled, attached to a solid support, or the like, and/or the test sample of tissue cells is obtained from an individual suspected of having a cancerous tumor.

In Vitro Cell Proliferation Assays

One embodiment of the present invention is directed to a method for inhibiting the growth of a cell that expresses a TENB2 polypeptide, wherein the method comprises contacting the cell with a cysteine engineered anti-TENB2 antibody, or antibody drug conjugate thereof, to the TENB2 polypeptide causes inhibition of the growth of the cell expressing the TENB2. The cell may be a cancer cell and binding of the cysteine engineered antibody, or antibody drug conjugate thereof, to the TENB2 polypeptide causes death of the cell expressing the TENB2 polypeptide.

Generally, the cytotoxic or cytostatic activity of an antibody-drug conjugate (ADC) is measured by: exposing mammalian cells expressing TENB2 polypeptide to ADC in a cell culture medium; culturing the cells for a period from about 6 hours to about 5 days; and measuring cell viability. Mammalian cells useful for cell proliferation-assays include: (1) a TENB2 polypeptide-expressing LuCaP77 tumor xenograft; (2) a PC3-derived cell line engineered to stably express a portion of the TENB2 polypeptide on its cell surface (PC3/TENB2); and (3) a PC3 cell line that does not express TENB2 polypeptide (PC3/neo). Cell-based in vitro assays are used to measure viability (proliferation), cytotoxicity, and induction of apoptosis (caspase activation) of the ADC of the invention.

Pharmacokinetics—Serum Clearance and Stability

The disposition of the anti-TENB2 antibody-drug conjugates in vivo was analyzed by measuring the serum concentrations of antibody and of drug conjugate after a single intravenous bolus dose into Sprague-Dawley rats. Concentrations of antibody-drug conjugates bearing at least one cytotoxic drug were measured with an ELISA that used anti-MMAE for the capture and biotinylated TENB2 extracellular domain (ECD) and streptavidin-horseradish peroxidase (HRP) for detection. Total TMEFF2#19 and ThioTMEFF2#19 concentrations in serum were measured with an ELISA that used TENB2 ECD for capture and anti-human-Fc HRP as the secondary antibody. This assay measured any anti-TENB2 antibody, both with and without conjugated MMAE. The assays have lower limits of quantitation of 16.4 ng/mL with a minimum dilution of 1:100. The serum concentration-time data from each animal was analyzed using a two-compartment model with IV bolus input, first-order elimination, and macro-rate constants (Model 8, WinNonlin Pro v.5.0.1, Pharsight Corporation, Mountain View, Calif.). Overall goodness of fit was based on the predicted estimate, standard error for the prediction, and percentage of coefficient of variation for primary and secondary parameters, as well as inspection of residual plots between observed and predicted concentration-time data. Individual primary PK parameters comprised the zero-time intercepts (A and B) associated with the alpha and beta phases, respectively, and the micro-rate constants (alpha and beta). The following modeling options were used: Initial estimates were determined using WinNonlin; Concentrations were weighted by the reciprocal of the predicted concentration squared ($1/\hat{y}^2$); Nelder-Mead minimization algorithm was used. The following PK parameters were reported: $AUC_{0INF}$, CL, $C_{max}$, MRT, $t_{1/2,a}$, $t_{1/2,b}$, $V_1$ and $V_{ss}$.

Figure 15:
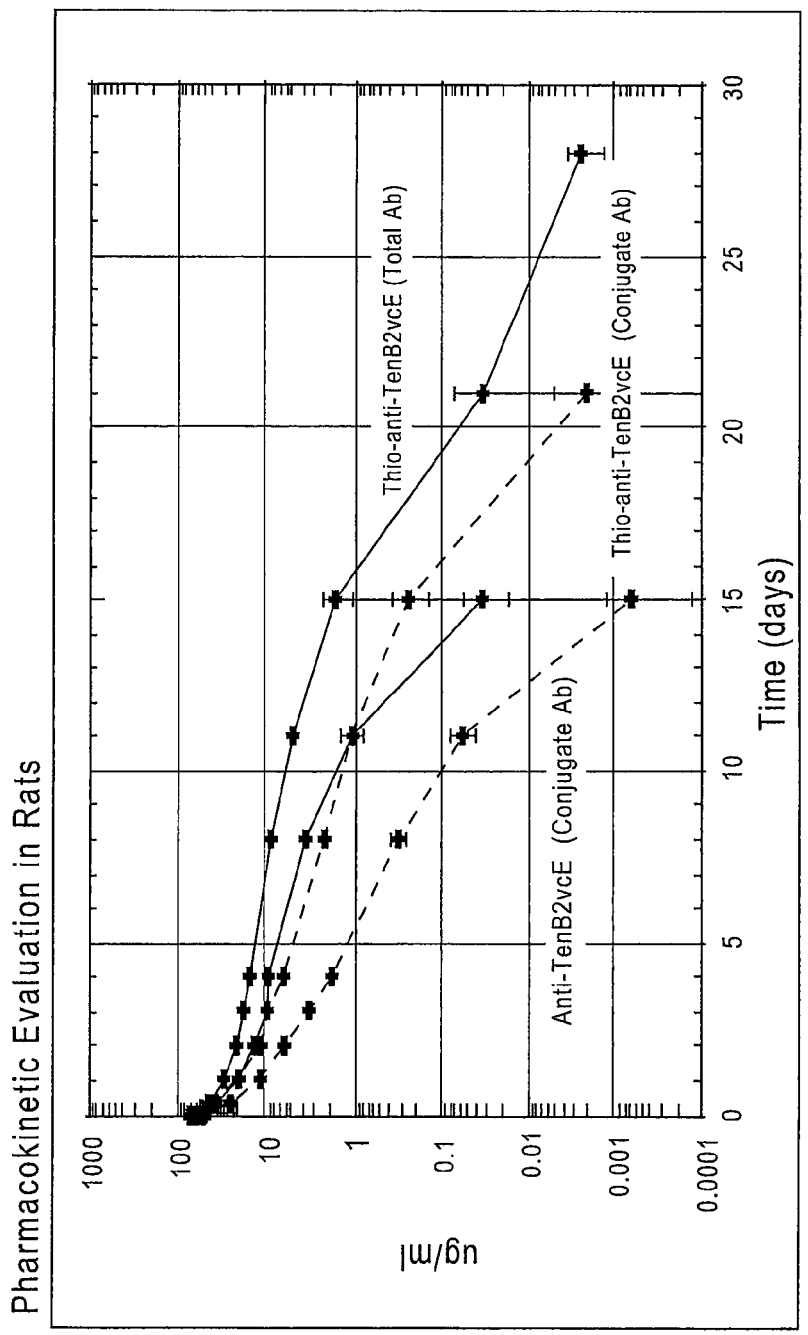
FIG. 15 shows pharmacokinetic evaluation of rats using thio-anti-TENB2 and conventional ADCs.
Figure 16:
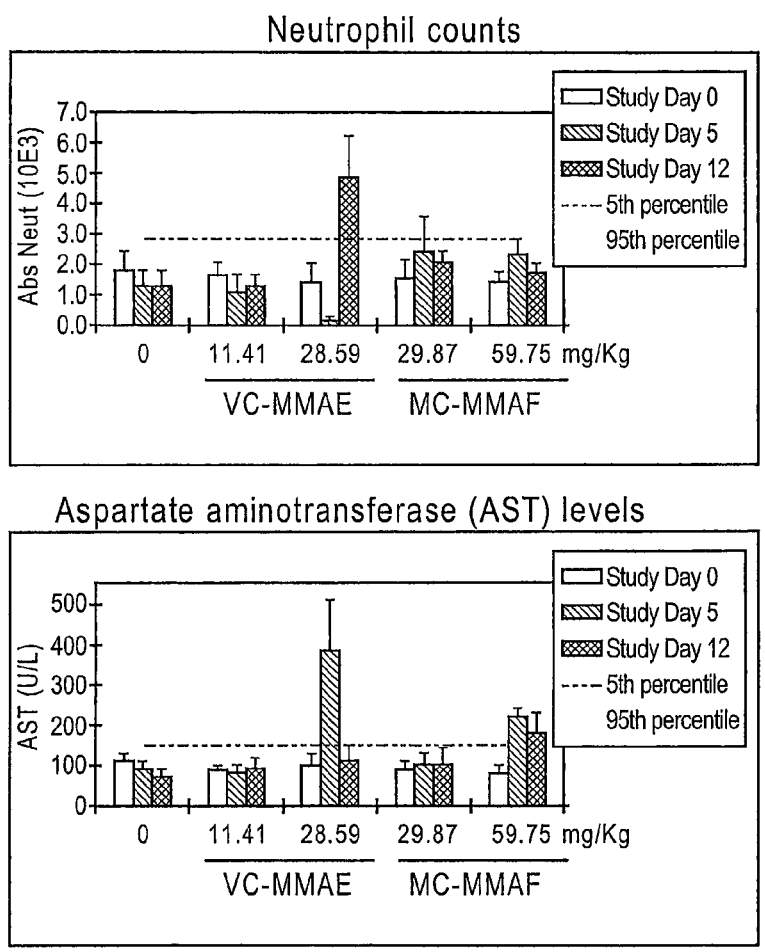
FIG. 16 shows a safety assessment on rats with anti-TENB2-vc-MMAE vs. MC-MMAF.
Figure 17B:
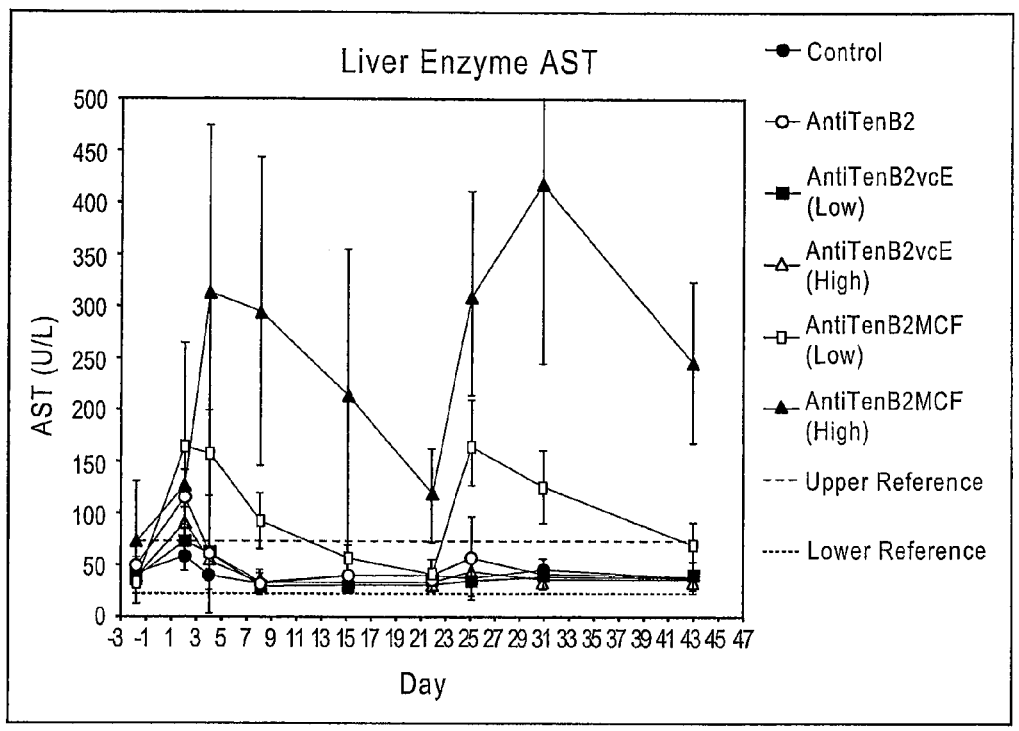
FIG. 17A and B shows a safety assessment on cynomolgus monkeys with anti-TENB2-vc-MMAE vs. anti-TENB2-MC-MMAF.
Figure 18A:
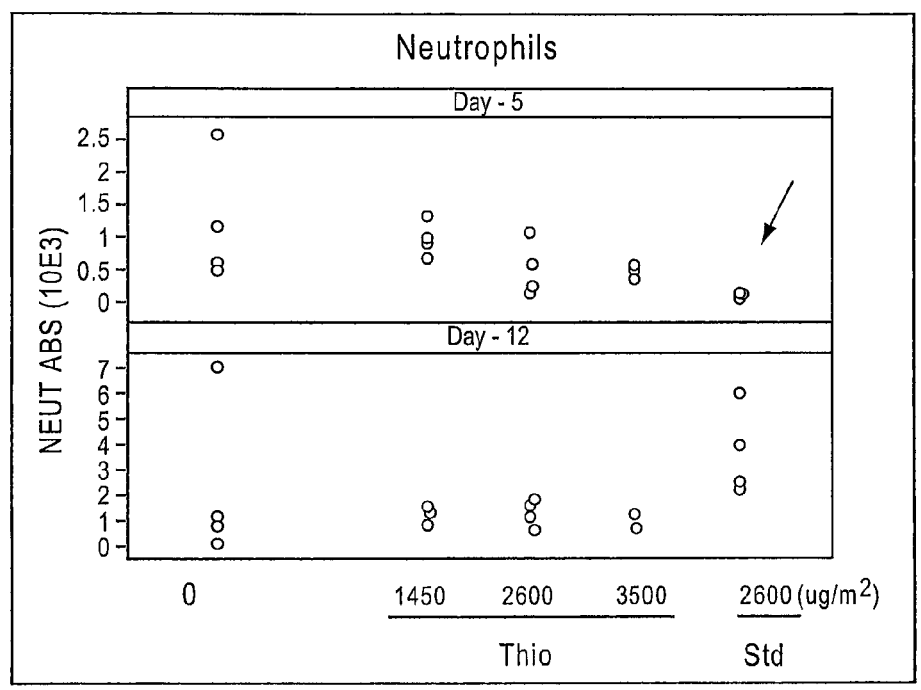
FIG. 18A and B shows a safety assessment on rats with thio-anti-TENB2-vc-MMAE vs. anti-TENB2-vc-MMAE.
Figure 18B:
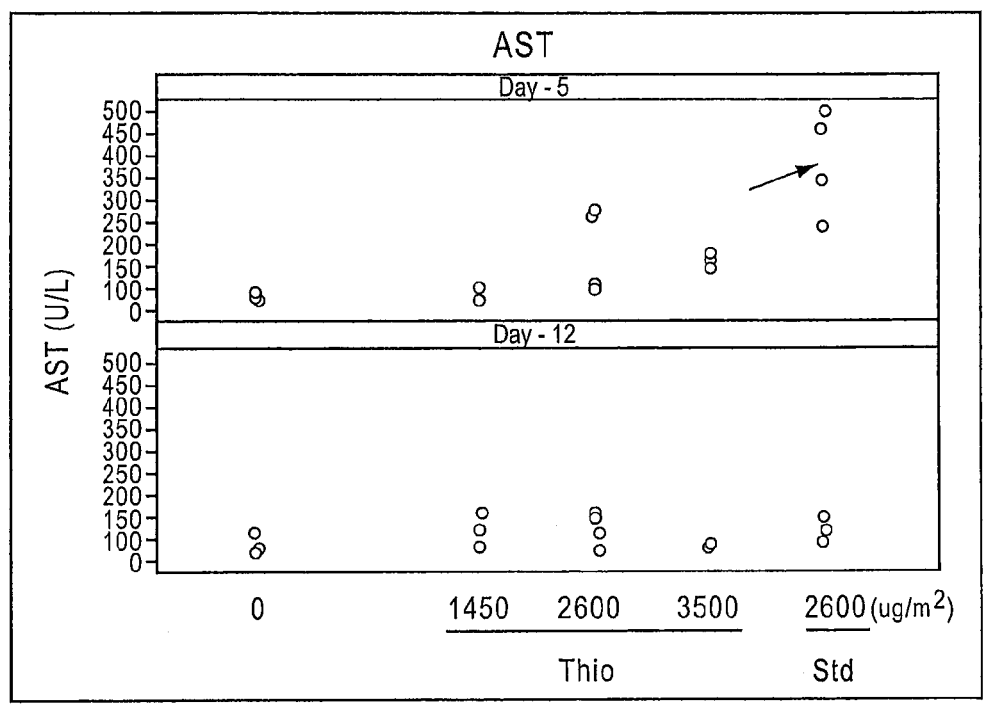

Results of 28-day pharmacokinetics analyses in rats are shown in FIG. 15. Rats were dosed with 5 mg/kg body weight of thio TMEFF2#19-VC-MMAE or 5 mg/kg TMEFF2#19-VC-MMAE. Serum from rats was collected at 5 minutes, 1 hour, 6 hours, 24 hours, and 2, 3, 4, 8, 11, 15, 21, and 28 days after dosing. Dose linearity of kinetics was observed for ch TMEFF2#19-VC-MMAE between 0.5 and 5 mg/kg dose, so the 5 mg/kg dose data have been arithmetically converted to reflect the predicted data at 5 mg/kg for comparison with thio TMEFF2#19-VC-MMAE.

Rodent Toxicity

The toxicity of cysteine engineered anti-TENB2 antibody-drug conjugates was evaluated in an acute toxicity rat and cynomolgus models. Toxicity of ADC was investigated by treatment of female Sprague-Dawley rats and cynomolgus monkeys with the ADC and subsequent inspection and analysis of the effects on various organs. Based on gross observations (body weights), clinical pathology parameters (serum chemistry and hematology) and histopathology, the toxicity of ADC may be observed, characterized, and measured. It was found that at equivalent dose levels, no target-dependant effects appeared. Target-independent toxicities were observed at doe that exceeded the efficacious doses in animal tumor models.

Methods of Treatment

Another embodiment of the present invention is directed to a method of therapeutically treating a mammal having a cancerous tumor comprising cells that express a TENB2 polypeptide, wherein the method comprises administering to the mammal a therapeutically effective amount of a cysteine engineered antibody, or antibody drug conjugate thereof, that binds to the TENB2 polypeptide, thereby resulting in the effective therapeutic treatment of the tumor.

Another embodiment of the present invention is directed to a method for treating or preventing a cell proliferative disorder associated with altered, preferably increased, expression or activity of a TENB2 polypeptide, the method comprising administering to a subject in need of such treatment an effective amount of a cysteine engineered anti-TENB2 antibody, or antibody drug conjugate thereof. An exemplary cell proliferative disorder is cancer. Effective treatment or prevention of the cell proliferative disorder may be a result of direct killing or growth inhibition of cells that express a TENB2 polypeptide or by antagonizing the cell growth potentiating activity of a TENB2 polypeptide with the cysteine engineered anti-TENB2 antibody, or antibody drug conjugate thereof.

Yet another embodiment of the present invention is directed to a method of binding a cysteine engineered anti-TENB2 antibody, or antibody drug conjugate thereof, to a cell that expresses a TENB2 polypeptide, wherein the method comprises contacting a cell that expresses a TENB2 polypeptide with said cysteine engineered anti-TENB2 antibody, or antibody drug conjugate thereof, under conditions which are suitable for binding of the cysteine engineered anti-TENB2 antibody, or antibody drug conjugate thereof, to said TENB2 polypeptide and allowing binding therebetween. In preferred embodiments, the cysteine engineered anti-TENB2 antibody, or antibody drug conjugate thereof, is labeled with a molecule or compound that is useful for qualitatively and/or quantitatively determining the location and/or amount of binding of the cysteine engineered anti-TENB2 antibody, or antibody drug conjugate thereof, to the cell.

Other embodiments of the present invention are directed to the use of a cysteine engineered anti-TENB2 antibody, or antibody drug conjugate thereof, in the preparation of a medicament useful for (i) the therapeutic treatment or diagnostic detection of a cancer or tumor, or (ii) the therapeutic treatment or prevention of a cell proliferative disorder.

Another embodiment of the present invention is directed to a method for inhibiting the growth of a cancer cell, wherein the growth of said cancer cell is at least in part dependent upon the growth potentiating effect(s) of a TENB2 polypeptide, wherein the method comprises contacting the TENB2 polypeptide with a cysteine engineered anti-TENB2 antibody, or antibody drug conjugate thereof, thereby antagonizing the growth-potentiating activity of the TENB2 polypeptide and, in turn, inhibiting the growth of the cancer cell, whereby the growth of the cancer cell is inhibited.

Another embodiment of the present invention is directed to a method of therapeutically treating a tumor in a mammal, wherein the growth of said tumor is at least in part dependent upon the growth potentiating effect(s) of a TENB2 polypeptide, wherein the method comprises administering to the mammal a therapeutically effective amount of an anti-TENB2 cysteine engineered antibody, or antibody drug conjugate thereof, that binds to the TENB2 polypeptide, thereby antagonizing the growth potentiating activity of said TENB2 polypeptide and resulting in the effective therapeutic treatment of the tumor.

The antibodies, antibody fragments, and conjugates thereof recognize extracellular epitopes of plasma membrane TENB2 proteins that are released into the extracellular fluid. The invention further provides methods for the detection, monitoring and treatment of malignancies such as breast cancer and ovarian cancer using the antibodies, antibody fragments and conjugates.

Antibody-drug conjugates (ADC) of the present invention may be used to treat various diseases or disorders, e.g. characterized by the overexpression of a TENB2 tumor antigen. Exemplary conditions or hyperproliferative disorders include benign or malignant tumors including prostate cancer.

The ADC compounds which are identified in the animal models and cell-based assays can be further tested in tumor-bearing higher primates and human clinical trials. The clinical trial may be designed to evaluate the efficacy of an ADC in combinations with known therapeutic regimens, such as radiation and/or chemotherapy involving known chemotherapeutic and/or cytotoxic agents.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight.

For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of an anti-TENB2 antibody. Other dosage regimens may be useful. The progress of this therapy is easily monitored by conventional techniques and assays including ultrasound imaging.

Administration of Antibody-Drug Conjugates

The antibody-drug conjugates (ADC) of the invention may be administered by any route appropriate to the condition to be treated. The ADC will typically be administered parenterally, i.e. infusion, subcutaneous, intraperitoneal, intramuscular, intravenous, intradermal, intrathecal and epidural.

Pharmaceutical Formulations

Pharmaceutical formulations of therapeutic antibody-drug conjugates (ADC) of the invention are typically prepared for parenteral administration, i.e. bolus, intravenous, intratumor injection with a pharmaceutically acceptable parenteral vehicle and in a unit dosage, sterile injectable form. An antibody-drug conjugate (ADC) having the desired degree of purity is optionally mixed with pharmaceutically acceptable diluents, carriers, excipients or stabilizers (*Remington's Pharmaceutical Sciences* (1980) 16th edition, Osol, A. Ed.), in the form of a lyophilized formulation or an aqueous solution.

Acceptable diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semi permeable matrices of solid hydrophobic polymers containing the ADC, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Aqueous suspensions of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of ADC may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Although oral administration of protein therapeutics are disfavored due to hydrolysis or denaturation in the gut, formulations of ADC suitable for oral administration may be prepared as discrete units such as capsules, cachets or tablets each containing a predetermined amount of the ADC.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The compositions of the invention may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al (1985) Proc. Natl. Acad. Sci. USA 82:3688; Hwang et al (1980) Proc. Natl. Acad. Sci. USA 77:4030; U.S. Pat. No. 4,485,045; U.S. Pat. No. 4,544,545; U.S. Pat. No. 5,013,556; WO 97/38731. Liposomes can be generated by the reverse phase evaporation method with a lipid composition comprising phosphatidylcholine, cholesterol and PEG-derivatized phosphatidylethanolamine (PEG-PE). Liposomes may be extruded through filters of defined pore size to yield liposomes with the desired diameter. Fab' fragments of the compositions of the present invention can be conjugated to liposomes (Martin et al (1982) J. Biol. Chem. 257:286-288), via a disulfide interchange reaction. A chemotherapeutic agent is optionally contained within the liposome (Gabizon et al (1989) J. National Cancer Inst. 81 (19):1484.

Combination Therapy

An antibody-drug conjugate (ADC) of the invention may be combined in a pharmaceutical combination formulation, or dosing regimen as combination therapy, with a second compound having anti-cancer properties. The second compound of the pharmaceutical combination formulation or dosing regimen preferably has complementary activities to the ADC of the combination such that they do not adversely affect each other.

The second compound may be a chemotherapeutic agent, cytotoxic agent, cytokine, growth inhibitory agent, anti-hormonal agent, and/or cardioprotectant. Such molecules are suitably present in combination in amounts that are effective for the purpose intended. A pharmaceutical composition containing an ADC of the invention may also have a therapeutically effective amount of a chemotherapeutic agent such as a tubulin-forming inhibitor, a topoisomerase inhibitor, a DNA intercalator, or a DNA binder.

Other therapeutic regimens may be combined with the administration of an anticancer agent identified in accordance with this invention. The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

In one embodiment, treatment with an ADC involves the combined administration of a cysteine engineered anti-TENB2 antibody or antibody-drug conjugate thereof, and one or more chemotherapeutic agents, therapeutic biological, or growth inhibitory agents, including coadministration of cocktails of different chemotherapeutic agents. Chemotherapeutic agents include, but are not limited to: taxanes (such as paclitaxel and docetaxel); platinum-containing compounds, such as carboplatin; EGFR inhibitors such as erlotinib, and gefitinib; tyrosine kinase inhibitors such as imatinib; and anthracycline antibiotics (such as doxorubicin or doxil). Therapeutic biological agents to be used in combination with a cysteine engineered anti-TENB2 antibody or antibody-drug conjugate thereof include bevacizumab (Avastin®) or pertuzumab (Omnitarg™, Genentech Inc). Preparation and dosing schedules for such chemotherapeutic agents may be used according to manufacturer's instructions or as determined empirically by the skilled practitioner. Preparation and dosing schedules for such chemotherapy are also described in "Chemotherapy Service", (1992) Ed., M. C. Perry, Williams & Wilkins, Baltimore, Md.

The ADC may be combined with an anti-hormonal compound; e.g., an anti-estrogen compound such as tamoxifen; an anti-progesterone such as onapristone (EP 616812); or an anti-androgen such as flutamide, in dosages known for such molecules. Where the cancer to be treated is hormone independent cancer, the patient may previously have been subjected to anti-hormonal therapy and, after the cancer becomes hormone independent, the ADC (and optionally other agents as described herein) may be administered to the patient. It may be beneficial to also coadminister a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Metabolites of the Antibody-Drug Conjugates

Also falling within the scope of this invention are the in vivo metabolic products of the ADC compounds described herein, to the extent such products are novel and unobvious over the prior art. Such products may result for example from the oxidation, reduction, hydrolysis, amidation, esterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products typically are identified by preparing a radiolabelled (e.g. $^{14}C$ or $^{3}H$) ADC, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the ADC compounds of the invention.

Articles of Manufacture

In another embodiment of the invention, an article of manufacture, or "kit", containing materials useful for the treatment of the disorders described above is provided. The article of manufacture comprises a container and a label or package insert on or associated with the container. The package insert may refer to instructions customarily included in commercial packages of therapeutic products and that contain information about the indications, usage, dosage, administration, contraindications and/or warnings concerning the use of such therapeutic products. Suitable containers include, for example, bottles, vials, syringes, blister pack, etc. The containers may be formed from a variety of materials such as glass or plastic.

In one embodiment, the article of manufacture comprises a container and a formulation of a cysteine engineered anti-TENB2 antibody, or antibody-drug conjugate thereof, contained within the container. The article may further optionally comprise a label affixed to the container, or a package insert included with the container, that refers to the use of the composition of matter for the therapeutic treatment or diagnostic detection of a tumor. The container holding the formulation is effective for storing and delivering the therapeutic and may have a sterile access port (for example the container may be an intravenous solution bag or a vial having a stopper pierceable by a hypodermic injection needle). The label or package insert indicates that the formulation is used for treating the condition of choice, such as cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Preparation of Anti-TMEFF2#19 Antibodies

Humanized TMEFF2#19 antibodies were prepared according to PCT/US03/07209 (U.S. Pat. No. 7,288,248).

FIG. 1 shows the heavy chain amino acid sequence (SEQ ID NO:1) and the light chain amino acid sequence (SEQ ID NO:2).

Example 2

Preparation of Cysteine Engineered Anti-TENB2 Antibodies for Conjugation by Reduction and Reoxidation Full length, cysteine engineered anti-TENB2 monoclonal antibodies (ThioMabs) expressed in CHO cells bear cysteine adducts (cystines) on the engineered cysteines due to cell culture conditions. To liberate the reactive thiol groups of the engineered cysteines, the ThioMabs are dissolved in 500 mM sodium borate and 500 mM sodium chloride at about pH 8.0 and reduced with about a 50-100 fold excess of 1 mM TCEP (tris(2-carboxyethyl)phosphine hydrochloride; Getz et al (1999) Anal. Biochem. Vol 273:73-80; Soltec Ventures, Beverly, Mass.) for about 1-2 hrs at 37° C. The reduced ThioMab (FIG. 6) is diluted and loaded onto a HiTrap S column in 10 mM sodium acetate, pH 5, and eluted with PBS containing 0.3M sodium chloride. The eluted reduced ThioMab is treated with 2 mM dehydroascorbic acid (dhAA) at pH 7 for 3 hours, or 2 mM aqueous copper sulfate ($CuSO_4$) at room temperature overnight. Ambient air oxidation may also be effective. The buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm.

Example 3

Conjugation of Cysteine Engineered Anti-TENB2 Antibodies and Drug-Linker Intermediates After the reduction and reoxidation procedures of Example 2, the cysteine engineered anti-TENB2 antibody is dissolved in PBS (phosphate buffered saline) buffer and chilled on ice. About 1.5 molar equivalents relative to engineered cysteines per antibody of an auristatin drug linker intermediate, such as MC-MMAE (maleimidocaproyl-monomethyl auristatin E), MC-MMAF, MC-val-cit-PAB-MMAE, or MC-val-cit-PAB-MMAF, with a thiol-reactive functional group such as maleimido, is dissolved in DMSO, diluted in acetonitrile and water, and added to the chilled reduced, reoxidized antibody in PBS. After about one hour, an excess of maleimide is added to quench the reaction and cap any unreacted antibody thiol groups. The reaction mixture is concentrated by centrifugal ultrafiltration and the cysteine engineered anti-TENB2 antibody drug conjugate is purified and desalted by elution through G25 resin in PBS, filtered through 0.2 µm filters under sterile conditions, and frozen for storage.

By the procedure above, the following cysteine engineered anti-TENB2 antibody drug conjugates were prepared:

thio hu TMEFF2#19-MC-MMAF by conjugation of A114C (Kabat) thio hu TMEFF2#19 and MC-MMAF; and thio hu TMEFF2#19-MC-val-cit-PAB-MMAE by conjugation of A114C (Kabat) thio hu TMEFF2#19 and MC-val-cit-PAB-MMAE.

Example 4

Materials and Methods for IHC, Internalization Studies, FACS, Cell Killing Assays, Western Blots, Xenograft Studies, Pharmacokinetic Studies and Safety Assessments Antibodies and Recombinant Proteins: Humanized anti-tenb2 Mab PR1 was obtained from PDL. ThioMab anti-tenB2 PR1(HC-A121C; sequential numbering) and tenB2ECD Flag protein were produced as discussed above.

Cell Lines and Human Tumor Xenografts: PC3 is a human prostate carcinoma cell line (ATCC). PC3TenB2 Medium stable cell line was generated by Genentech. Human prostate explant models, LuCap70, 77 and 96.1 were obtained from the University of Washington.

RNA and Protein Expression: RNA expression analysis, Immunological procedures (IHC, Western), antibody binding (FACS) and internalization followed previously published methods (Cancer research 64, 781-788 (2004)).

Preparation of Conventional or ThioMab Anti-TenB2-Valine-Citrulline(vc)-Monomethylauristatine E(MMAE) and MC-MMAF Armed Drug Conjugated(ADC): The conjugation of conventional, thio-mab and control mab with vc-MMAE, MC-MMAF ADC was performed as described above.

In vitro Cell Killing and in vivo Studies: The cell killing assay was done similar to as described in Cancer research 64, 781-788 (2004). Each prostate explant model tumor cell line was maintained by serial transplantation in castrated (androgen independent model, LuCap70) or uncastrated (androgen dependent model, LuCAP77 and LuCAP96.1), male SCID-beige mice from Charles River lab. Tumors were measured once to twice per week for duration of the study.

Rats and Cynomolgus Monkeys Models for Safety Assessment: Anti-tenb2 Mab specifically recognized human, monkey and rats tenb2 target (FS I domain).

Pharmacokinetic Study: Standard protocol and assay methods were used.

The data demonstrate that human TenB2 (TMEFF2) is generally restricted to expression in the prostate and CNS, with significantly elevated levels in cancerous prostate. Anti-TenB2 antibodies were also demonstrated to be rapidly internalized. These antibodies, when conjugated to MMAE and MMAF were shown to kill prostate tumor cells in vitro and in vivo in various cell killing assays. Furthermore, efficacious doses of TENB2-ADCs were significantly lower than those that are required to elicit toxic effects in rodents and primates.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

---

We claim:

1. A cysteine engineered anti-TENB2 antibody comprising a heavy and a light chain, one or more free cysteine amino acid residues located in the heavy chain, and the sequence:

| Sequence near Cys mutation | Sequential Numbering | Kabat Numbering | Seq. I.D. |
|---|---|---|---|
| VTVSSCSTKGP | A121C | A114C | 12 | in combination with one or more additional cysteine mutations in the heavy chain, selected from the group consisting of:

| Sequence near Cys mutation | Sequential Numbering | Kabat Numbering | Seq. I.D. |
|---|---|---|---|
| DVQLCESGPG | Q5C | Q5C | 8 |
| LSLTCCVSGYS | A23C | A23C | 9 |
| VSSASCKGPSV | T123C | T116C | 13 |
| WYVDGCEVHNA | V285C | V278C | 14 |
| KGFYPCDIAVE | S378C | S371C | 15 |
| PPVLDCDGSFF | S403C | S396C | 16. |

2. A cysteine engineered anti-TENB2 antibody comprising a heavy and a light chain, wherein said antibody comprises one or more free cysteine amino acid residues located in the heavy chain, and cysteine mutations:

| Sequence near Cys mutation | Sequential Numbering | Kabat Numbering | Seq. I.D. |
|---|---|---|---|
| VTVSSCSTKGP | A121C | A114C | 12 | and

| Sequence near Cys mutation | Sequential Numbering | Kabat Numbering | Seq. I.D. |
|---|---|---|---|
| DVQLCESGPG | Q5C | Q5C | 8. |

3. The cysteine engineered anti-TENB2 antibody of claim 1 or claim 2 prepared by a process comprising replacing one or more amino acid residues of a parent anti-TENB2 antibody by cysteine.

4. The cysteine engineered anti-TENB2 antibody of claim 1 or claim 2 further comprising one or more free cysteine amino acid residues located in the light chain.

5. The cysteine engineered anti-TENB2 antibody of claim 4 comprising in the light chain one or more sequences selected from:

| Sequence near Cys mutation | Sequential Numbering | Kabat Numbering | Seq. I.D. |
|---|---|---|---|
| SLSASCGDRVT | V15C | V15C | 17 |
| EIKRTCAAPSV | V110C | V110C | 18 |
| TVAAPCVFIFP | S114C | S114C | 19 |
| FIFPPCDEQLK | S121C | S121C | 20 |
| DEQLKCGTASV | S127C | S127C | 21 |
| VTEQDCKDSTY | S168C | S168C | 22 |
| GLSSPCTKSFN | V205C | V205C | 23. |

6. The cysteine engineered anti-TENB2 antibody of claim 1 or claim 2 which is engineered from a parent anti-TENB2 antibody selected from a monoclonal antibody, a bispecific antibody, a chimeric antibody, a human antibody, and a humanized antibody.

7. The cysteine engineered anti-TENB2 antibody of claim 1 or claim 2 which is an antibody fragment.

8. The cysteine engineered anti-TENB2 antibody of claim 7 wherein the antibody fragment is a Fab fragment.

9. The cysteine engineered anti-TENB2 antibody of claim 1 or claim 2 which is selected from a chimeric antibody, a human antibody, or a humanized antibody.

10. The cysteine engineered anti-TENB2 antibody of claim 1 or claim 2 which is produced in bacteria.

11. The cysteine engineered anti-TENB2 antibody of claim 1 or claim 2 which is produced in CHO cells.

12. A pharmaceutical formulation comprising the cysteine engineered anti-TENB2 antibody of claim 1 or claim 2, and a pharmaceutically acceptable diluent, carrier or excipient.

13. The cysteine engineered anti-TENB2 antibody of claim 1 or claim 2 wherein the antibody is covalently attached to an auristatin drug moiety whereby an antibody drug conjugate is formed.

14. The antibody-drug conjugate of claim 13 comprising a cysteine engineered anti-TENB2 antibody (Ab), and an auristatin drug moiety (D) wherein the cysteine engineered anti-TENB2 antibody is attached through one or more free cysteine amino acids by a linker moiety (L) to D; the compound having Formula I:

     I where p is 1, 2, 3, or 4.

15. The antibody-drug conjugate compound of claim 14 wherein p is 2.

16. The antibody-drug conjugate compound of claim 14 wherein L has the formula:

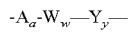

where:
A is a Stretcher unit covalently attached to a cysteine thiol of the cysteine engineered antibody (Ab);
a is 0 or 1;
each W is independently an Amino Acid unit;
w is an integer ranging from 0 to 12;
Y is a Spacer unit covalently attached to the drug moiety; and
y is 0, 1 or 2.

17. The antibody-drug conjugate compound of claim 16 having the formula:

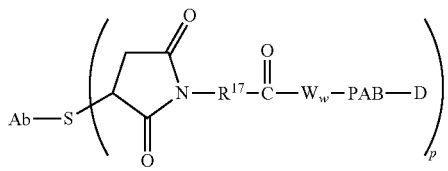

where PAB is para-aminobenzylcarbamoyl, and $R^{17}$ is a divalent radical selected from $(CH_2)_r$, $C_3$-$C_8$ carbocyclyl, O—$(CH_2)_r$, arylene, $(CH_2)_r$-arylene, -arylene-$(CH_2)_r$—, $(CH_2)_r$—$(C_3$-$C_8$ carbocyclyl), $(C_3$-$C_8$ carbocyclyl)-$(CH_2)_r$, $C_3$-$C_8$ heterocyclyl, $(CH_2)_r$—$(C_3$-$C_8$ heterocyclyl), —$(C_3$-$C_8$ heterocyclyl)-$(CH_2)_r$—, —$(CH_2)_r$C(O)$NR^b$(CH_2)_r$—, —$(CH_2CH_2O)_r$—, —$(CH_2CH_2O)_r$—$CH_2$—, —$(CH_2)_r$C(O)$NR^b$ $(CH_2CH_2O)_r$—, —$(CH_2)_r$C(O)$NR^b$(CH_2CH_2O)_r$—$CH_2$—, —$(CH_2CH_2O)_r$C(O)$NR^b$(CH_2CH_2O)_r$—, —$(CH_2CH_2O)_r$C(O)$NR^b$(CH_2CH_2O)_r$—$CH_2$—, and —$(CH_2CH_2O)_r$C(O)$NR^b$(CH_2)_r$—; where $R^b$ is H, $C_1$-$C_6$ alkyl, phenyl, or benzyl; and r is independently an integer ranging from 1 to 10.

18. The antibody-drug conjugate compound of claim 16 wherein $W_w$ is valine-citrulline.

19. The antibody-drug conjugate compound of claim 17 wherein $R^{17}$ is $(CH_2)_5$ or $(CH_2)_2$.

20. The antibody-drug conjugate compound of claim 16 having the formula:

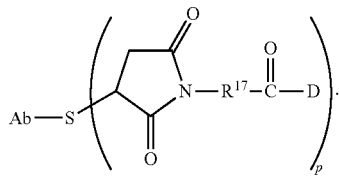

21. The antibody-drug conjugate compound of claim 20 wherein $R^{17}$ is $(CH_2)_5$ or $(CH_2)_2$.

22. The antibody-drug conjugate compound of claim 16 having the formula:

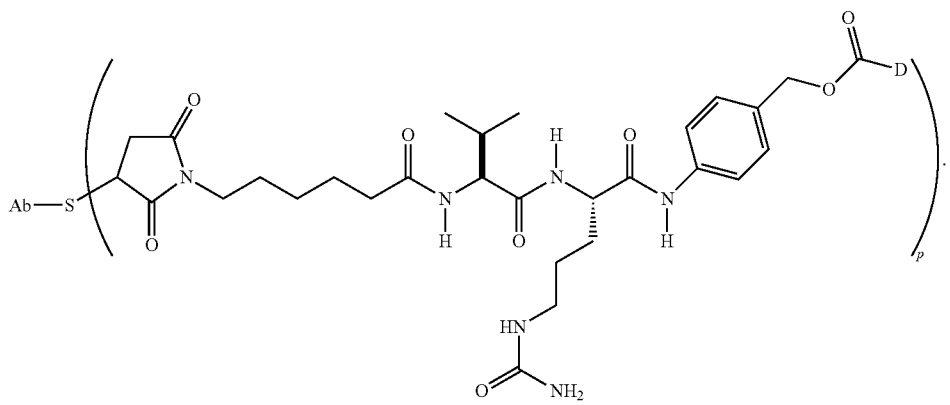

23. The antibody-drug conjugate compound of claim 14 wherein L is SMCC or BMPEO.

24. The antibody-drug conjugate compound of claim 14 wherein D is MMAE, having the structure:

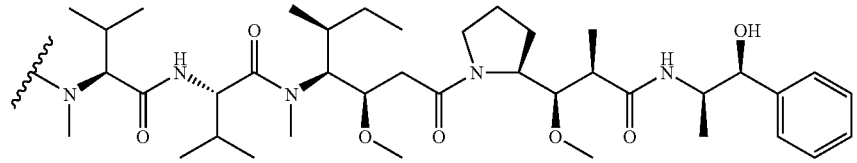 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

where the wavy line indicates the attachment site to the linker L.

25. The antibody-drug conjugate compound of claim 14 wherein D is MMAF, having the structure:

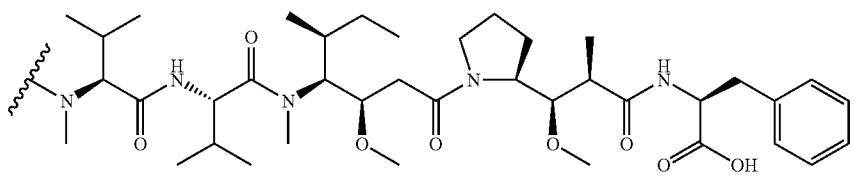 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

where the wavy line indicates the attachment site to the linker L.

26. The antibody-drug conjugate compound of claim 13 wherein the parent anti-TENB2 antibody is selected from a monoclonal antibody, a bispecific antibody, a chimeric antibody, a human antibody, and a humanized antibody.

27. The antibody-drug conjugate compound of claim 13 which is engineered from a parent anti-TENB2 antibody that is an antibody fragment.

28. The antibody-drug conjugate compound of claim 27 wherein the antibody fragment is a Fab fragment.

29. The antibody drug conjugate of claim 13 wherein the auristatin is MMAE or MMAF.

30. The antibody drug conjugate of claim 13 wherein L is MC-val-cit-PAB or MC.

31. The antibody drug conjugate of claim 13 wherein L is SMCC, SPP, or BMPEO.

32. An antibody-drug conjugate compound selected from the structures:

wherein Val is valine; Cit is citrulline; p is 1, 2, 3, or 4; and Ab is a cysteine engineered anti-TENB2 antibody of claim 1.

33. The antibody drug conjugate of claim 32 wherein Ab comprises SEQ ID NO:2.

34. A pharmaceutical formulation comprising the antibody drug conjugate of claim 13, and a pharmaceutically acceptable diluent, carrier or excipient.

35. The pharmaceutical formulation of claim 34 further comprising a therapeutically effective amount of a chemotherapeutic agent selected from letrozole, oxaliplatin, doxetaxel, 5-FU, lapatinib, capecitabine, leucovorin, erlotinib, pertuzumab, bevacizumab, and gemcitabine.

36. An article of manufacture comprising
the pharmaceutical formulation of claim 34;
a container; and
a package insert or label indicating that the compound can be used to treat cancer characterized by the overexpression of a TENB2 polypeptide.

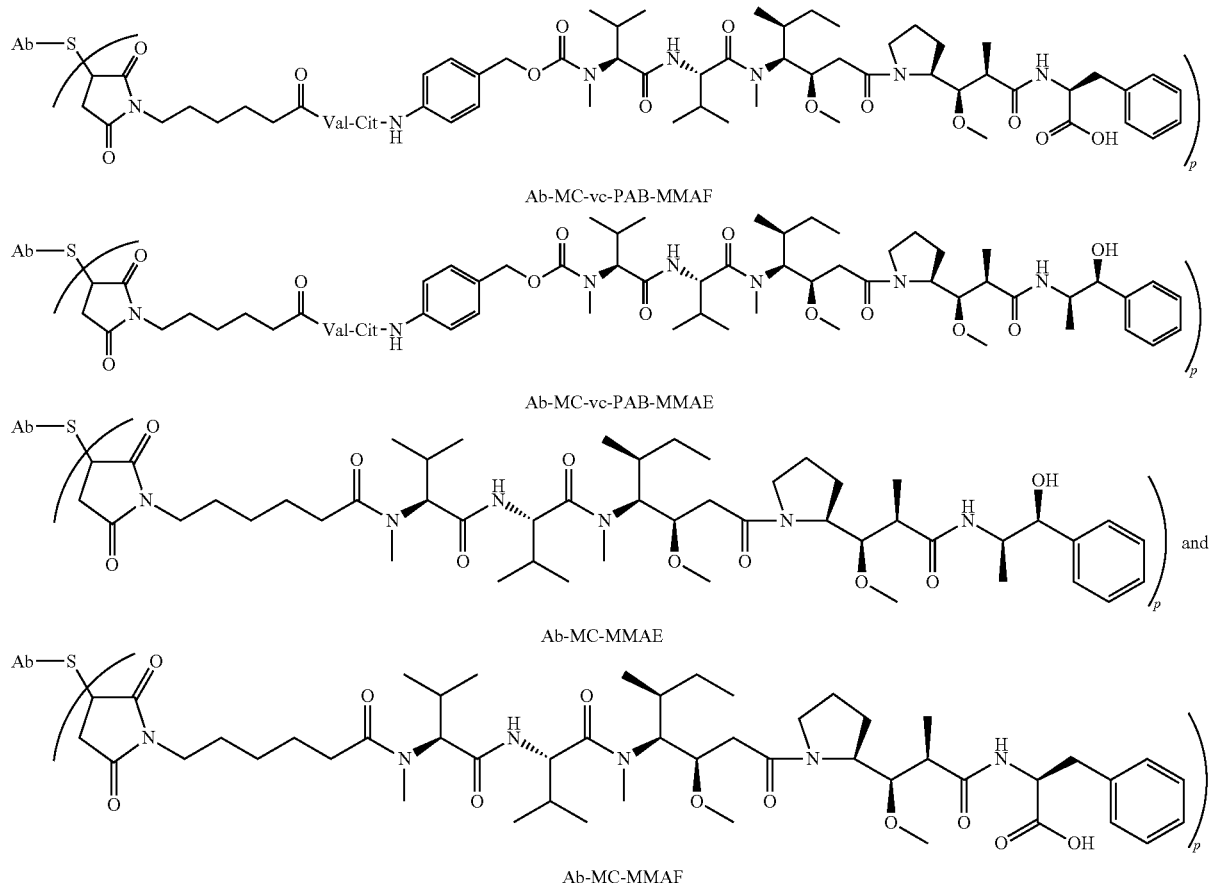

37. The article of manufacture of claim 36 wherein the cancer is ovarian cancer, prostate cancer, cancer of the urinary tract, pancreatic cancer, lung cancer, breast cancer, or colon cancer.

* * * * *

SEQUENCE LISTING

```
<160> NUMBER OF SEQ ID NOS: 27

<210> SEQ ID NO 1
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Val Leu Gly Leu Leu Leu Cys Leu Val Thr Phe Pro Ser Cys
1               5                   10                  15

Val Leu Ser Asp Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Thr Ser Gly Tyr Tyr Trp Ser Trp Ile Arg Gln Pro Pro Gly Lys Gly
    50                  55                  60

Leu Glu Trp Met Gly Phe Ile Ser Tyr Asp Gly Ser Asn Lys Tyr Asn
65                  70                  75                  80

Pro Ser Leu Lys Asn Arg Ile Thr Ile Ser Arg Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Gly Leu Arg Arg Gly Asp Tyr Ser Met Asp Tyr
        115                 120                 125

Trp Gly Gln Gly Thr Leu Val Thr Val Ser Ser Ala Ser Thr Lys Gly
```

```
            130                 135                 140
Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 2
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asp Phe Gln Val Gln Ile Phe Ser Phe Leu Leu Ile Ser Ala Ser
1               5                   10                  15
```

```
Val Ile Met Ser Arg Gly Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asn Val Val Thr Ala Val Ala Trp Tyr Gln Gln Lys Pro Gly Lys
    50                  55                  60

Ala Pro Lys Leu Leu Ile Tyr Ser Ala Ser Asn Arg His Thr Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Ser Ser Tyr Pro Phe Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 3
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Val Leu Gly Leu Leu Leu Cys Leu Val Thr Phe Pro Ser Cys
1               5                   10                  15

Val Leu Ser Asp Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Thr Ser Gly Tyr Tyr Trp Ser Trp Ile Arg Gln Pro Pro Gly Lys Gly
    50                  55                  60

Leu Glu Trp Met Gly Phe Ile Ser Tyr Asp Gly Ser Asn Lys Tyr Asn
65                  70                  75                  80

Pro Ser Leu Lys Asn Arg Ile Thr Ile Ser Arg Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Gly Leu Arg Arg Gly Asp Tyr Ser Met Asp Tyr
        115                 120                 125

Trp Gly Gln Gly Thr Leu Val Thr Val Ser Ser Cys Ser Thr Lys Gly
    130                 135                 140
```

```
Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
        180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
        210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Lys
465

<210> SEQ ID NO 4
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
```

```
            20                  25                  30
Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Val Val Thr Ala
             20                  25                  30

Val Ala Trp Tyr Gln Gln Lys Pro Gly Lys Ala Pro Lys Leu Leu Ile
             35                  40                  45

Tyr Ser Ala Ser Asn Arg His Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Ser Tyr Pro Phe
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 7
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Gly
            20                  25                  30

Tyr Tyr Trp Ser Trp Ile Arg Gln Pro Pro Gly Lys Gly Leu Glu Trp
        35                  40                  45

Met Gly Phe Ile Ser Tyr Asp Gly Ser Asn Lys Tyr Asn Pro Ser Leu
    50                  55                  60

Lys Asn Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Gly Leu Arg Arg Gly Asp Tyr Ser Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
```

```
                195                 200                 205
Pro Ser Asn Thr Lys Val Asp Lys Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
Gly Lys
    450

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Val Gln Leu Cys Glu Ser Gly Pro Gly
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Ser Leu Thr Cys Cys Val Ser Gly Tyr Ser
1               5                   10
```

```
<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Ser Ser Val Thr Cys Ala Asp Thr Ala Val
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Leu Val Thr Val Cys Ser Ala Ser Thr Lys
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Thr Val Ser Ser Cys Ser Thr Lys Gly Pro
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Ser Ser Ala Ser Cys Lys Gly Pro Ser Val
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Tyr Val Asp Gly Cys Glu Val His Asn Ala
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15
```

```
Lys Gly Phe Tyr Pro Cys Asp Ile Ala Val Glu
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Pro Val Leu Asp Cys Asp Gly Ser Phe Phe
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Leu Ser Ala Ser Cys Gly Asp Arg Val Thr
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Ile Lys Arg Thr Cys Ala Ala Pro Ser Val
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Val Ala Ala Pro Cys Val Phe Ile Phe Pro
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Ile Phe Pro Pro Cys Asp Glu Gln Leu Lys
1               5                   10

<210> SEQ ID NO 21
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 21

Asp Glu Gln Leu Lys Cys Gly Thr Ala Ser Val
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Thr Glu Gln Asp Cys Lys Asp Ser Thr Tyr
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Leu Ser Ser Pro Cys Thr Lys Ser Phe Asn
1               5                   10

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 24

His His His His His His
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      8x His tag

<400> SEQUENCE: 25

His His His His His His His His
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Asp Tyr Lys Asp Asp Asp Asp Lys
1               5
```

```
<210> SEQ ID NO 27
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Tyr Ala Leu Ala Asp Ala Ser Leu Lys Met Ala Asp Pro Asn Arg
1               5                   10                  15

Phe Arg Gly Lys Asp Leu Pro Val Leu
            20                  25
```